US010564281B2

(12) United States Patent
Abe et al.

(10) Patent No.: US 10,564,281 B2
(45) Date of Patent: Feb. 18, 2020

(54) ULTRASONOGRAPHY APPARATUS AND ULTRASONIC IMAGING METHOD

(71) Applicant: Toshiba Medical Systems Corporation, Otawara-shi (JP)

(72) Inventors: Yasuhiko Abe, Otawara (JP); Yasunori Honjo, Otawara (JP)

(73) Assignee: Canon Medical Systems Corporation, Otawara-shi (JP)

(*) Notice: Subject to any disclaimer, the term of this patent is extended or adjusted under 35 U.S.C. 154(b) by 869 days.

(21) Appl. No.: 14/688,373

(22) Filed: Apr. 16, 2015

(65) Prior Publication Data
US 2015/0320396 A1 Nov. 12, 2015

(30) Foreign Application Priority Data
May 8, 2014 (JP) .................................. 2014-097153

(51) Int. Cl.
*A61B 8/08* (2006.01)
*G01S 15/89* (2006.01)

(52) U.S. Cl.
CPC ........ *G01S 15/8995* (2013.01); *A61B 8/5207* (2013.01)

(58) Field of Classification Search
CPC ............. G01S 15/8995; G01S 7/52046; G01S 7/52077; A61B 8/5207; A61B 8/5253
See application file for complete search history.

(56) References Cited

U.S. PATENT DOCUMENTS 5,581,517 A * 12/1996 Gee .................... G01S 7/52046
367/11
5,685,308 A * 11/1997 Wright ................ G01S 7/52023
600/443

(Continued)

FOREIGN PATENT DOCUMENTS

JP  2012-071115 A  4/2012

OTHER PUBLICATIONS

Seo et al., "Sidelobe Suppression in Ultrasound Imaging Using Deal Apodization with Cross-Correlation" IEEE Transactions on Ultrasonics, Ferroelectrics, and Frequency Control, vol. 55, No. 10, Oct. 2008 pp. 2198-2210.*

(Continued)

*Primary Examiner* — Katherine L Fernandez
*Assistant Examiner* — Colin T. Sakamoto
(74) *Attorney, Agent, or Firm* — Oblon, McClelland, Maier & Neustadt, L.L.P.

(57) ABSTRACT

An ultrasonography apparatus includes an acquiring unit, a calculating unit, a multiplying unit, and a generating unit. The acquiring unit acquires a plurality of reception signals that are generated by assigning various kinds of weights on multiple reflected wave signals to which a delay according to a position in a reception aperture is given, and by adding the weighted signals for respective kinds of the weights. The calculating unit calculates a coefficient corresponding to each of positions on a scan line of the reception signals, based on any one of a signal and pixel value of each of positions based on at least one reception signal. The multiplying unit multiplies any one of the values of each of positions based on at least one different reception signal from said reception signal(s) by the coefficient to acquire output data. The generating unit generates ultrasonic image data based on the data.

21 Claims, 27 Drawing Sheets

(56) References Cited

U.S. PATENT DOCUMENTS

| | | | | |
|---|---|---|---|---|
| 6,436,044 | B1* | 8/2002 | Wang | G01S 7/52047 600/443 |
| 8,254,654 | B2* | 8/2012 | Yen | G01S 7/52047 382/128 |
| 8,606,037 | B2* | 12/2013 | Ali | H04N 5/20 382/274 |
| 8,675,445 | B2* | 3/2014 | Kim | G01S 7/52047 367/7 |
| 2009/0141957 | A1* | 6/2009 | Yen | G01S 7/52047 382/131 |
| 2012/0157850 | A1* | 6/2012 | Sumi | A61B 8/0891 600/443 |
| 2012/0275261 | A1* | 11/2012 | Kim | G01S 7/52047 367/7 |
| 2013/0343627 | A1* | 12/2013 | Zwirn | A61B 8/5269 382/131 |
| 2015/0011882 | A1 | 1/2015 | Abe | |

OTHER PUBLICATIONS

U.S. Appl. No. 14/709,628, filed May 12, 2015, Honjo, et al.
U.S. Appl. No. 14/324,670, filed Jul. 7, 2014, 2015/0011882 A1, Yasuhiko Abe.

* cited by examiner

ULTRASONOGRAPHY APPARATUS AND ULTRASONIC IMAGING METHOD

CROSS-REFERENCE TO RELATED APPLICATION

This application is based upon and claims the benefit of priority from Japanese Patent Application No. 2014-97153, filed on May 8, 2014, the entire contents of all of which are incorporated herein by reference.

FIELD

Embodiments described herein relate generally to an ultrasonography apparatus and an ultrasonic imaging method.

BACKGROUND

Conventionally, various methods have been applied to reduce reverberation echoes of an ultrasonic image (B-mode image) that interfere with a diagnosis. As one example of such a method, a method of compounding multiple pieces of B-mode images with various deflection angles in transmission and reception of ultrasonic waves by signal averaging has been known. Moreover, applying this method, a method has also been known in which a degree and a position of a reverberation echo component are estimated from B-mode images with various deflection angles, and a weight at signal averaging is adaptively controlled from an estimation result.

However, in the above method of compounding multiple images with various deflection angles, an influence of reduced amplitude when a deflection angle is increased cannot be avoided due to the constraint of element factors. That is, in an image taken in an inclined direction, the lateral resolution is degraded compared to an ordinary image with a deflection angle "0 degree" (center image). Furthermore, in an image taken in an inclined direction, the sensitivity (S/N ratio) relative to a center image is also degraded.

Therefore, in an output image that is obtained by compounding multiple images with various deflection angles, the lateral resolution and the sensitivity are degraded with respect to an ordinary center image.

DETAILED DESCRIPTION

An ultrasonography apparatus of an embodiment includes an acquiring unit, a calculating unit, a multiplying unit, and an image generating unit. The acquiring unit assigns various kinds of weights to reflected wave signals that are generated at a reception aperture structured with multiple devices included in an ultrasound probe, and with which a delay according to a position inside the reception aperture is multiplied, and acquires reception signals that are generated by adding the weighted reflected wave signals for each kind of the weights. The calculating unit calculates a coefficient that corresponds to each of positions on a reception scan line corresponding to the reception signals acquired by the acquiring unit, based on a signal value or an image value that is a signal value or a pixel value based on at least one reception signal among the reception signals, and that corresponds to each of the positions. The multiplying unit multiplies, by the coefficient, a signal value or a pixel value that is based on at least one reception signal different from the at least one reception signal among the reception signals, and that corresponds to each of the positions on the reception scan line, to acquire output data. The image generating unit generates ultrasonic image data based on the output data acquired by the multiplying unit.

Embodiments of the ultrasonography apparatus are explained in detail below with reference to the accompanying drawings.

First Embodiment

Figure 1:
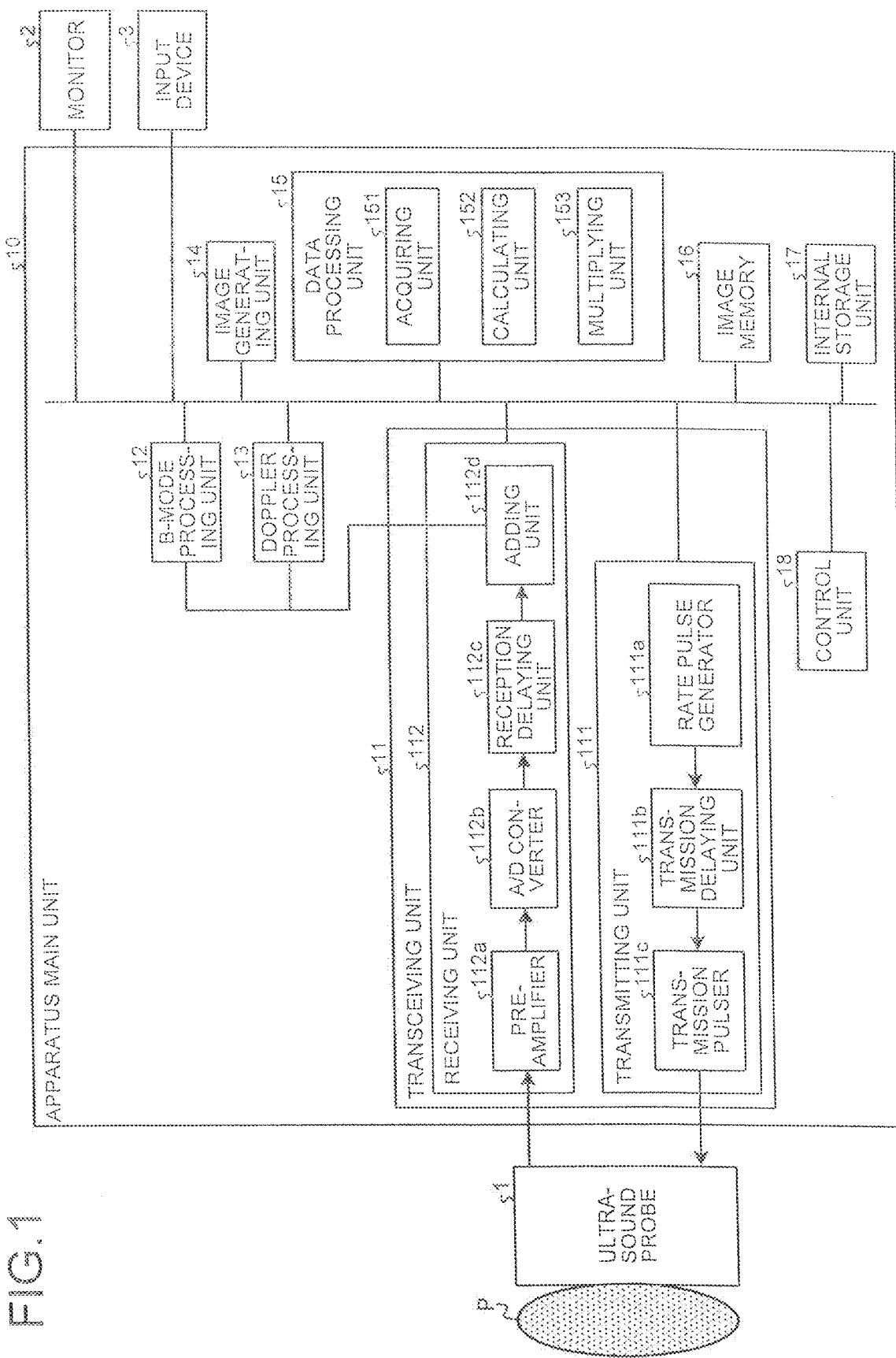
FIG. 1 is a block diagram indicating a configuration example of an ultrasonography apparatus according to a first embodiment.

First, a configuration of an ultrasonography apparatus according to a first embodiment is explained. FIG. 1 is a block diagram indicating a configuration example of the ultrasonography apparatus according to the first embodiment. As exemplified in FIG. 1, the ultrasonography apparatus according to the first embodiment includes an ultrasound probe 1, a monitor 2, an input device 3, and an apparatus main unit 10.

The ultrasound probe 1 includes multiple transducers (for example, piezoelectric transducers), and these transducers generate ultrasonic waves based on a driving signal that is supplied by a transceiving unit 11 described later included in the apparatus main unit 10. Moreover, the transducers included in the ultrasound probe 1 receive a reflected wave from a subject P and convert into an electric signal. Furthermore, the ultrasound probe 1 includes a matching layer that is provided for the transducer, a backing material to prevent propagation of an ultrasonic wave to a backward direction from the transducer, and the like.

When ultrasonic waves are transmitted to the subject P from the ultrasound probe 1, the ultrasonic waves are sequentially reflected on a discontinuous surface of an acoustic impedance in a tissue of the subject P, and received by the transducers included in the ultrasound probe 1 as reflected wave signals. The amplitude of the received reflected wave signals is dependent on a difference in the acoustic impedance on the discontinuous surface on which the ultrasonic waves are reflected. Reflected wave signals when transmitted ultrasonic wave pulses are reflected on a surface of a moving bloodstream, a cardiac wall, and the like have frequency shifts dependent on a velocity component of a moving body relative to a direction of transmission of ultrasonic waves by the Doppler effect.

The ultrasound probe 1 is arranged detachably to the apparatus main unit 10. When scanning (two-dimensional scanning) of a two-dimensional region of the subject P is performed, an operator connects, for example, a 1D array probe in which multiple piezoelectric transducers are arranged in a single row to the apparatus main unit 10, as the ultrasound probe 1. The 1D array probe is a linear ultrasound probe, a convex ultrasound probe, a sector ultrasound probe, or the like. Furthermore, when scanning (three-dimensional scanning) of a three-dimensional region inside the subject P is performed, an operator connects, for example, a mechanical 4D probe or a 2D array probe to the apparatus main unit 10, as the ultrasound probe 1. The mechanical 4D probe is capable of two-dimensional scanning using multiple piezoelectric transducers that are arranged in a single row as 1D array probes, and is capable of three-dimensional scanning by swinging the piezoelectric transducers at a predetermined angle (swing angle). Moreover, the 2D array probe is capable of three-dimensional scanning by piezoelectric transducers that are arranged in a matrix, and is capable of two-dimensional scanning by transmitting ultrasonic waves in a converged manner.

The input device 3 includes an input unit such as a mouse, a keyboard, a button, a panel switch, a touch command screen, a foot switch, a track ball, and a joy stick, and accepts a request for various kinds of settings from an operator of the ultrasonography apparatus, an transfers the accepted request for various kinds of settings to the apparatus main unit 10.

The monitor 2 displays, for example, a graphical user interface (GUI) for an operator of the ultrasonography apparatus to input a request for various kinds of setting by using the input device 3, or displays ultrasonic image data generated in the apparatus main unit 10, and the like.

The apparatus main unit 10 includes an apparatus that generates ultrasonic image data based on a reflected wave signal received by the ultrasound probe 1. The apparatus main unit 10 shown in FIG. 1 includes an apparatus that can generate two-dimensional ultrasonic image data based on reflected wave data corresponding to a two-dimensional region of the subject P received by the ultrasound probe 1. Furthermore, the apparatus main unit 10 shown in FIG. 1 includes an apparatus that can generate three-dimensional ultrasonic image data based on reflected wave data corresponding to a three-dimensional region of the subject P received by the ultrasound probe 1.

The apparatus main unit 10 includes the transceiving unit 11, a B-mode processing unit 12, a Doppler processing unit 13, an image generating unit 14, a data processing unit 15, an image memory 16, an internal storage unit 17, and a control unit 18 as shown in FIG. 1.

The transceiving unit 11 includes a transmission beam former that controls the transmission directivity in transmission of ultrasonic waves. For example, the transceiving unit 11 includes a transmitting unit 111 that has a rate pulse generator 111a, a transmission delaying unit 111b, a transmission pulser 111c, and the like, and provides the ultrasound probe 1 with a driving signal. The rate pulse generator 111a generates rate pulses to form transmission ultrasonic waves repeatedly at a predetermined rate frequency (pulse repetition frequency (PRF)). The rate pulse applies a voltage to the transmission pulser 111c in a state in which a transmission delay time is multiplied therewith by passing through the transmission delaying unit 111b. That is, the transmission delaying unit 111b gives a transmission delay time that is required to converge ultrasonic waves generated by the ultrasound probe 1 into a beam form and to determine the transmission directivity to each rate pulse generated by the rate pulse generator 111a. The transmission pulser 111c applies a driving signal (driving pulse) to the ultrasound probe 1 at timing based on the rate pulse. The state in which the transmission delay time is multiplied include a state in which the transmission delay time is "0".

The driving pulse is transferred to the transducer inside the ultrasound probe 1 through a cable from the transmission pulser, and then converted into a mechanical vibration from an electrical signal by the transducer. The ultrasonic waves generated by this mechanical vibration are transmitted into the inside of a living body. Ultrasonic waves that are generated at the respective transducer each having a transmission delay time are converged to be propagated in a predetermined transmission direction. The transmission delaying unit 111b varies transmission delay times to be given to the respective rate pulses, to adjust the transmission direction from a surface of the transducer arbitrarily. The transceiving unit 11 controls the number and a position (transmission aperture) of the transducers to be used to transmit an ultrasonic beam, and a transmission delay time according to a position of each of the transducers structuring the transmission aperture, to give the transmission directivity.

The transceiving unit 11 has a function enabling to change a transmission frequency, a transmission driving voltage, and the like instantaneously to execute a predetermined scan sequence based on an instruction of the control unit 18 described later. Particularly, a change of the transmission driving voltage is achieved by a linear-amplifier transmission circuit that can change the value instantaneously, or a mechanism of electrically switching multiple power supply units.

After reaching the transducer inside the ultrasound probe 1, a reflected wave of an ultrasonic wave transmitted by the ultrasound probe 1 is converted into an electrical signal (reflected wave signal) from mechanical vibration by the transducer. The reflected wave signal is input, through a cable, to the transceiving unit 11 including a reception beam former that controls the reception directivity in ultrasonic wave reception.

For example the transceiving unit 11 includes a receiving unit 112 having a preamplifier 112a, an analog/digital (A/D) converter 112b, a reception delaying unit 112c, an adding unit 112d, and the like, and generates reflected wave data by performing various kinds of processing on a reflected wave signal received by the ultrasound probe 1. The reflected wave data is converted into ultrasonic image data (B-mode image data), for example, by processing of the B-mode processing unit 12 and the image generating unit 14 described later, to be output to the monitor 2.

The preamplifier 112a performs gain correction processing by amplifying a reflected wave signal per channel. The A/D converter 112b performs A/D conversion of the reflected wave signal subjected to the gain correction, thereby converting the reflected wave signal subjected to the gain correction into digital data. The reception delaying unit 112c multiplies the digital data by a reception delay (reception delay time) that is required to determine the reception directivity. That is, by multiplying an output signal of each transducer by the reception delay time by the reception delaying unit 112c, a data string of the signal from the same sample point on the reception scan line is input to the adding unit 112d. The adding unit 112d performs addition processing (phasing addition processing) of the reflected wave signal (digital data) to which the reception delay time is given by the reception delaying unit 112c. That is, the adding unit 112d adds signals from the same sample point received by the respective transducers at the reception aperture. By the addition processing by the adding unit 112d a reflection component from a direction according to the reception directivity of the reflected wave signal is emphasized. A signal output by the adding unit 112d is output to a processing unit in a later stage as reflected wave data (reception signal).

The transceiving unit 11 as the reception beam former controls the number and the position (reception aperture) of a transducer to be used to receive a reflected wave, and the reception delay time according to the position of each of the transducers structuring the reception aperture, thereby giving the reception directivity. Furthermore, the reception delay time is controlled according to a position of a reception focus together with the position of the transducer.

The transceiving unit 11 is capable of performing, for example, the dynamic variable aperture focus (DVAF) method. In case of performing the DVAF method, when receiving a signal that is returned from near, the transceiving unit 11 makes a reception aperture width small to make a reception beam of a short distance thin. Moreover, in case of performing the DVAF method, when receiving a signal that is returned from far, the transceiving unit 11 makes the reception aperture width large according to a distance because as the reception aperture width increases, stronger focus can be applied. The reception aperture width is set based on an "F-number" set in advance. The "F-number" is a value that is defined by a ratio between the depth of a reception focus and the reception aperture width, and is changed, for example, by an operator arbitrarily. When performing the DVAF method, the transceiving unit 11 changes the reception aperture width at each depth position, according to the "F-number". For example, the transceiving unit 11 sets the reception aperture having the reception aperture width that is determined by the reception focus position and the "F-number" such that the reception scan line is in center.

Furthermore, the transceiving unit 11 performs reception apodization. That is, the adding unit 112d performs addition processing after weighting is performed, by an aperture function (apodization function), on signals (signals input in a state in which the reception delay time is multiplied by the reception delaying unit 112c) from the same sample point received by the respective devices (transducers) at the reception aperture that is structured by the devices (transducers) included in the ultrasound probe 1. For example, the control unit 18 described later creates the aperture function and the transceiving unit 11 therefor. The aperture function (reception aperture function) is a function to which a weight is assigned to each position of the transducer. Moreover, the transceiving unit 11 can also perform parallel simultaneous reception in which reflected waves corresponding to respective positions on the reception scan line that are obtained with one ultrasonic wave transmission at a time.

The form of an output signal from the transceiving unit 11 can be a signal including phase information, or can be amplitude information (amplitude signal) subjected to envelope detection processing, and various kinds of forms can be chosen. The signal including phase information is a radio frequency (RF) signal, or an IQ signal that includes an in-phase signal (I-signal) and a quadrature-phase signal (Q-signal) that are extracted from the RF signal.

The transceiving unit 11 transmits, when scanning a two-dimensional region inside the subject P, an ultrasonic beam to scan the two-dimensional region from the ultrasound probe 1. The transceiving unit 11 then generates two-dimensional reflected wave data from two-dimensional reflected wave signal that is received by the ultrasound probe 1. Furthermore, the transceiving unit 11 transmits, when scanning a three-dimensional region inside the subject P, an ultrasonic beam to scan the three-dimensional region from the ultrasound probe 1. The transceiving unit 11 then generates three-dimensional reflected wave data from a three-dimensional reflected wave signal that is received by the ultrasound probe 1.

The B-mode processing unit 12 generates data (B-mode data) in which a signal intensity (amplitude intensity) is expressed by the intensity of brightness for each sample point, by performing logarithm amplification, the envelope detection processing, logarithm compression, and the like on the reflected wave data output by the transceiving unit 11.

The Doppler processing unit 13 generates data (Doppler data) in which movement information of a moving body (blood stream and tissue, a contrast-agent echo component, and the like) is extracted based on the Doppler effect, by performing frequency analysis on the reflected wave data output by the transceiving unit 11. Specifically, the Doppler processing unit 13 generates Doppler data in which an average speed, a dispersion value, a power value, and the like are extracted as the movement information of a moving body for multiple points.

The B-mode processing unit 12 and the Doppler processing unit 13 are capable of processing both two-dimensional reflected wave data and three-dimensional reflected wave data. The ultrasonography apparatus shown in FIG. 1 can perform harmonic imaging such as contrast harmonic imaging (CHI) and tissue harmonic imaging (THI). The harmonic imaging is an imaging method using that a harmonic component of a frequency of transmission ultrasonic waves returns from a living body. For example, the contrast harmonic imaging is a method of acquiring an image indicating a region in which blood and the like are flowing by extracting harmonic components that are generated at minute bubbles included in an ultrasonic contrast agent, and by converting the extracted harmonic components into an image. Furthermore, for example, the tissue harmonic imaging is a method of acquiring an image having small influence of side lobes by extracting harmonic components included in a reflected wave signal, and by converting the extracted harmonic components into an image.

For example, in the harmonic imaging, imaging methods called an amplitude modulation (AM) method, a phase modulation (PM) method, and an AMPM method in which the AM method and the PM method are combined are performed. In the AM method, the PM method, and the AMPM method, transmission of ultrasonic waves having various amplitudes and phases is performed more than one time to the same scan line. Thus, the transceiving unit 11 generates more than one piece of reflected wave data (reception signal) for each scan line. The transceiving unit 11 extracts harmonic components by performing addition/subtraction processing according to a modulation method on the multiple pieces of the reflected wave data of each scan line. Subsequently, the B-mode processing unit 12 performs the envelope detection processing and the like on the reflected wave data (reception signal) of the harmonic components to generate B-mode data.

For example, when the PM method is performed, the transceiving unit 11 transmits ultrasonic waves of the same amplitude for which the phase polarity is reversed, for example, as (−1, 1) twice for each scan line by a scan sequence specified by the control unit 18. The transceiving unit 11 then generates a reception signal by transmission of "−1" and a reception signal by transmission of "1". The transceiving unit 11 adds these two reception signals. Thus, a signal from which a basic wave component is removed and in which a secondary harmonic component mainly remains is generated. The B-mode processing unit 12 performs the envelope detection processing and the like on this signal, to generate B-mode data of THI or B-mode data of CHI.

Furthermore, in THI, a method of performing visualization using a secondary harmonic component and a difference tone component included in the reception signal has been in practical use. In a visualization method using a difference tone component, for example, a transmission ultrasonic wave having a composite waveform in which a first base wave the center frequency of which is "f1", and a second base wave the center frequency of which is "f2" that is larger than "f1" are combined is transmitted from the ultrasound probe 1. This composite waveform is a waveform in which a waveform of the first base wave and a waveform of the second base wave are combined for which phases thereof are adjusted so that a difference tone component having the same polarity as the secondary harmonic component is generated. The transceiving unit 11 transmits the transmission ultrasonic wave of the composite waveform, for example, two times, while reversing the phase. In such a case, the transceiving unit 11 generates two reception signals that respectively correspond to the two times of transmission. The transceiving unit 11 then adds these two reception signals. Thus, a signal from which the base wave component is removed, and in which the difference tone component and the secondary harmonic component mainly remain is generated. The B-mode processing unit 12 performs the envelope detection processing and the like on this signal, to generate B-mode data of THI. The addition/subtraction processing of multiple pieces of the reflected wave data (reception signals) for each scan line can be performed by the B-mode processing unit 12.

The image generating unit 14 generates ultrasonic image data from the data that is generated by the B-mode processing unit 12 and the Doppler processing unit 13. That is, the image generating unit 14 generates two-dimensional B-mode image data in which the intensity of a reflected wave is expressed by brightness, from two-dimensional B-mode data generated by the B-mode processing unit 12. Furthermore, the image generating unit 14 generates two-dimensional Doppler image data that indicates moving body information, from two-dimensional Doppler data generated by the Doppler processing unit 13. The two-dimensional Doppler image data is speed image data, dispersion image data, power image data, or image data in which these are combined.

Generally, the image generating unit 14 converts (scan converts) a scan-line signal string of ultrasonic scanning into a scan-line signal string of a video format represented by television and the like, to generate ultrasonic image data for display. For example, the image generating unit 14 generates the ultrasonic image data for display by performing coordinate conversion according to a scanning form of an ultrasonic wave by the ultrasound probe 1. Moreover, the image generating unit 14 performs image processing (smoothing) to regenerate a brightness average-value image, image processing (edge enhancement) using a differential filter in an image, and the like as various kinds of image processing other than the scan conversion, by using image frames after scan conversion, for example. Furthermore, the image generating unit 14 composites character information of various kinds of parameters, scales, body marks, and the like.

That is, the B-mode data and the Doppler data are the ultrasonic image data before performing the scan conversion processing, and data generated by the image generating unit 14 is ultrasonic image data for display after the scan conversion processing is performed. The B-mode data and the Doppler data are also referred to as raw data.

Moreover, the image generating unit 14 generates three-dimensional B-mode image data by performing coordinate conversion on three-dimensional B-mode data generated by the B-mode processing unit 12. Furthermore, the image generating unit 14 generates three-dimensional Doppler image data by performing coordinate conversion on three-dimensional Doppler data generated by the Doppler processing unit 13. That is, the image generating unit 14 generates the "three-dimensional B-mode image data and the three-dimensional Doppler image data" as "three-dimensional ultrasonic image data (volume data)". The image generating unit 14 then performs various kinds of rendering processing on the volume data to generate various kinds of two-dimensional image data to display the volume data on the monitor 2.

The data processing unit 15 is a processing unit that performs various kinds of processing on data generated in the apparatus main unit 10, and as shown in FIG. 1, includes an acquiring unit 151, a calculating unit 152, and a multiplying unit 153. For example, data processed by the data processing unit 15 includes a signal obtained by performing phasing addition on signals including phase information (an IQ signal or an RF signal), an amplitude signal obtained by performing phase detection on this signal, and an image signal obtained by performing logarithm compression on this amplitude signal. The data processing unit 15 according to the first embodiment is described in detail later.

The image memory 16 is a memory that stores image data generated by the image generating unit 14. Moreover, the image memory 16 can also store data generated by the B-mode processing unit 12 and the Doppler processing unit 13. B-mode data and Doppler data stored in the image memory 16 can be retrieved, for example, by an operator after diagnosis, and are to be ultrasonic image data for display through the image generating unit 14. Furthermore, the image memory 16 can also store data output by the transceiving unit 11, or data output by the data processing unit 15.

The internal storage unit 17 stores a control program to perform ultrasonic wave transmission/reception, image processing, and display processing, diagnosis information (for example, patient identification (ID), observations of a doctor, and the like), or various kinds of data such as a diagnosis protocol and various kinds of body marks. Moreover, the internal storage unit 17 is also used to archive data stored in the image memory 16, and the like as necessary.

The control unit 18 controls overall processing of the ultrasonography apparatus. Specifically, the control unit 18 controls processing of the transceiving unit 11, the B-mode processing unit 12, the Doppler processing unit 13, the image generating unit 14, and the data processing unit 15 based on various kinds of setting requests input by an operator through the input device 3, or various kinds of control programs and data read from the internal storage unit 17. Furthermore, the control unit 18 controls to display ultrasonic image data for display that is stored in the image memory 16 on the monitor 2.

As above, the entire configuration of the ultrasonography apparatus according to the first embodiment has been explained. With such a configuration, generation and display of ultrasonic image data (for example, B-mode image data) are performed.

As a method of reducing reverberation echoes that interfere diagnosis in a B-mode image, various methods are conceivable. These methods are a method of reducing reverberation echoes by so-called spatial compounding processing. FIG. 2, FIGS. 3A and 3B, and FIG. 4 are diagrams for explaining a conceivable method to reduce reverberation echoes.

One example of such methods is a method in which multiple pieces of B-mode image data with various deflection angles in ultrasonic wave transmission/reception are compounded by signal averaging. Moreover, by applying this method, a method is conceivable in which a degree and a position of a reverberation echo component are estimated from B-mode image data with various deflection angles, and weight at signal averaging is adaptively controlled from an estimation result. These methods are methods of compounding multiple pieces of ultrasonic image data with various deflection angles that are generated by ultrasonic scanning in which deflection angles in ultrasonic wave transmission/ reception are varied among frames.

The deflection angle in a direction perpendicular to a direction of arrangement of the transducers is defined herein as "0 degrees". The deflection angle "0 degrees" is a direction of normal ultrasonic wave transmission/reception that is performed without deflection. Furthermore, a deflection angle in a leftward direction relative to the direction of arrangement of the transducers is defined as a "positive angle", and a deflection angle in a rightward direction relative to the direction of arrangement of the transducers is defined as a "negative angle".

Figure 2:
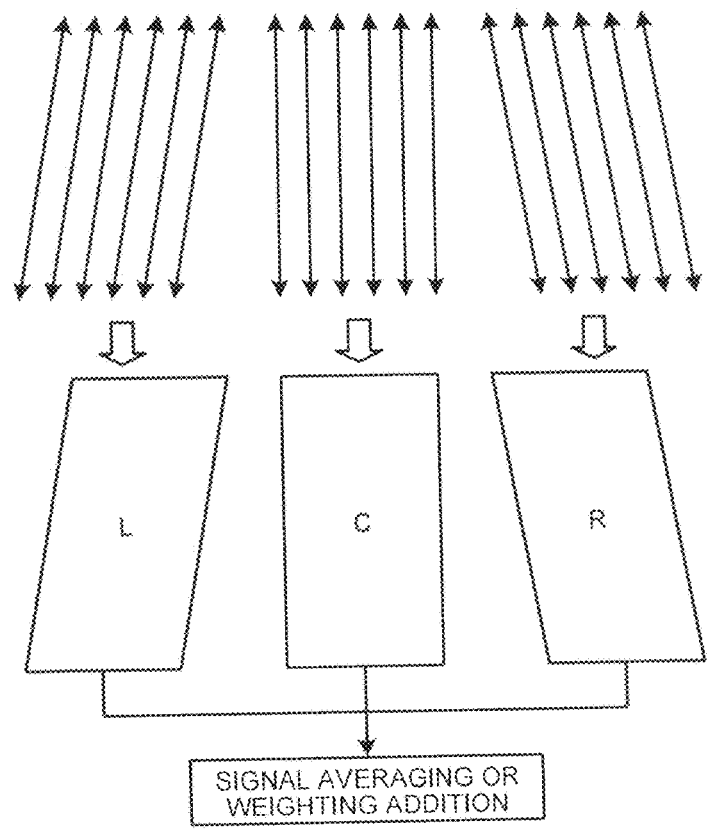
FIG. 2 is a diagram (1) for explaining a conceivable method to reduce reverberation echoes.

When the definition is applied, "C" shown in FIG. 2 is B-mode image data that is generated by performing ultrasonic wave transmission/reception with the deflection angle of "0 degrees" is performed. Moreover, "L" shown in FIG. 2 is B-mode image data that is generated by performing ultrasonic wave transmission/reception deflected leftward with the deflection angle of "+θ degrees" is performed. Furthermore, "R" shown in FIG. 2 is B-mode image data that is generated by performing ultrasonic wave transmission/reception deflected rightward with the deflection angle of "−θ degrees" is performed. Hereinafter, "L" shown in FIG. 2 is described as left-deflected image data L. Moreover, hereinafter, "R" shown in FIG. 2 is described as right-deflected image data R. Furthermore, hereinafter, "C" shown in FIG. 2 that is to be a center image between the left-deflected image data L and the right-deflected image data R is described as center image data C.

In the method shown in FIG. 2, image data in which the center image data C, the left-deflected image data L, and the right-deflected image data R are subjected to signal averaging is output. Alternatively, in the method shown in FIG. 2, a degree and a position of a reverberation echo component are estimated from the center image data C, the left-deflected image data L, and the right-deflected image data R. Furthermore, in the method shown in FIG. 2, weight at signal averaging is calculated from an estimation result, and weighting addition is performed on the center image data C, the left-deflected image data L, and the right-deflected image data R, to output image data.

Figure 3A:
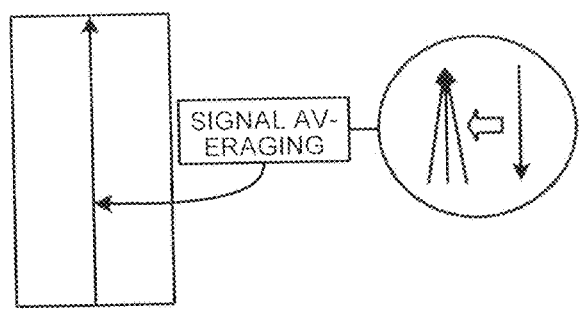
FIGS. 3A and 3B are diagrams (2) for explaining a conceivable method to reduce reverberation echoes.
Figure 3B:
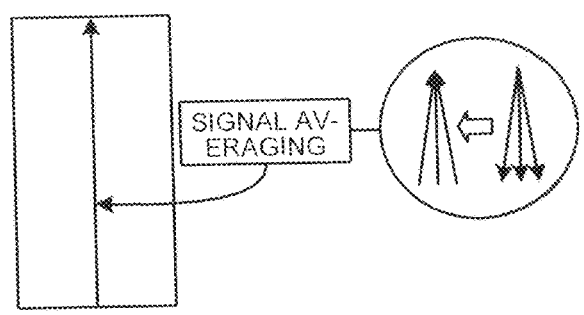

Moreover, two methods exemplified in FIG. 3A and FIG. 3B are conceivable as a general spatial compounding processing to reduce reverberation echoes, other than the above "method of compounding multiple images with various deflection angles". The method shown in FIG. 3A is a method in which signal averaging is performed on multiple reception signal groups with various deflection angles that are obtained simultaneously by parallel simultaneous reception for the same transmission beam when a reception signal of a single scan line is acquired. In the method exemplified in FIG. 3A, fixing the transmission aperture and the reception aperture, reflected waves with reception deflection angles (for example, 0 degrees, +θ degrees, and −θ degrees) from three directions are acquired by parallel simultaneous reception for a transmission ultrasonic wave at one scan line, thereby acquiring simultaneous reception signals based on a reception scan line from three directions. In the method shown in FIG. 3A, by signal averaging the simultaneous reception signals based on the reception scan line in three directions, one reception signal with the reception deflection angle of "0 degrees" is acquired. The processing is performed for all of scan lines in a frame.

On the other hand, the method exemplified in FIG. 3B is a method in which reception signals from corresponding directions are acquired while varying the deflection angles of transmission among rates when a reception signal of a single scan line is acquired, and the reception signals at these multiple rates are signal averaged. FIG. 3B indicates reception signals based on the reception scan line in three directions generated by performing ultrasonic wave transmission/ reception with transmission/reception deflection angles (0 degrees, +θ degrees, and −θ degrees) in three directions, fixing the transmission aperture and the reception aperture. In the method shown in FIG. 3B, by signal averaging the reception signals based on the reception scan line in three directions, one reception signal with the reception deflection angle "0 degrees" is acquired. The processing is performed for all of scan lines in a frame.

These three kinds of methods enable to improve a signal-to-noise ratio in an image, by maintaining a signal component (for example, a signal component originated in a tissue) having relatively small intensity variation even if inclined, by using a fact that a position at which a reverberation echo (noise) appears varies according to a deflection angle when the deflection angle of an ultrasonic beam to the subject P is changed (when the ultrasonic beam is inclined) by compounding processing. For the change of the deflection angle at transmission, a control by transmission delay patterns is suitable. Moreover, as for the change of the deflection angle at reception, there is a case in which a control of changing the reception delay pattern is performed, and a case in which a control of unbalancing reception aperture distribution (apodization) on right and left is performed.

The method exemplified in FIG. 3A is more in real time because parallel simultaneous reception is applied. However, because the deflection angles are varied between transmission and reception in the method exemplified in FIG. 3A, to obtain reverberation reducing effect, it is necessary to make the deflection angle large. However, in the method exemplified in FIG. 3A, if the deflection angles between transmission and reception are large, the sensitivity is degraded.

On the other hand, in the method exemplified in FIG. 3B, the deflection angles can be the same between transmission and reception, and therefore, the deflection angle can be set large while suppressing degradation of the sensitivity, and the reverberation reducing effect higher than the method exemplified in FIG. 3A can be obtained. However, the method exemplified in FIG. 3B requires a rate sequence, and the frame rate decreases.

Figure 4:
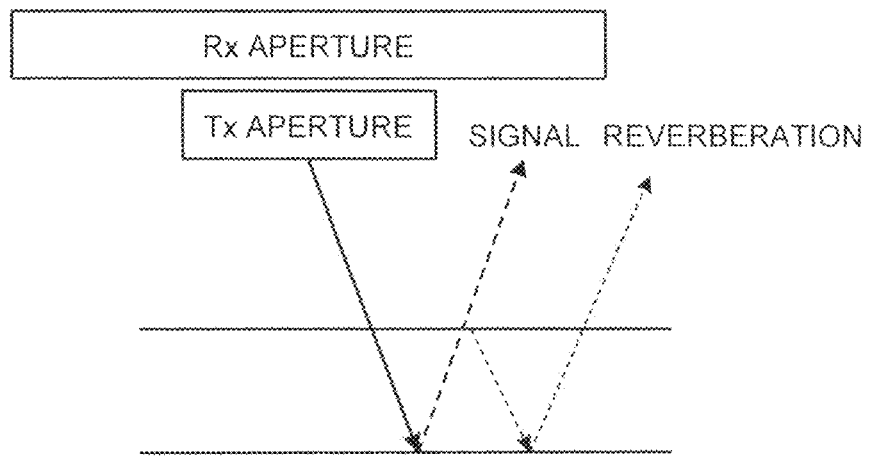
FIG. 4 is a diagram (3) for explaining a conceivable method to reduce reverberation echoes.

On the other hand, in the method exemplified in FIG. 2, because the deflection angle is changed per frame (per image), the deflection angle between transmission and reception can be the same, thereby suppressing degradation of the sensitivity, and decrease of the frame rate is small. That is, when the deflection angle is change per frame, the transmission/reception deflection angle can be changed by the control of the transmission/reception delay pattern, fixing the reception aperture size (reception aperture width), and therefore, a relatively large deflection angle can be obtained while maintaining the sensitivity. If the deflection angle is large, for example, as shown in FIG. 4, among reflected waves of ultrasonic waves transmitted from the transmission aperture (Tx Aperture) in an inclined manner, while a true signal component (Signal) of single reflection is received by the reception aperture (Rx Aperture), a reverberation component (Reverberation) that repeats reflection travels outside the reception aperture (Rx Aperture) and is not received. As described, in the method in which the deflection angle is change per frame, by making the deflection angle large, the reverberation reducing effect is enhanced. Therefore, in the method exemplified in FIG. 2, it is possible to achieve both the multiplex reducing effect and maintenance the frame rate and the sensitivity to some extent.

However, in the method in which the deflection angle is changed per frame, the influence of reduced amplitude when a deflection angle is increased cannot be avoided due to the constraint of element factors. Particularly, at a device at an end portion of the aperture, transmission and reception are performed at relatively large deflection angles, and therefore, the degree of reduction of amplitude is large. This corresponds to reduction in an effective aperture width. That is, in deflected image data (for example, the left-deflected image data L and the right-deflected image data R), the lateral resolution is degraded compared to image data with the deflection angle of "0 degrees" (the center image data C). Furthermore, in deflected image, the sensitivity (S/N ratio) to the center image data C is also degraded. Therefore, in an output image that is obtained by compounding multiple images with various deflection angles, the lateral resolution and the sensitivity are degraded compared to the image not deflected (for example, the center image data C).

Figure 5:
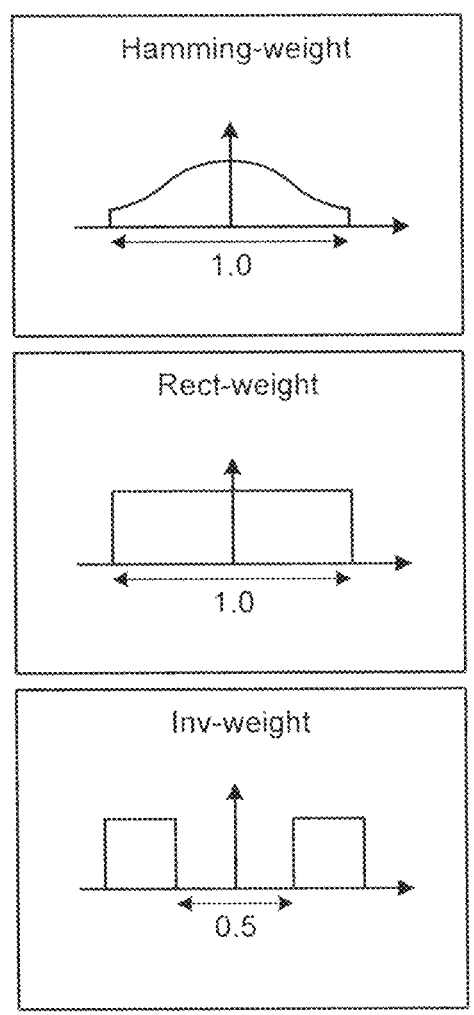
FIG. 5 is a diagram (1) for explaining an action of an aperture function.
Figure 6:
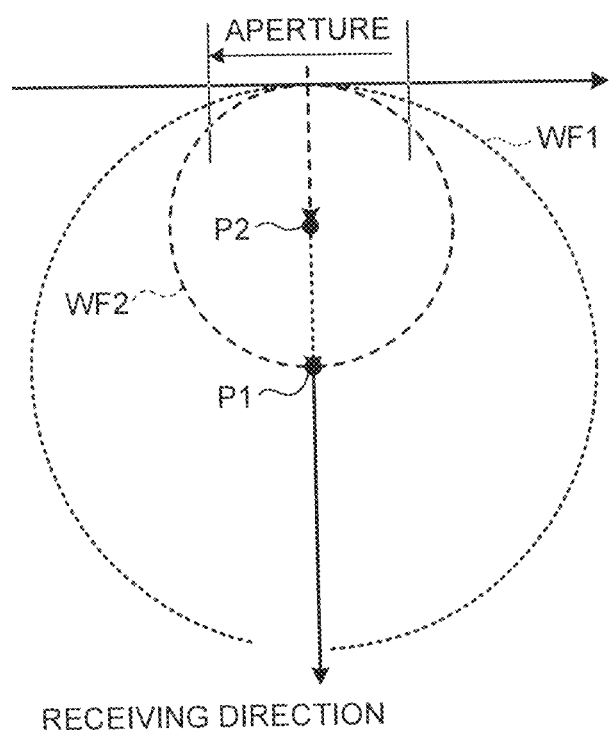
FIG. 6 is a diagram (2) for explaining an action of an aperture function.
Figure 7:
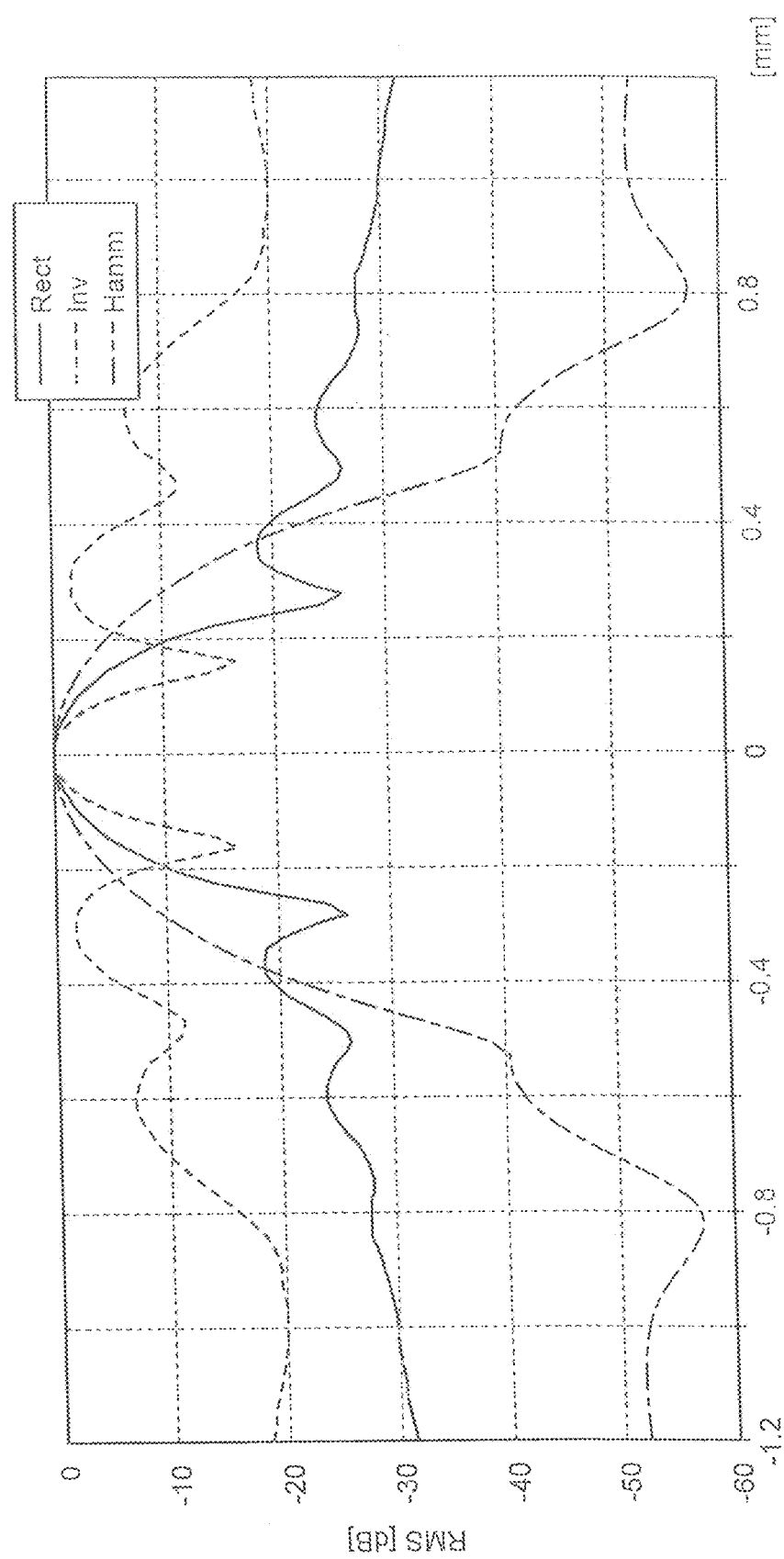
FIG. 7 is a diagram (3) for explaining an action of an aperture function.

Moreover, a method of effectively reducing specular reverberation by reception apodization is conceivable other than the spatial compounding method explained using FIG. 2 to FIG. 4. In this method, reception apodization is performed to remove reverberation components as much as possible. An aperture function used in this reception apodization is explained using FIG. 5 to FIG. 7, together with an aperture function used in the reception apodization indicated below. FIG. 5 to FIG. 7 are diagrams for explaining an action of an aperture function. In the reception apodization explained herein, to acquire a signal component with low side lobe, for example, an aperture function to weight by a "hamming window" is used (refer to "Hamming-weight" in an upper diagram in FIG. 5). Alternatively, in this reception apodization, to acquire a signal component with high lateral resolution, for example, an aperture function to weight by a "rectangular window" is used (refer to "Rect-weight" in an upper diagram in FIG. 5). In FIG. 5 a reception aperture width is indicated as "1.0".

Furthermore, in the above method, for the purpose of removing reverberation components, an aperture function that makes a weight of a center portion of the reception aperture substantially "0" is used. For example, in this method, an aperture function in which a half (0.5) of the reception aperture width is "0" at an aperture center portion as indicated in "Inv-weight" in a lower diagram in FIG. 5.

As shown in FIG. 5, the aperture function using the hamming window is an aperture function in which a weight of a device in the center portion is larger than a weight of a device at the end portion of the reception aperture, and the aperture function using the rectangular window is an aperture function in which weights of the respective devices at the reception aperture are uniform. On the other hand, the aperture function of "Inv-weight" is an aperture function in which a weight of a device in the center portion is smaller than a weight of a device at the end portion of the reception aperture. In the following, based on the difference in a form of weighting patterns, the reception apodization based on the weighting such as the above "Hamming-weight" and the "Rect-weight" is described as "normal apodization", and the reception apodization based on the weighting such as the above "Inv-weight" is described as "inverse apodization" in some cases. Moreover, in the following, the aperture function used in the "normal apodization" is described as a "normal aperture function", and the aperture function used in the "inverse apodization" is described as an "inverse aperture function" in some cases.

The fact that the inverse aperture function used in the above method is effective for reducing reverberation is explained using FIG. 6. "Aperture" shown in FIG. 6 is the reception aperture. In FIG. 6, the width of the reception aperture is indicated by a bidirectional arrow. FIG. 6 indicates positional relation between the reception aperture and a scan line direction (refer to "Receiving direction" in the figure) when a reflected wave is received from a reflection source that is positioned right under (in front) the reception aperture in linear scanning or sector scanning. Furthermore, P1 shown in FIG. 6 is a reflection source positioned in the scan line direction, and P2 shown in FIG. 6 is a reflection source positioned closer to the reception aperture than the reflection source P1. In FIG. 6, a distance between the reflection source P1 and the reception aperture is twice as long as a distance between the reflection source P2 and the reception aperture.

Suppose a reflected wave that has been reflected on the reflection source P2 is reflected once on a surface of the ultrasound probe 1 to re-enter a living body, and the reflected wave re-entered is reflected on the reflection source P2 to be received as a reflected wave signal. A wavefront of the reflected wave reflected from the reflection source P2 in this single reverberation is observed as a wavefront at the same time as a reflected wave that is reflected on the reflection source P1. Accordingly, a reflection echo component from P1 and a reverberation echo component by P2 are superimposed to be received, and therefore, it is impossible to distinguish the two echo components. However, shapes of the wavefronts of the two on the aperture are different. This is shown in FIG. 6. In FIG. 6, a signal wavefront from the normal reflection source P2 is indicated by "WF2", and a reverberation wavefront from the reflection source P1 of the single reverberation is indicated by "WF1".

By reception delay processing using a position near the reflection source P2 as a reception focus, for the signal wavefront WF2, phases match at all of the devices structuring the reception aperture. On the other hand, due to the difference between the depth in which a signal component from front is finally reflected and the depth in which a reverberation component from front is finally reflected, even if the reception delay processing is performed, for the reverberation wavefront WF1, phases match only at devices in a limited range in the center portion of the reception aperture. The inverse apodization is a method of reducing reverberation components using such a phenomenon, for example, by making the weight of a signal component entering the center portion of the reception aperture "0" applying the inverse aperture function (the inverse aperture function in which the center portion is zero) indicated in the lower diagram in FIG. 5.

However, in the inverse apodization, although reverberation components can be reduced, a side lobe component (particularly, a 1st side-lobe component) is high, and a main beam is multiplexed, casing degradation of the image quality. This is explained using FIG. 7. FIG. 7 indicates a result of calculation of an acoustic field profile (received acoustic-field profile) near the focus that is acquired by the three aperture functions shown in FIG. 5. The horizontal axis in FIG. 7 indicates a position in an azimuth direction (unit: millimeter (mm)), and the vertical axis in FIG. 7 indicates a root mean square (RMS, unit: decibel (dB)) of an acoustic field near the focus. RMS values corresponding to the three aperture functions are normalized at peak values. It has been known that the acoustic field profile near the focus is given by the Fourier transform of the aperture function. For example, the Fourier transform of the rectangular aperture function is a sinc function.

As shown in FIG. 7, when an acoustic field profile of the normal aperture function of the hamming window and an acoustic field profile of the normal aperture function of the rectangular window are compared, in the normal aperture function of the hamming window, the side lobe component can be maintained low, although the beam width of a main lobe component is wide. On the other hand, as shown in FIG. 7, with the inverse aperture function in which the center portion is zero, although the beam width of the main lobe component is narrower than that of the normal aperture function of the rectangular window, the 1st side-lobe component significantly increases. The acoustic field profile in FIG. 7 indicates how a point being a reflection source is drawn in an image. FIG. 7 indicates that the lateral resolution of B-mode image data that is obtained by the inverse apodization using the inverse aperture function in which the center portion is zero is lower than that in the normal apodization.

To ease degradation of the image quality in the inverse apodization, aperture compounding processing in which the normal apodization and the inverse apodization are combined can also be performed. However, in the aperture compounding processing with a reception signal acquired by the normal aperture function and a reception signal acquired by the inverse aperture function, the lateral resolution of an image after compounding is degraded by the influence of the side lobe component (particularly, the 1st side-lobe component) that becomes high in the inverse apodization. Moreover, the position of the 1st side-lobe component that is generated in the inverse apodization corresponds to the position of the main lobe component in the normal apodization as shown in FIG. 7, and therefore, a moire (striped pattern artifact) occurs in an image by phase interference of the both. Furthermore, in general transmission/reception acoustic-field generation, side lobe components are suppressed by narrowing a relatively wide transmission beam with a narrow reception beam. However, in the inverse apodization, as shown in FIG. 7, not only the 1st side-lobe component but also a 2nd side-lobe component and the like are also high. From this fact, if a wide transmission beam is used, a side lobe component in the inverse apodization becomes further higher compared to a case in the normal apodization. As a result, when the general transmission/reception acoustic-field generation in which a wide transmission beam is narrowed by a narrow reception beam is performed, in an image after the aperture compounding, these surrounding noises are folded in, and the image quality is tend to be degraded.

As described, in the above method of reducing reverberation, it can be impossible to achieve both reduction of reverberation and maintenance of the lateral resolution and the sensitivity.

Therefore, in the ultrasonography apparatus according to the first embodiment, processing by the data processing unit 15 and the control unit 18 shown in FIG. 1 is performed to acquire a high quality image in which reverberation is reduced and the lateral resolution and the sensitivity are maintained.

First, the acquiring unit 151 according to the first embodiment assigns various kinds of weights to reflected wave signals that are generated at the reception aperture structured with devices included in the ultrasound probe 1, and to which delays according to a position in the reception aperture are given, and acquires reception signals that are generated by adding the weighted reflected wave signals for each kind of weight. The assignment of various kinds weights is performed by the adding unit 112d using various kinds of aperture functions. That is, in the first embodiment, by aperture functions having different patterns of weights set according to a position of each transducer that structures the reception aperture, reception signals are generated at each scan line. Specifically, in the first embodiment, the normal aperture function and the inverse aperture function described above are used as different kinds of aperture functions.

The normal aperture function is an aperture function to acquire a signal component, and is the "aperture function of the hamming window" in which a weight of a device in the center portion is larger than a weight of a device at the end portion of the reception aperture, and the "aperture function of the rectangular window" in which a weight of each device at the reception aperture is uniform. Alternatively, the normal aperture function may be the "aperture function of the hamming window" or an "aperture function of a flat-top window".

Moreover, the inverse aperture function is an aperture function to reduce reverberation components. The inverse aperture function is an aperture function in which a weight of a "range including a reception position at which a reverberation component is received at the reception aperture" is smaller than a weight of an outside of the range. By using the inverse function that is designed based on such a concept, a reception signal in which information of a signal received in the range of the reception aperture is lowered more than a signal received outside the range can be output as a reception signal of the reception aperture.

For example, when "a boundary formed with objects causing reverberation and a probe surface are parallel", and "a direction of transmission/reception of an ultrasonic wave is perpendicular to the probe surface", a position (reception position) at which a reverberation component is received at the reception aperture is a "position in the center of the reception aperture". When the reception position is fixed to the center of the reception aperture, the inverse aperture function is an aperture function in which a weight of a device in the center portion is smaller than a weight of a device at the end portion of the reception aperture. The "inverse aperture function in which the center portion is zero" is one example of the inverse aperture function for which the reception position is fixed to the "position in the center of the reception aperture". Furthermore, the "inverse aperture function in which the center portion is zero" is one example in which the "range including a reception position" corresponds to a "range having a reception position (center of the reception aperture) in center", and the width of the "range including a reception position" is half of the reception aperture width.

The range used to create the inverse aperture function can be changed by the control unit 18 or by an operator arbitrarily. Furthermore, the position of the "reception position" in the "range" is not limited to the center of the "range", and can be changed by the control unit 18 or by an operator arbitrarily, for example, to the center of gravity of the "range" or the like. Moreover, the weight of the "range" of the inverse aperture is not limited to be uniformly "0", and as long as the above design concept is satisfied, it can be changed by the control unit 18 or by an operator arbitrarily. For example, the weight pattern in the "range" of the inverse aperture function may be such that a weight of positions at both ends of the range is "1", and a weight of the reception position is "0" sequentially decreasing toward the reception position from the ends.

The reception signal acquired by the acquiring unit 151 according to the first embodiment is a signal obtained by performing phasing addition of signals including phase information, or an amplitude signal obtained by performing phase detection on the signal, or an image signal obtained by performing logarithm compression on the amplitude signal. That is, the first embodiment is applicable to either of a case in which the acquiring unit 151 acquires an IQ signal or an RF signal of each scan line output by the adding unit 112d of the transceiving unit 11, a case in which the acquiring unit 151 acquires an amplitude signal of each scan line subjected to envelope detection is performed by the B-mode processing unit 12, a case in which the acquiring unit 151 acquires an image signal (a brightness value of each sample point) of each scan line output by the B-mode processing unit 12, and a case in which the acquiring unit 151 acquires a image signal (a pixel value of each pixel) of each scan line output by the image generating unit 14. Reception signals per scan line that are acquired by the acquiring unit 151 may also be acquired by parallel simultaneous reception.

The calculating unit 152 according to the first embodiment calculates a coefficient using at least one reception signal among reception signals acquired by the acquiring unit 151. Specifically, the calculating unit 152 calculates a coefficient corresponding to each of positions on the reception scan lines corresponding to the reception signals acquired by the acquiring unit 151 based on a signal value or a pixel value that are a signal value or a pixel value based on at least one reception signal among the reception signals, and that corresponds to each of the positions. The multiplying unit 153 according to the first embodiment acquires output data by multiplying at least one reception signal that is different from the above at least one reception signal used to calculate the coefficient, among the reception signals acquired by the acquiring unit 151 by the coefficient. Specifically, the multiplying unit 153 multiplies a signal value or a pixel value that is based on at least one reception signal that is different from the above at least one reception signal used to calculate the coefficient among the reception signals acquired by the acquiring unit 151, and that corresponds to each of positions on a reception scan line by the coefficient, thereby acquiring the output data. The reception signal that is used to calculate a coefficient distribution by the calculating unit 152 is a reception signal that is generated based on the inverse aperture function. Furthermore, the reception signal that is multiplied by the coefficient distribution by the multiplying unit 153 is a reception signal that is generated based on the normal aperture function. Subsequently, the control unit 18 according to the first embodiment controls to display, on the monitor 2, ultrasonic image data based on the output data from the multiplying unit 153. That is, the image generating unit 14 generates ultrasonic image data based on the output data that is acquired by the multiplying unit 153, and the monitor 2 displays the ultrasonic image data by the control of the control unit 18.

That is, the first embodiment is to acquire output image data for display, by calculating a "weight (coefficient)" from a reception signal with reduced reverberation acquired by the inverse apodization, and by multiplying a reception signal with high spatial resolution and sensitivity acquired by the normal apodization by the calculated "weight (coefficient)".

A specific example of processing performed by the data processing unit 15 and the control unit 18 according to the first embodiment is explained below using FIG. 8 to FIG. 12 and the like. FIG. 8 to FIG. 12 are diagrams for explaining the first embodiment. In the following, a case in which the normal aperture function of the hamming window and the inverse aperture function in which the center portion is zero are used as two kinds of aperture functions, and the acquiring unit 151 acquires B-mode image data that is generated by the normal aperture function of the hamming window and B-mode image data that is generated by the inverse aperture function in which the center portion is zero is explained.

Figure 8:
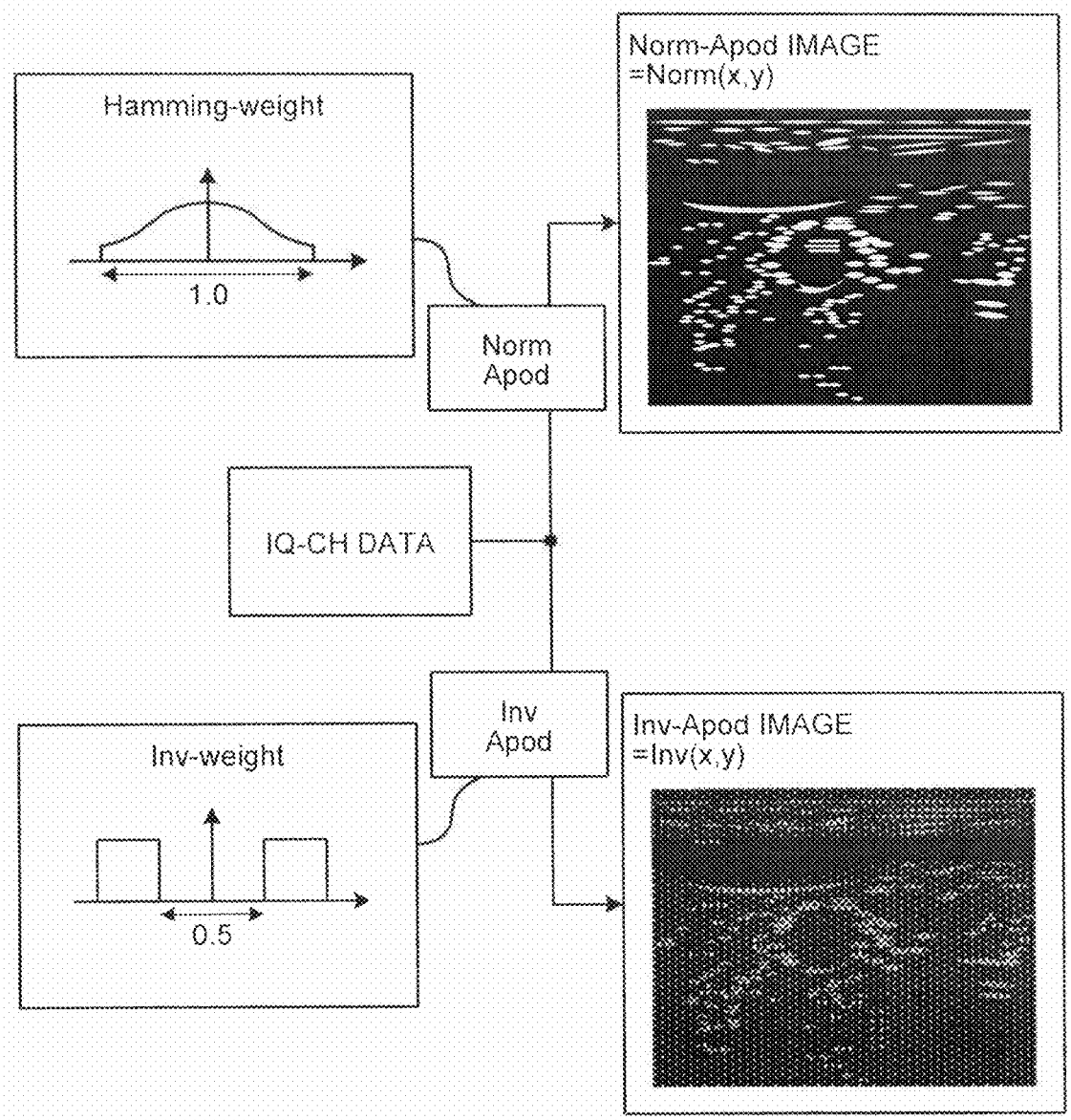
FIG. 8 is a diagram (1) for explaining the first embodiment.

First, by the control of the control unit 18, the transceiving unit 11 performs transmission and reception of an ultrasonic wave at each scan line forming a scanning range. To the adding unit 112d of the transceiving unit 11, a reception signal ("IQ-CH data" shown in FIG. 8) of each cannel to which required delay is given by the reception delaying unit 112c is input as an input signal. While "IQ-CH data" indicates a data string of an IQ signal, the input signal to the adding unit 112d may be a data string of an RF signal. The adding unit 112d separates the input signal "IQ-CH data" into two systems as shown in FIG. 8. The adding unit 112d then performs phasing addition by performing weighting using the normal aperture function of the hamming window as the normal apodization (NormApod) in one system, and performs phasing addition by performing weighting using the inverse aperture function in which the center portion is zero as the inverse apodization (InvApod) in the other system. Reflected wave data (IQ signal) including phase information of each scan line of the two systems output by the adding unit 122d is subjected to detection processing, logarithm compression processing, and the like by the B-mode processing unit 12, and then converted into an image signal for display by the image generating unit 14.

"Norm-Apod image=Norm(x, y)" shown in FIG. 8 indicates B-mode image data as an image signal acquired by the normal apodization. Moreover, "Inv-Apod image=Inv (x, y)" shown in FIG. 8 indicates an image signal of B-mode image data that is acquired by the inverse apodization. "(x, y)" indicates a position of each pixel (each image signal) constituting the B-mode image data. The calculating unit 152 calculates a coefficient for each pixel. That is, the calculating unit 152 calculates a coefficient distribution that indicates respective coefficients of pixels.

Figure 9:
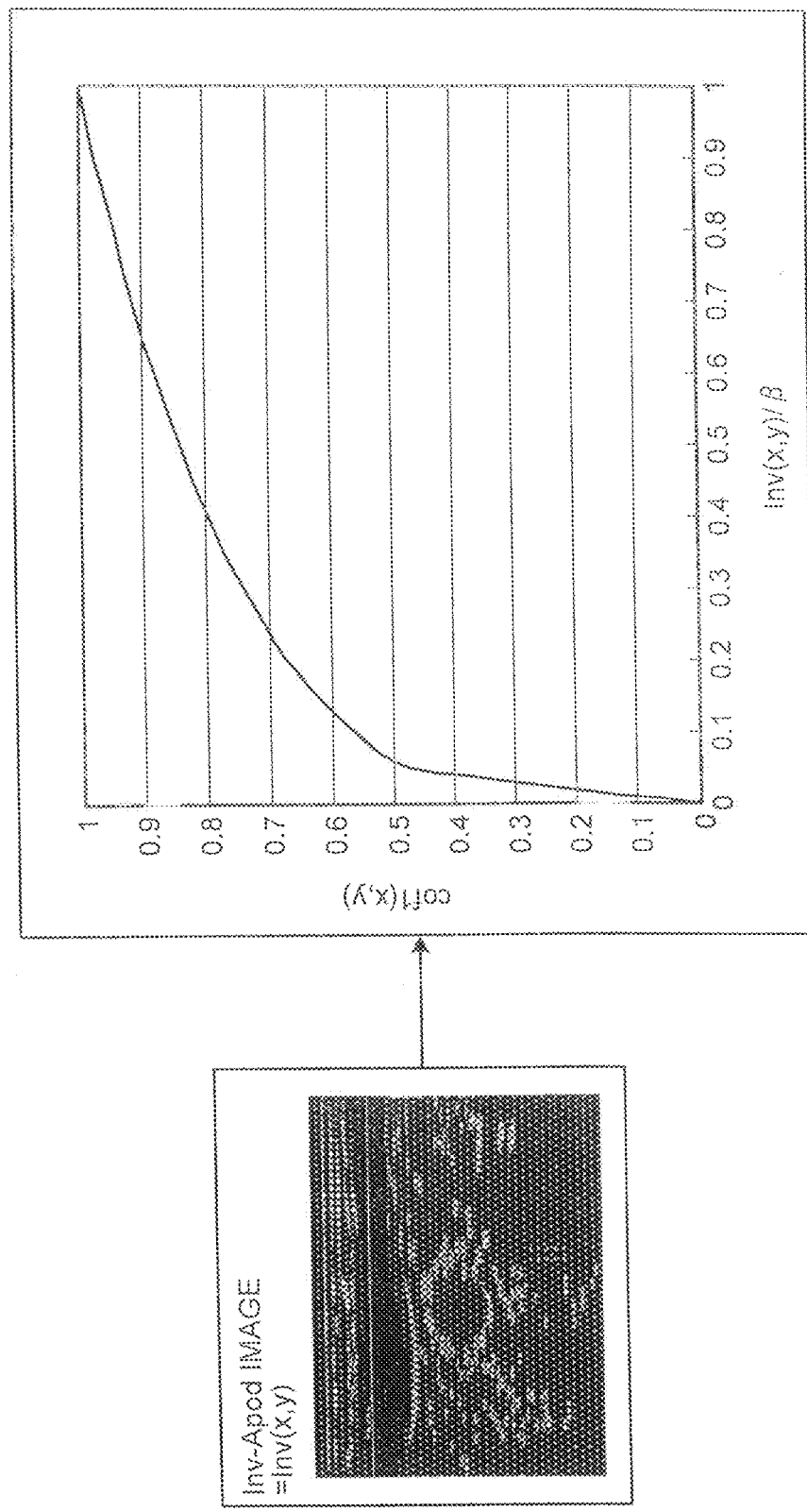
FIG. 9 is a diagram (2) for explaining the first embodiment.

For example, the calculating unit 152 calculates a coefficient distribution "cof1(x, y)" of a weight from "Inv(x, y)" as shown in FIG. 9. Specifically, the calculating unit 152 calculates "cof1(x, y)" by following Equation 1. In Equation 1 below, "cof1(x, y)" is "0.0≤cof1(x, y)≤1.0".

$$\text{cof1}(x,y) = (\text{Inv}(x,y)/\beta)^\alpha \{\text{where cof1}(x,y)=1.0 \text{ when } \text{Inv}(x,y) > \beta)\} \quad (1)$$

In Equation 1 above, it is defined that "cof1(x, y)" is an "α-th power" of a value obtained by dividing Inv(x, y) by "β". Moreover, in Equation 1 above, it is defined that "cof1(x, y)" is "1" when a value obtained by dividing Inv(x, y) by "β" is larger than "1". "α, β" are predetermined values. Specifically, "β" signifies an upper limit level of an output signal, and is set to a level equal to or lower than a maximum value "max" of an image signal. It is preferable that "β" be set to a level of about 70% to 80% of "max". Furthermore, it is preferable that "α" be set to a value of about "¼ to ⅓".

A graph shown in FIG. 9 is a graph in which output values "cof1(x, y)" that are calculated from input values "Inv(x, y)/β" are plotted. An advantage of calculating a coefficient distribution using a function including an arithmetic processing in which the calculating unit 152 exponentiates an input value as in Equation 1 is explained later.

The multiplying unit 153 multiplies "Norm(x, y)" by the coefficient distribution "cof1(x, y)", and outputs output image data "Multiply=O_N(x, y)". Specifically, the multiplying unit 153 performs arithmetic processing of Equation 2 below.

$$O\_N(x,y) = \text{Norm}(x,y) * \text{cof1}(x,y) \quad (2)$$

The control unit 18 controls to display the output image data "Multiply=O_N(x, y)" on the monitor 2 as B-mode image data subjected to correction processing. In the above example, because the image signal generated by the image generating unit 14 is used, output data of the multiplying unit 153 is to be ultrasonic image data for display. When a signal (an IQ signal or an RF signal) generated by the adding unit 112d is used, output data of the multiplying unit 153 is subjected by processing by the B-mode processing unit 12 and the image generating unit 14, to be ultrasonic image data for display. Moreover, when an amplitude signal is used, the multiplying unit 153 is subjected to logarithm compression processing by the B-mode processing unit 12 and scan convert processing by the image generating unit 14, and the like, to be ultrasonic image data for display. Furthermore, when an output signal of the B-mode processing unit 12 is used, output data of the multiplying unit 153 is subjected to processing by the image generating unit 14, to be ultrasonic image data for display.

For a reception signal in the normal apodization acquired by the acquiring unit 151 in the first embodiment, a signal of a basic wave component that is suitable for imaging with high sensitivity even to a deep portion may be used, or a signal of a tissue harmonic component (a non-linear component of a tissue) having small side lobes of transmission beams, and in which mixing of an artifact component is few may be used. On the other hand, a reception signal in the inverse apodization acquired by the acquiring unit 151 in the first embodiment has high side lobes of reception beams as described above, it is preferable that a signal of a tissue harmonic component (a non-linear component of a tissue) having small side lobes of transmission beams, and in which mixing of an artifact component is few be used.

Therefore, in the first embodiment, it is preferable that at least a reception signal that is used by the calculating unit 152 for calculation of a coefficient distribution be a reception signal for which a non-linear component is extracted. In terms of simplifying a configuration of the transceiving unit 11, it is advantageous to regard, in both the normal apodization and the inverse apodization, "IQ-CH data" shown in FIG. 8 as data string of an IQ signal from which a tissue harmonic component is extracted. In such a case, for example, the transceiving unit 11 performs ultrasonic wave transmission/reception by the PM method described above to acquire a signal for which a non-linear component is extracted, and performs the normal apodization and the inverse apodization.

Figure 10:
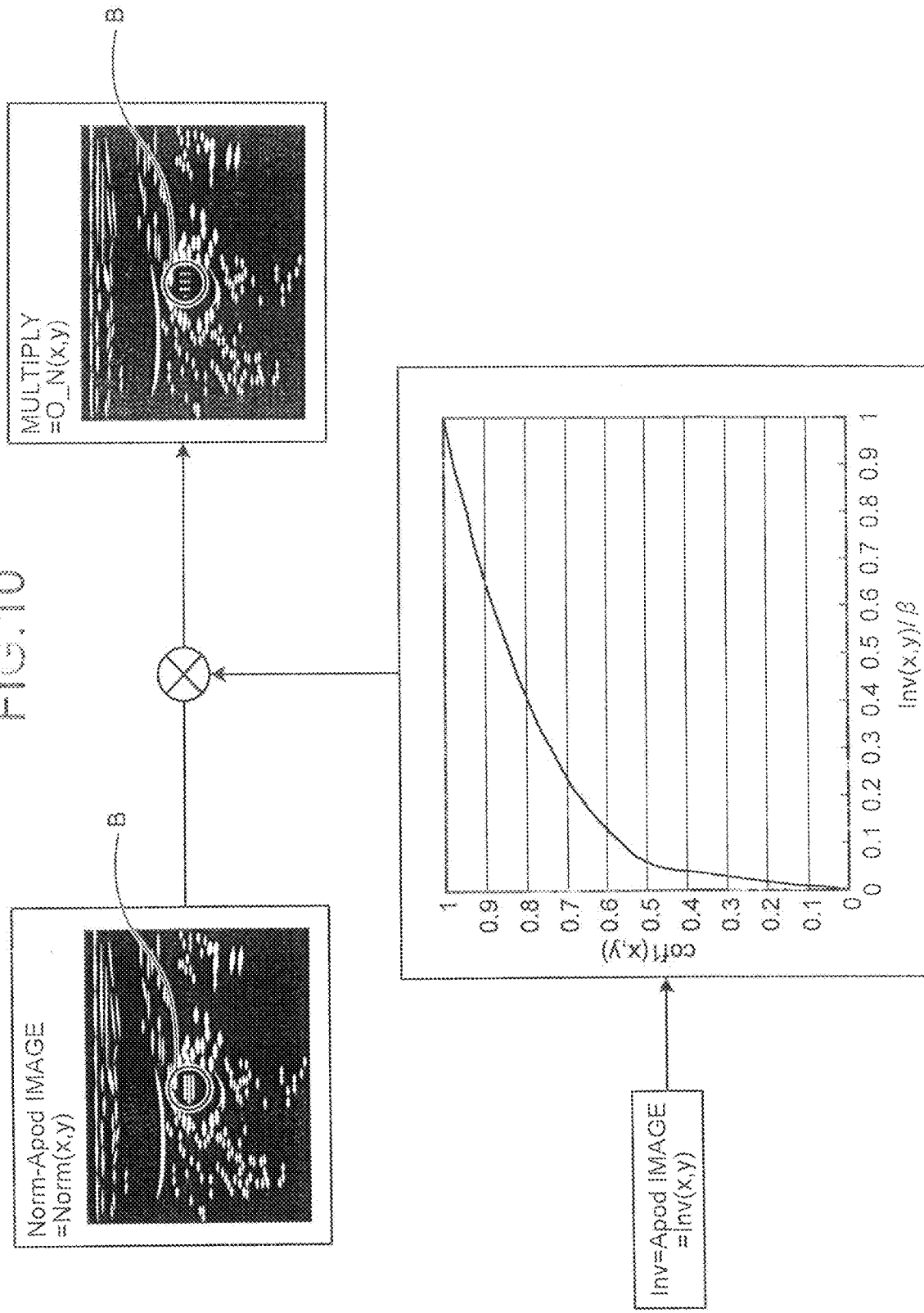
FIG. 10 is a diagram (3) for explaining the first embodiment.
Figure 11:
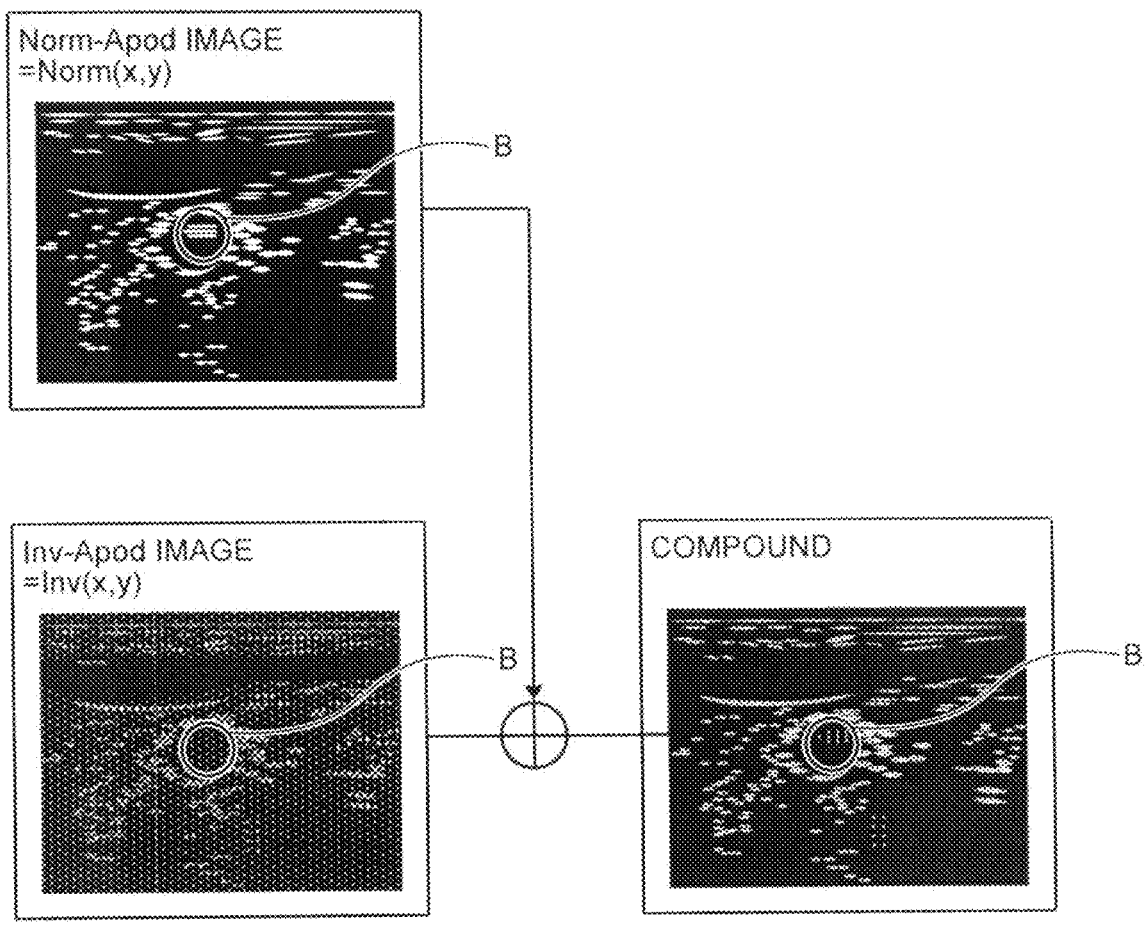
FIG. 11 is a diagram (4) for explaining the first embodiment.

An effect and the like obtained by the processing described above are explained below. "Norm-Apod image=Norm(x, y)" and "Inv-Apod image=Inv(x, y)" shown in FIG. 8 and the like are B-mode image data that is obtained by imaging a region including a carotid artery by THI by using a linear probe, and "Multiply=O_N(x, y)" shown in FIG. 10 is B-mode image data indicating a result of application of the present embodiment. Furthermore, "Compound" shown in FIG. 11 is image data that is obtained by compositing "Norm(x, y)" and "Inv(x, y)" by a conventional compounding processing, for comparison with "Multiply".

Because a lumen of the carotid artery is a low echo portion in which blood through which ultrasonic waves easily pass is filled, when a reverberation component is not present, the lumen is drawn in black in an image. In FIG. 10 and FIG. 11, a lumen portion inside a carotid artery is indicated as "B". As shown in FIG. 10, in "Norm(x, y)", although the lateral resolution is high, a reverberation component is superimposed particularly on the lumen portion B of the carotid artery. Moreover, as shown in FIG. 11, in "Inv(x, y)", although the reverberation component in the lumen portion B is reduced, the lateral resolution is degraded. In addition, in "Inv(x, y)", moire on a deep thyroid gland is observed. However, in "Multiply=O_N(x, y)" shown in FIG. 10, the reverberation component in the lumen portion B observed in "Norm(x, y)" is reduced, and the lateral resolution of "Norm(x, y)" is maintained. On the other hand, in "Compound" shown in FIG. 11, although the reverberation component in the lumen portion B is reduced, speckled granular blurriness in the thyroid gland caused by degradation of the lateral resolution, and remaining moire on the deep thyroid gland "Inv(x, y)" are observed.

Figure 12:
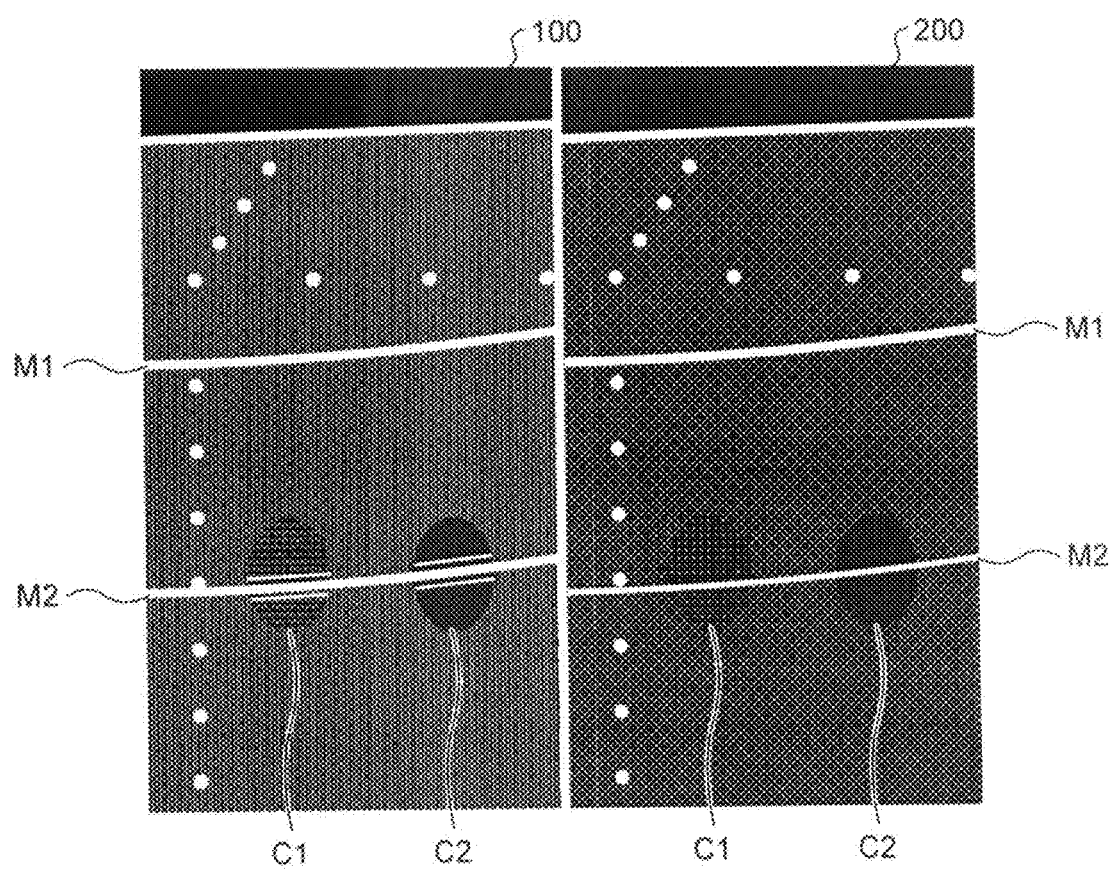
FIG. 12 is a diagram (5) for explaining the first embodiment.

Furthermore, FIG. 12 indicates a result of imaging a phantom covered with water on a surface thereof by THI to acquire an image including a specular reverberation component. An image 100 indicated in a left figure is B-mode image data of a tissue harmonic component acquired by the normal apodization, and an image 200 is image data that is acquired by the above multiplication processing. In the image 100, a single specular-reflection component M1 between a surface of the phantom and a probe surface, a double specular-reflection component M2 between the surface of the phantom and the probe surface, and a reverberation component superimposed on a portion C1 and a portion C2 that simulate cysts are observed. The portion simulating a cyst appears in black in an image when a reverberation component is not present, similarly to the lumen inside a carotid artery. On the other hand, in the image 200, it is observed that the double specular-reflection component M2 between the surface of the phantom and the probe and the reverberation component superimposed on the portion C1 and the portion C2 that simulate cysts are reduced compared to the image 100. However, a reverberation component (particularly, the single specular-reflection component M1 between the surface of the phantom and the probe surface) that is superimposed on a tissue having high brightness has a large coefficient value as described later because a background tissue component is large, and therefore, an effect of reducing reverberation is poor. Image data shown in FIG. 8 to FIG. 12 indicate results of processing performed with the settings of "$\alpha=\frac{1}{4}$, $\beta=192$, max=255".

As described, an image output by the above multiplication processing is to be a high quality image in which reverberation superimposed on a portion with low brightness is reduced and the lateral resolution and the sensitivity are maintained. This is achieved by the calculation method of the coefficient value described above.

As for a converting method to acquire a coefficient value, which is output data, from a reception signal, which is input data, of the inverse apodization, it is desirable that for a degree of input intensity at such a level being a boundary of a signal and a noise, an output value be maintained high in a signal region, and an output value be sufficiently small in a noise region. As a simplest method to obtain such a conversion characteristics, threshold processing is conceivable in which an output value is set to "1" when an input value exceeds a predetermined threshold, and to "0" when the input value is equal to or smaller than the threshold.

However, a "signal-noise boundary level" used to set a threshold generally varies according to the subject P, and therefore, cannot specifically determined. Accordingly, to obtain a robust reverberation reducing effect, it is effective to use a conversion characteristics that smoothly varies with respect to an input and has a characteristic close to the threshold processing.

For a specific method to obtain such a characteristic, it is preferable to give an output value by a "power function" according to an input level as indicated in above Equation 1. For example, in a conversion characteristics shown in FIG. 9 and FIG. 10, in a range in which "Inv(x, y)/$\beta$" is larger than "0.1", the coefficient value smoothly varies, and in a range in which "Inv(x, y)/$\beta$" is equal to or smaller than "0.1", the coefficient value abruptly decreases.

However, when the above coefficient control is performed, as is obvious from the graphs in FIG. 9 and FIG. 10, in the output image data "0_N8x, y)", a signal in a low brightness region is hardly displayed, and therefore, a display dynamic range appears to be narrow and a gain tends to decrease. Therefore, the control unit 18 according to the first embodiment may compensate, using a predetermined look up table (LUT), the display dynamic range and the gain at the time of displaying output image data so that image data on which the above multiplication processing is not performed and the display dynamic range and the gain on appearance are equivalent.

Figure 13:
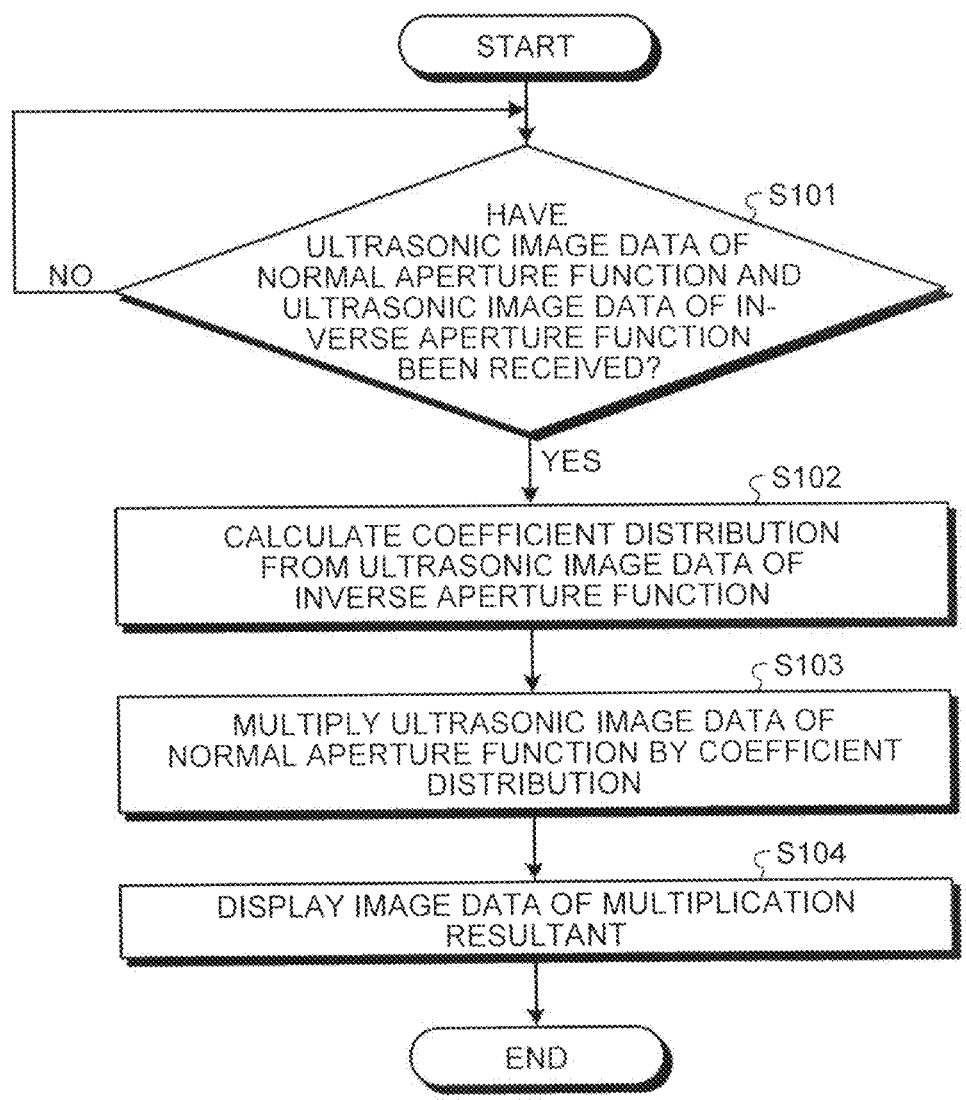
FIG. 13 is a flowchart indicating one example of processing of the ultrasonography apparatus according to the first embodiment.

Subsequently, using FIG. 13, a flow of the processing by the ultrasonography apparatus according to the first embodiment is explained. FIG. 13 is a flowchart indicating one example of the processing performed by the ultrasonography apparatus according to the first embodiment. FIG. 13 indicates one example of processing that is performed acquiring ultrasonic image data of the normal apodization and ultrasonic image data of the inverse apodization by the acquiring unit 151.

As exemplified in FIG. 13, the acquiring unit 151 of the ultrasonography apparatus according to the first embodiment determines whether ultrasonic image data of the normal aperture function and ultrasonic image data of the inverse aperture function are acquired (step S101). When ultrasonic image data of the normal aperture function and ultrasonic image data of the inverse aperture function have not been acquired (step S101: NO), the acquiring unit 151 waits until acquired.

On the other hand, when ultrasonic image data of the normal aperture function and ultrasonic image data of the inverse aperture function have been acquired (step S101: YES), the calculating unit 152 calculates a coefficient distribution from the ultrasonic image data of the inverse aperture function (step S102). The multiplying unit 153 then multiplies the ultrasonic image data of the normal aperture by the coefficient distribution (step S103).

Subsequently, by the control of the control unit 18, the monitor displays image data of a multiplication resultant (step S104), and the processing is ended. In the present embodiment, at step S104, the monitor 2 may display the ultrasonic image data of the normal aperture and the ultrasonic image data of the inverse aperture function together with the image data of the multiplication resultant, by an instruction of the control unit 18. Moreover, in parallel with the processing at step S102 and step S103, for example, the image generating unit 14 may generate compound image data that is obtained by compounding processing of the ultrasonic image data of the normal aperture and the ultrasonic image data of the inverse aperture function, and the monitor 2 may display the compound image data at step S104.

As described above, in the first embodiment, a reception signal with excellent spatial resolution and sensitivity acquired by the normal apodization is used as a base signal. In the first embodiment, a "weight (coefficient)" is calculated from a reception signal in which a reverberation component is reduced acquired in the inverse apodization, and by multiplying the base reception signal by the "weight (coefficient)", output image data for display is obtained. Because, in the first embodiment, a weight for the base signal is determined from a reception signal of the inverse apodization in which reverberation is reduced, for example, it is possible to reduce a reverberation component generated in a portion drawn in black (hereinafter, described as a black void portion) when a reverberation component is not present such as a lumen and a cyst. Furthermore, in the first embodiment, because a signal of the normal apodization with small side lobes and excellent lateral resolution is used as a base, the lateral resolution is improved from the conventional compounding processing, and moire is reduced.

Moreover, in the first embodiment, by using a non-linear component (tissue harmonic component), it becomes possible to reduce influence of increase of side lobes that is caused by applying the inverse apodization. From these facts, in the first embodiment, a high quality image in which reverberation is reduced, and the lateral resolution and the sensitivity are maintained can be acquired.

Although in one example described above, a case of using two different aperture functions has been explained, the first embodiment is not limited thereto. For example, in the first embodiment, three kinds of aperture functions may be used with the aperture function of the hamming window and the aperture function of the rectangular window as two kinds of the normal aperture functions, and the aperture function in which the center portion is zero as the inverse aperture function. In such a case, the multiplying unit 153 multiplies a compound signal that is compounded by performing signal averaging or weighting addition on a reception signal that is acquired by the aperture function of the hamming window and a reception signal that is acquired by the aperture function of the rectangular window, by a coefficient distribution that is calculated by a reception signal of the aperture function in which the center portion is zero.

Furthermore, for example, in the first embodiment, the aperture function of the hamming window may be used as the normal aperture function, and the aperture function in which the center portion is zero and the other inverse aperture function described above may be used as the inverse aperture functions. In such a case, the calculating unit 152 calculates a coefficient distribution from a compound signal that is compounded by performing signal averaging or weighting addition on two reception signals that are acquired by the two kinds of the inverse aperture functions, and the multiplying unit 153 multiplies a reception signal that is acquired by the aperture function of the hamming window by the coefficient distribution.

Moreover, for example, in the first embodiment, two kinds of the normal aperture functions and two kinds of the inverse aperture functions may be used. In such a case, the calculating unit 152 calculates a coefficient distribution from a compound signal of two reception signals that are acquired by the two kinds of the inverse aperture functions, and the multiplying unit 153 multiplies a compound signal of two reception signals that are acquired by the two kinds of normal aperture functions by the coefficient distribution. The above combination can be changed arbitrarily, for example, according to a demand of an operator.

Second Embodiment

In the first embodiment, a case in which a "center-fixed inverse aperture-function" in which a reception position at which a weight becomes small inside the reception aperture is fixed to the center of the reception aperture is used as the inverse aperture function has been explained. In a second embodiment, a case in which an inverse aperture function in which a reception position at which a weight becomes small is adaptively shifted according to an imaging condition and an imaging part is used is explained using FIG. 14 to FIG. 19. FIG. 14 to FIG. 19 are diagrams for explaining the second embodiment.

When a "boundary formed at a subject causing reverberation and the probe surface are parallel", and "a direction of ultrasonic wave transmission/reception is perpendicular to the probe surface", "the directivity of a main beam of a reflected signal and the directivity of a main beam of a reverberation signal are in an identical direction", and "a reception position of a reverberation component is substantially at the center portion of the reception aperture similarly to the reception position of a reflection component". When these preconditions are satisfied, it becomes possible to remove multiplex signals by the "center-fixed inverse aperture-function".

However, in the inverse apodization with the "center-fixed inverse aperture-function", if a subject is inclined relative to the probe surface, the above preconditions are not satisfied, and it can be ineffective. Furthermore, in the inverse apodization with the "center-fixed inverse aperture-function", if a transmission beam is steered (deflected), the above preconditions are not satisfied, and it can be ineffective. That is, when the above preconditions are not satisfied, a reception position at which reverberation components are received with matched phases at the reception aperture is shifted toward an aperture end portion from the aperture center portion. In such a case, if the "center-fixed inverse aperture-function" is used, a reverberation signal is to be received at a transducer position having a weight, and the reverberation reducing effect is degraded.

As described, a reception position at which reverberation components are received with matched phases at the reception aperture is shifted from relation with the direction of a subject causing reverberation. However, assuming that reverberation by an angle formed with a direction of an ultrasonic wave transmission/reception and a direction of a subject (boundary formed by a subject being reverberation source) is caused by specular reflection, a position at which a reflected signal and a reverberation signal are received at the reception aperture can be estimated by geometrical operation.

Figure 14:
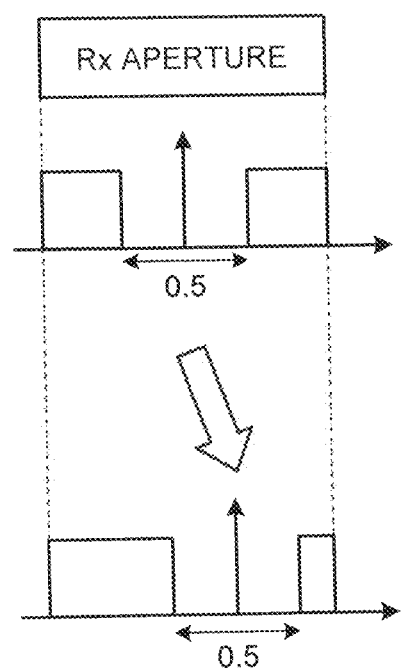
FIG. 14 is a diagram (1) for explaining a second embodiment.

Therefore, in the second embodiment, the control unit 18 shown in FIG. 1 calculates a reception position of a reverberation component based on a direction of ultrasonic wave transmission/reception and a direction of a subject causing reverberation, to create an inverse aperture function. For example, the control unit 18 uses the inverse aperture function of the aperture function in which the center portion is zero as a base as shown in FIG. 14. When the control unit 18 derives that a reception position of a reverberation component in the reception aperture (Rx Aperture) is on a right side relative to the aperture center, from calculation based on the direction of the ultrasonic wave transmission/reception and the direction of the subject, as shown in FIG. 14, a range in which a "weight: 0" is applied is shifted rightward. In the following, the inverse aperture function created in the second embodiment is described as a "shifted inverse aperture-function" in some cases. Moreover, in the following, the inverse apodization by the "shifted inverse aperture-function" is described as "shifted inverse apodization" in some cases. Furthermore, in the following, the inverse apodization by the "center-fixed inverse aperture-function" is described as "fixed inverse apodization" in some cases.

Figure 15:
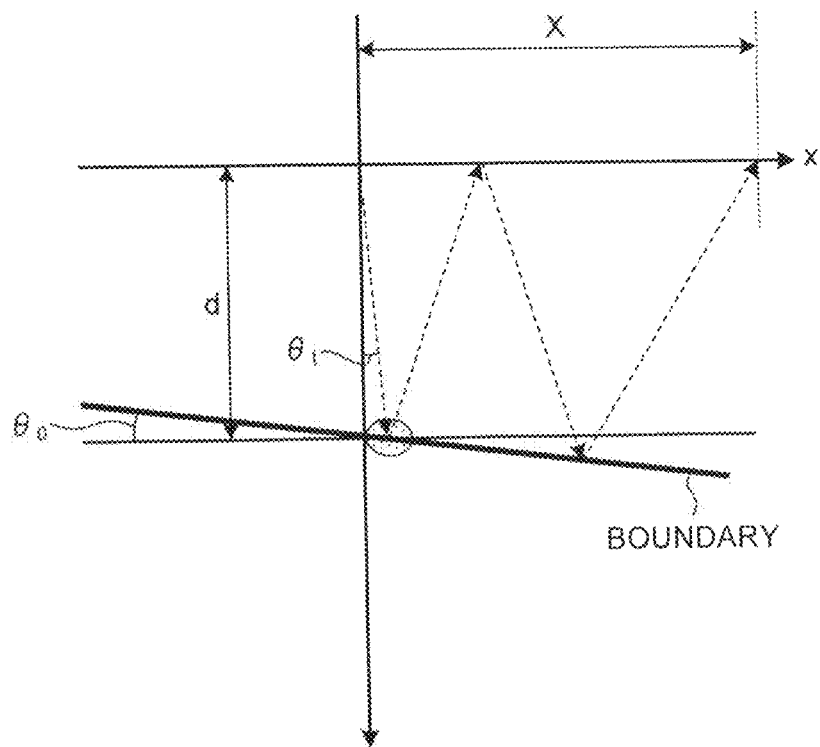
FIG. 15 is a diagram (2) for explaining the second embodiment.

The shifted inverse apodization is performed by the control unit 18 acquiring parameters shown in FIG. 15. In FIG. 15, a direction of arrangement of transducers (lateral direction) is indicated by an x axis. Moreover, in FIG. 15, a direction that passes through a center position of the reception aperture (that is, a depth direction) perpendicular to the x axis is indicated by a downward arrow. In the following, explanation is given assuming that the center position of the reception aperture (and the transmission aperture) is an origin (0, 0).

Furthermore, FIG. 15 indicates that an angle "$\theta_t$" formed by a direction of a transmission/reception beam and the depth direction is used as one example of a parameter indicating the direction of the transmission/reception beam. Moreover, FIG. 15 indicates that an angle "$\theta_0$" formed by direction of the transmission/reception beam and the x axis is used as one example of a parameter indicating the direction of the subject. Furthermore, "d" shown in FIG. 15 indicates a depth of a position at which an ultrasonic beam transmitted at the angle "$\theta_t$" is first reflected on a boundary formed by the subject inclined at the angle "$\theta_0$". That is, "d" shown in FIG. 15 indicates the depth at which the subject is positioned on a scan line.

Moreover, "X" shown in FIG. 15 indicates a distance from the center position of the reception aperture to a reception position at which a main beam of a single reverberation is received at the reception aperture. That is, "X" indicates a reference position that is used to set a range in which a weight is reduced, and is to be, for example, a center of gravity position (center position) of a range in which a transducer group weight of which is set to "0" occupies. The control unit 18 calculates "X" by, for example, multiplying a function $F(\theta_t, \theta_0)$ that is formulated with the angle "$\theta_t$" and the angle "$\theta_0$" by "d". This $F(\theta_t, \theta_0)$ is explained in detail later using a mathematical expression.

First, a method of acquiring various kinds of parameters shown in FIG. 15 is explained. Because the control unit 18 controls ultrasonic wave transmission/reception, the control unit 18 can acquire the angle "$\theta_t$" indicating a direction of a transmission/reception beam. That is, the control unit 18 acquires the angle "$\theta_t$" from various kinds of transmission/reception conditions that are set prior to ultrasonic scanning. For example, the control unit 18 acquires the angle "$\theta_t=0$" in normal B-mode imaging.

Furthermore, the control unit 18 acquires the angle "$\theta_0$" indicating a direction of a subject by various methods explained below. In the simplest method, the control unit 18 acquires a value that is initially set as the angle "$\theta_0$" in advance. For example, the control unit 18 acquires the angle "$\theta_0=0$ degrees", "$\theta_0=3$ degrees", and the like from setting values stored in the internal storage unit 17. In such a case, an operator can change the value "$\theta_0$" initially set, arbitrarily according to information of an examined part, and the like.

Figure 16:
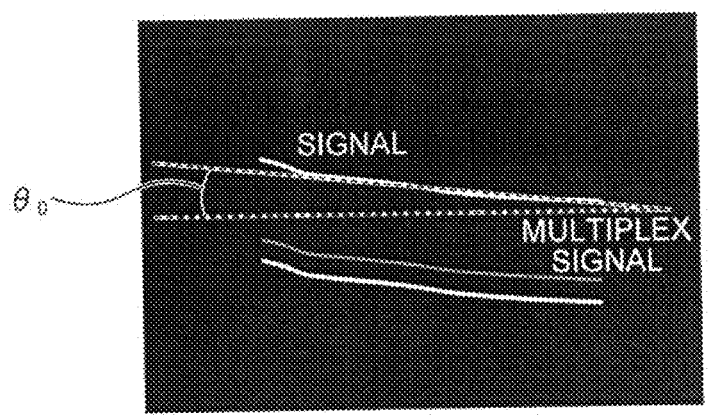
FIG. 16 is a diagram (3) for explaining the second embodiment.

Alternatively, the angle "$\theta_0$" indicating a direction a subject can be acquired using ultrasonic image data that is acquired by imaging a scanning range in which actual ultrasonic wave scanning is performed by normal B-mode. In such a case, the control unit 18 acquires a direction of a subject based on information input by an operator referring to ultrasonic image data that has been acquired in advance. For example, the control unit 18 causes the monitor 2 to display B-mode image data that is acquired beforehand by preliminary imaging, as shown in FIG. 16. In the B-mode image data exemplified in FIG. 16, a "signal" corresponding to an inclined blood vessel wall is shown, and furthermore, a "multiplex signal" corresponding to reverberation by a blood vessel wall at a shallow position is shown. In the B-mode image data exemplified in FIG. 16, a "multiplex signal" corresponding to reverberation by a blood vessel wall at a deep position signal is not shown due to attenuation or a display depth. The operator measures the inclination of the blood vessel wall at a shallow position causing the multiplex signal using a tool for angle measurement. For example, the operator turns a knob for the angle measurement included in the input device 3, to measure an angle of the "signal". The control unit 18 acquires the angle measured with the knob by the operator as the angle "$\theta_0$" indicating a direction a subject.

Because measuring a direction of a subject manually is processing needing an effort for an operator, the control unit 18 may acquire a direction of a subject automatically. When automation of acquisition processing for the angle "$\theta_0$" is specified, the control unit 18 estimates a direction of a subject causing reverberation using at least one reception signal acquired by the acquiring unit 151, to set the inverse aperture function. Specifically, the control unit 18 analyzes ultrasonic image data that has been acquired in advance, to estimate a direction of a subject. For example, the control unit 18 estimates the angle "$\theta_0$" indicating a direction of a subject by performing edge detection or main component analysis as analysis processing of the B-mode image data shown in FIG. 16. For example, the control unit 18 performs edge enhancement processing of the B-mode image data shown in FIG. 16, and then detects an edge portion. Subsequently, the control unit 18 estimates the angle "$\theta_0$" from a direction of the detected edge portion. As the simplest example among these examples, the control unit 18 regards the direction of the edge is equal to "$\theta_0$", and estimates the direction of the edge as "$\theta_0$". Alternatively, the control unit 18 makes estimation assuming that a direction of a characteristic vector corresponding to a characteristic value (as a preferable example, a maximum characteristic value) that is acquired by the main component analysis of an image subjected to edge enhancement is equal to "$\theta_0$". The above method is merely one example, and the control unit 18 can estimate the angle "$\theta_0$" by various widely known methods.

When the angle "$\theta_0$" is performed by detection processing of image information, to reduce a load, the control unit 18 may perform following processing. Specifically, the control unit 18 performs the detection processing of image information, limiting to a region of interest (ROI) specified for B-mode image data imaged in advance. For example, the ROI is specified by an operator that has referred to the B-mode image data.

Alternatively, to reduce a load on an operator, the control unit 18 may automatically set the ROI. Usually, a region shown in a center of an image is a region that is particularly focused in image diagnosis. Therefore, to avoid a multiplex signal is shown in the center of an image, the control unit 18 automatically set the ROI in a predetermined shape setting the center of the image as a center.

Alternatively, the control unit 18 uses a depth at which a tissue of a subject of examination is positioned from a contact surface of the ultrasound probe 1, as a parameter used for automatic setting of the ROI. For example, the control unit 18 acquires information that a tissue of a subject of examination is a "carotid artery" from information relating to examination that has been input in advance. Usually, the depth at which a carotid artery is positioned from a contact surface of the ultrasound probe 1 is near "10 mm". For example, the internal storage unit 17 stores, for each tissue of a subject of examination, a table in which a representative depth at which the tissue is positioned. The control unit 18 refers to the table to acquire a depth that is associated with the tissue acquired from the examination information, to set the ROI in a predetermined shape. The control unit 18 automatically sets the ROI setting the depth at which the tissue of a subject of examination is positioned in center, to avoid a multiplex signal is shown in a region in which the tissue of a subject of examination is to be shown.

Alternatively, the control unit 18 uses a position of a transmission focus as a parameter used for automatic setting of the ROI. A region having the position of the transmission focus is also a region that is particularly focused in image diagnosis. Therefore, the control unit 18 automatically sets the ROI setting the depth position of the transmission focus in center, to avoid a multiplex signal is shown in a region including the position of the transmission focus.

The control unit 18 according to the second embodiment can perform two patterns of the shifted inverse apodization. In a first pattern, the control unit 18 calculates a reception position of a reverberation component without acquiring a depth "d" at which a subject is positioned on a scan line. Specifically, the control unit 18 calculates a reception position of a reverberation component assuming that the subject is positioned at respective depths of reception focuses set on a reception scan line.

For example, the control unit 18 uses depths of reception focuses on a scan line "$d_1, d_2, d_3, d_4, \ldots$" as "d" that is used to calculate the reception position of a reverberation component. The control unit 18 performs control of changing a width of the reception aperture according to a position of a reception focus. That is, the control unit 18 causes the transceiving unit 11 to perform the DVAF method described above. The control unit 18 then calculates the reception position of a reverberation component at the reception aperture at each reception focus. The control unit 18 calculates the reception position of a reverberation component at the reception aperture at each reception focus for each of reception scan lines.

Figure 17:
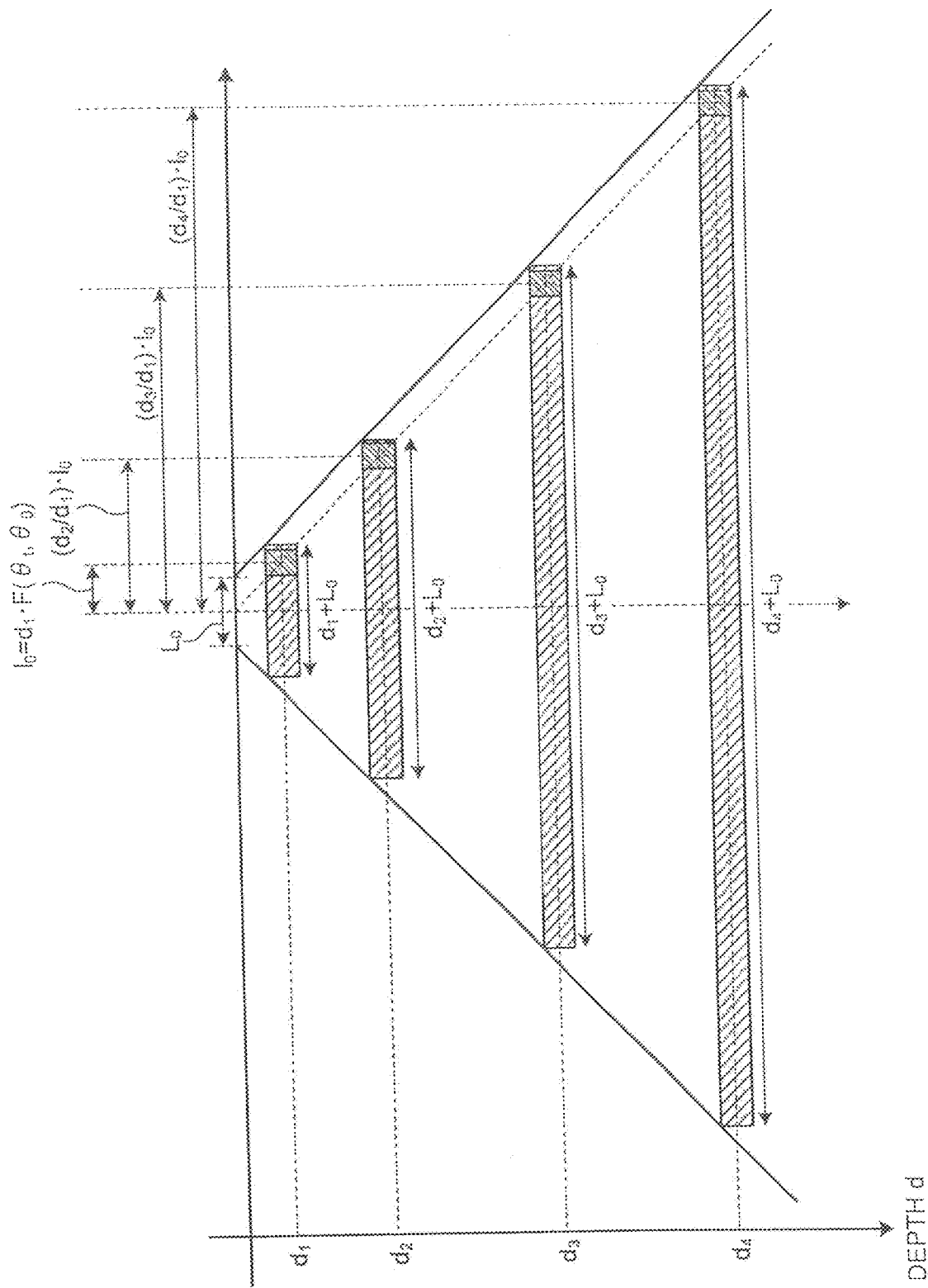
FIG. 17 is a diagram (4) for explaining the second embodiment.

FIG. 17 indicates the reception aperture at each reception focus set by the DVAF method, arranging at a depth of the corresponding reception focus. A width (L) for which the aperture width of the reception aperture is spread is "L=d/F-number" based on the depth "d" of a reception focus and "F-number".

"$L_0$" indicated in FIG. 17 is an initial value of the aperture width given at a depth "0". In FIG. 17, "F-number=1". Therefore, the aperture width at a depth "d1" is "$d_1+L_0$" as indicated in FIG. 17. Similarly, the aperture width at "$d_2, d_3, d_4$" are "$d_2+L_0, d_3+L_0, d_4+L_0$" respectively as indicated in FIG. 17. Because the reception aperture stretches from the aperture center toward both ends in the DVAF method, in FIG. 17 in which the reception aperture is arranged at each reception focus, the inclination of a straight line passing through end points of the reception apertures is "F-number/2=½".

The control unit 18 calculates a reception position "$X=l_0$" of a reverberation component at the depth "$d_1$" by "$l_0=d_1 \cdot F(\theta_t, \theta_0)$" as indicated in FIG. 17. Furthermore, as shown in FIG. 17, the control unit 18 calculates reception positions of reverberation component at "$d_2, d_3, d_4$" as "$(d_2/d_1) \cdot l_0, (d_3/d_1) \cdot l_0, (d_4/d_1) \cdot l_0$", respectively, using proportional relation. FIG. 17 indicates that a reverberation component (for example, a main beam of reverberation) is received at a position on a right side relative to the center portion of the reception aperture from relation between the angle "$\theta_t$" and the angle "$\theta_0$".

The control unit 18 creates the "shifted inverse aperture-function" based on a reception position of a reverberation component at the reception aperture of each reception focus from the angle "$\theta_t$" and the angle "$\theta_0$", and informs the "shifted inverse aperture-function" to the transceiving unit 11 (the adding unit 112*d*), thereby performing the shifted inverse apodization.

Figure 18:
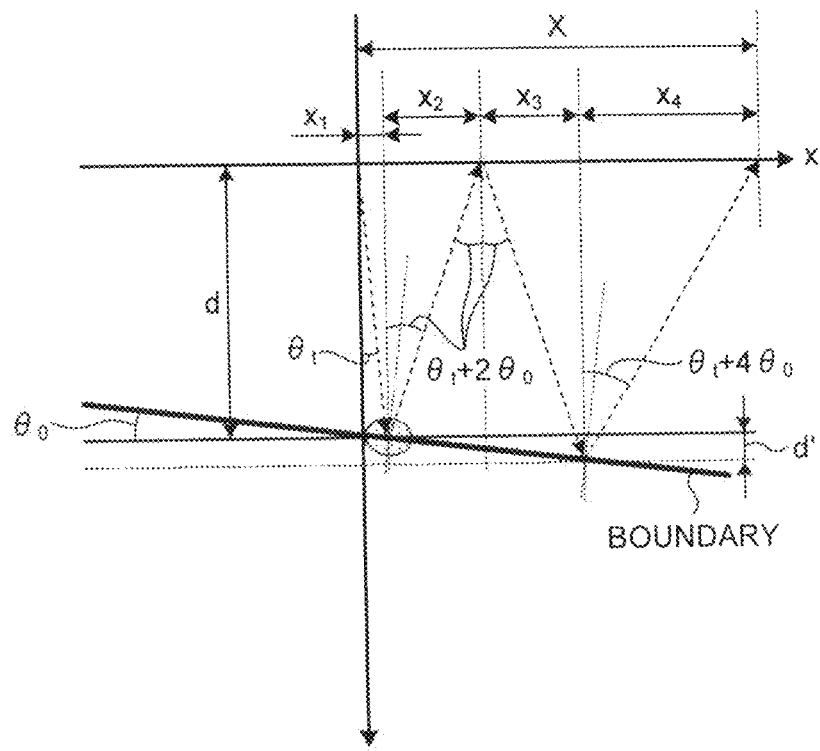
FIG. 18 is a diagram (5) for explaining the second embodiment.

Next, a calculation method of a reception position of a reverberation component is explained in detail using FIG. 18 and a mathematical expression. FIG. 18 indicates that a position (hereinafter, P1) that an ultrasonic beam that has been transmitted at the angle "$\theta_t$" first reaches on a boundary inclined by "$\theta_0$" is ($x_1$, d). Moreover, FIG. 18 indicates that a reception position (hereinafter, P2) on the probe surface of the reflected wave that has been reflected at P1 by specular reflection with the angle "$\theta_t$" and the angle "$\theta_0$" is ($x_1+x_2$, 0). Furthermore, FIG. 18 indicates that a position (hereinafter, P3) that the reflected wave reflected at P2 reaches the boundary again, by the specular reflection with the angle "$\theta_t$" and the angle "$\theta_0$" is ($x_1+x_2+x_3$, d+d'). Moreover, FIG. 18 indicates that a reception position (hereinafter, P4) of a reverberation component on the probe surface of the reflected wave that has been reflected at P3 by specular reflection with the angle "$\theta_t$" and the angle "$\theta_0$" is ($x_1+x_2+x_3+x_4$, 0).

"X" shown in FIG. 15 calculated in shifted inverse-reception apodization, that is, the reception position "X" to be a reference for setting a range in which a transducer group a weight of which is set to substantially "0" by the aperture function occupies is "$X=x_1+x_2+x_3+x_4$" as shown in FIG. 18.

First, an "angle between a direction from the origin to P1 and a depth direction" is "$\theta_t$" as shown in FIG. 18. Furthermore, by g geometrical operation assuming that reflected occurring between the angle "$\theta_t$" and the angle "$\theta_0$" is specular reflection, the "angle between a direction from P1 to P2 and a depth direction" and the "angle between a direction from P2 to P3 and a depth direction" are "$\theta_t+2\theta_0$" as shown in FIG. 18. Moreover, by similar geometrical operation, an "angle between a direction from P3 to P4 and a depth direction" is "$\theta_t+4\theta_0$" as shown in FIG. 18.

First, from "$\theta_t$" and "d", the control unit 18 calculates "$x_1$" by Equation 3 below. Furthermore, the control unit 18 calculates "$x_2$" from "$\theta_t+2\theta_0$" and "d" by Equation 4 below.

$$x_1 = d \cdot \tan(\theta_t) \tag{3}$$

$$x_2 = d \cdot \tan(\theta_t + 2\theta_0) \tag{4}$$

On the other hand, from "$\theta_t+2\theta_0$", "d", and "d'", "$x_3$" can be expressed by Equation 5 below. Furthermore, from "$\theta_t+4\theta_0$", "d", and "d'", "$x_4$" can be expressed by Equation 6 below.

$$\begin{aligned} x_3 &= (d+d') \cdot \tan(\theta_t + 2\theta_0) \\ &= x_2 + d' \cdot \tan(\theta_t + 2\theta_0) \end{aligned} \tag{5}$$

$$x_4 = (d+d') \cdot \tan(\theta_t + 4\theta_0) \tag{6}$$

Moreover, "d'" can be expressed by Equation 7 below.

$$\begin{aligned} d' &= (x_2 + x_3) \cdot \tan(\theta_0) \\ &= (2x_2 + d' \cdot \tan(\theta_t + 2\theta_0)) \cdot \tan(\theta_0) \end{aligned} \tag{7}$$

Developing Equation 7, Equation 8 below can be obtained.

$$d'(1 - \tan(\theta_t + 2\theta_0) \cdot \tan(\theta_0)) = 2x_2 \cdot \tan(\theta_0) \tag{8}$$

When an addition theorem of a trigonometric indicated in Equation 9 is applied, "$1-\tan(\theta_t+2\theta_0) \cdot \tan(\theta_0)$" expressed in a left side of Equation 8 is to be a right side of Equation 10 below.

$$\tan(\alpha + \beta) = \frac{\tan\alpha + \tan\beta}{1 - \tan\alpha\tan\beta} \tag{9}$$

-continued $$1 - \tan(\theta_t + 2\theta_0) \cdot \tan(\theta_0) = \frac{[\tan(\theta_t + 2\theta_0) + \tan(\theta_0)]}{\tan(\theta_0 + 3\theta_0)} \quad (10)$$

It is shown that by substituting Equation 10 in Equation 8, "d'" can be calculated from "x2", "$\theta_t$", "$\theta_0$" as indicated in Equation 11.

$$d' = 2x_2 \cdot \tan(\theta_0)\tan(\theta_t + 3\theta_0)/[\tan(\theta_t + 2\theta_0) + \tan(\theta_0)] \quad (11)$$

From the above, "$x_3$" can be calculated by Equation 12 below, and "$x_4$" can be calculated by Equation 13 below.

$$x_3 = (d + d') \cdot \tan(\theta_t + 2\theta_0) \quad (12)$$
$$= x_2 \cdot \left( \frac{1 + 2 \cdot \tan(\theta_t + 2\theta_0) \cdot \tan(\theta_0) \cdot \tan(\theta_t + 3\theta_0)}{[\tan(\theta_t + 2\theta_0) + \tan(\theta_0)]} \right)$$

$$x_4 = (d + d') \cdot \tan(\theta_t + 4\theta_0) \quad (13)$$
$$= x_2 \cdot \left( \frac{1 + 2 \cdot \tan(\theta_t + 4\theta_0) \cdot \tan(\theta_0) \cdot \tan(\theta_t + 3\theta_0)}{[\tan(\theta_t + 2\theta_0) + \tan(\theta_0)]} \right)$$

The control unit 18 acquires the angle "$\theta_t$" and the angle "$\theta_0$" by the above method, and calculates "$x_1$" and "$x_2$" by substituting the depth "d" of a reception focus, by Equation 3 and Equation 4. Using calculated "$x_2$", and "$\theta_t$" and "$\theta_0$", the control unit 18 then calculates "$x_3$" and "$x_4$" by Equation 12 and Equation 13. Subsequently, the control unit 18 calculates "$x_1+x_2+x_3+x_4$" to acquire a reception position "X" of a reverberation component. As is obvious from Equation 3, Equation 4, Equation 12, and Equation 13, when "d" is factored as a common factor, "$X=x_1+x_2+x_3+x_4$" can be formulated by a product of a function $F(\theta_t, \theta_0)$ that is expressed with the angle "$\theta_t$" and the angle "$\theta_0$", and "d". The control unit 18 can calculate the reception position "X" of a reverberation component at the reception aperture set for each reception focus by multiplying a value obtained by substituting the acquired angle "$\theta_t$" and angle "$\theta_0$" into $F(\theta_t, \theta_0)$ by an arbitrary depth "d".

This is the first pattern of the shifted inverse apodization. In the first pattern, a depth of a subject is a reception focus position, and a position of "X" is automatically calculated with $F(\theta_t, \theta_0)$ and "F-number". However, in the first pattern, because a transducer group a weight of which is "0" at each depth "d" is always present, the effective aperture width is small compared to the normal reception apodization.

On the other hand, in a shifted inverse apodization of a second pattern, the control unit 18 further acquires a depth "d" at which a subject is present on a scan line, to calculate a reception position of a reverberation component. That is, in the shifted inverse apodization of the second pattern, the control unit 18 calculates a reception position of a reverberation component based on a direction of ultrasonic wave transmission/reception, a direction of a subject causing reverberation, and a depth of the subject, to create the inverse aperture function.

Figure 19:
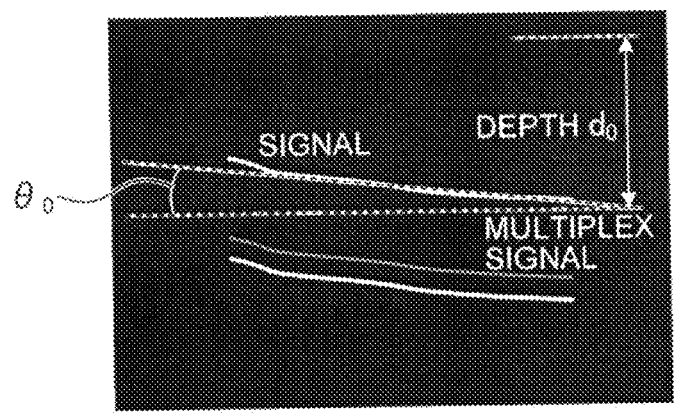
FIG. 19 is a diagram (6) for explaining the second embodiment.

B-mode image data shown in FIG. 19 is the same image as the B-mode image data shown in FIG. 16, and is B-mode image data that is imaged in advance. For example, an operator measures the angle "$\theta_0$" as shown in FIG. 19, and also measures a depth "$d_0$" of the subject at the same time. The control unit 18 acquires the depth measured by the operator as the depth "$d_0$" of the subject.

Alternatively, the control unit 18 estimates the angle "$\theta_0$" by edge detection or main component analysis as described above, and for example, acquires the depth "$d_0$", regarding an edge extracted by the edge detection as a boundary formed on the subject, by automatically measuring a position of the edge in an image.

Alternatively, the control unit 18 acquires "$d_0$" from among various parameters that are used for setting the ROI described above. Specifically, the control unit 18 acquires an "image center", a "representative depth of a tissue of a subject of examination", or a "transmission focus" that is used for setting the ROI as "$d_0$". By setting as "transmission focus=$d_0$", it is possible to respond immediately to a change of a transmission/reception condition during imaging.

For example, "$d_0$" shown in FIG. 9 is a depth at a right end of a subject. The control unit 18 calculates a depth "$d_i$" of a subject on each scan line from the angle "$\theta_0$" and "$d_0$", and creates the shifted inverse aperture-function at each scan line by "$d_i \cdot F(\theta_t, \theta_0)$". Subsequently, the control unit 18 instructs the transceiving unit 11 to use the created shifted inverse aperture-function at a reception focus of the depth "$d_i$", or at a reception focus near the depth "$d_i$", and further instructs the transceiving unit 11 to use the normal aperture function at reception focuses other than this reception focus.

That is, in the shifted inverse apodization of the second pattern, the shifted inverse aperture-function is applied at a reception focus corresponding to a depth of a subject, and the normal aperture function is applied at a reception focus that is far from the depth of the subject. In other words, the first pattern in which a depth of a subject is not used is a pattern setting a uniform shifted inverse aperture-function in an entire image (all sample points), and the second pattern that uses a depth of a subject is a pattern setting a shifted inverse aperture-function that is adaptively created for a local region among an entire image (all sample points).

In the second embodiment, by the processing described above, the inverse aperture function for which a region in which a weight is reduced is shifted can be applied to the inverse apodization in the first embodiment, according to an imaging condition and a position of a subject in a portion to be imaged. In a reception signal that is acquired by the shifted inverse apodization of the first pattern or the shifted inverse apodization of the second pattern, a reverberation component is preferably reduced compared to a reception signal that is acquired by the fixed inverse apodization. Moreover, the reception signal that is acquired by the shifted inverse apodization of the second pattern is a reception signal that is acquired by performing the inverse apodization limiting to a local region, and therefore, the sensitivity thereof is higher than that of a reception signal that is acquired by the shifted inverse apodization of the first pattern in which the overall effective aperture width is narrow.

In the second embodiment, the multiplying unit 153 multiplies a reception signal having excellent spatial resolution and sensitivity acquire by the normal apodization by a "weight (coefficient)" that is calculated from a reception signal acquired by the shifted inverse apodization. Accordingly, in the second embodiment, a high quality image in which reverberation is reduced, and the lateral resolution and the sensitivity are maintained can be acquired reliably.

A concept of the shifted inverse apodization described above is also applicable, for example, to the normal apodization that uses the normal aperture function of the hamming window. For example, "$x_1+x_2$" that can be calculated by Equation 3 and Equation 4 is to be a position at which a signal component is received. Therefore, for example, the control unit 18 may create a shifted normal aperture-function for which a position at which a weight in the hamming window is "1" is "$x_1+x_2$" when a position of "$x_1+x_2$" is distant more than a predetermined distance from the center of the reception aperture, to inform to the transceiving unit 11. That is, in the second embodiment, the processing explained in the first embodiment may be performed by the shifted normal apodization and the shifted inverse apodization. Furthermore, in the second embodiment, the normal aperture function that is used in the shifted inverse apodization of the second pattern may be the shifted normal aperture function described above.

Third Embodiment

In a third embodiment, a case in which the reverberation reducing effect is further enhanced by using a second coefficient distribution that is acquired independently from the coefficient distribution "cof1(x, y)" acquired in the normal and inverse apodization explained in the first embodiment or the second embodiment is explained using FIG. 20 to FIG. 25D, and the like. FIG. 20 to FIG. 25D are diagrams for explaining the third embodiment. In the following, the coefficient and the coefficient distribution "cof1 (x, y)" explained in the first embodiment are described as a first coefficient and a first coefficient distribution, respectively.

The acquiring unit 151 according to the third embodiment acquires an image data group that is constituted of multiple pieces of ultrasonic image data with various deflection angles generated by ultrasonic scanning in which the deflection angles of ultrasonic wave transmission/reception are varied among frames, and that is the ultrasonic scanning including a deflection angle of a predetermined direction (that is, the deflection angle of 0 degrees) performed to acquire multiple reception signals explained in the first embodiment or the second embodiment. The calculating unit 152 according to the third embodiment further calculates a second coefficient (second coefficient distribution) using at least one piece of the ultrasonic image data with a deflection angle of a direction other than the predetermined direction. The multiplying unit 153 according to the third embodiment multiplies image data that is obtained by performing compounding processing on ultrasonic image data of the deflection angle of the predetermined direction, or ultrasonic image data of each of deflection angles of directions including the predetermined direction from the image data group, by the first coefficient and the second coefficient (the first coefficient distribution and the second coefficient distribution).

That is, in the third embodiment, ultrasonic scanning in which the deflection angle is varied per frame (per image) explained using FIG. 2 is performed. For example, by the control of the control unit 18, the transceiving unit 11 causes the ultrasound probe 1 to execute ultrasonic wave transmission/reception of three directions (deflection angles: 0 degrees, +θ degrees, −θ degrees). Thus, three pieces of B-mode image data with different deflection angles are generated by the image generating unit 14. Processing explained below is applicable as long as being an image signal as a reception signal explained in the first embodiment.

Figure 20:
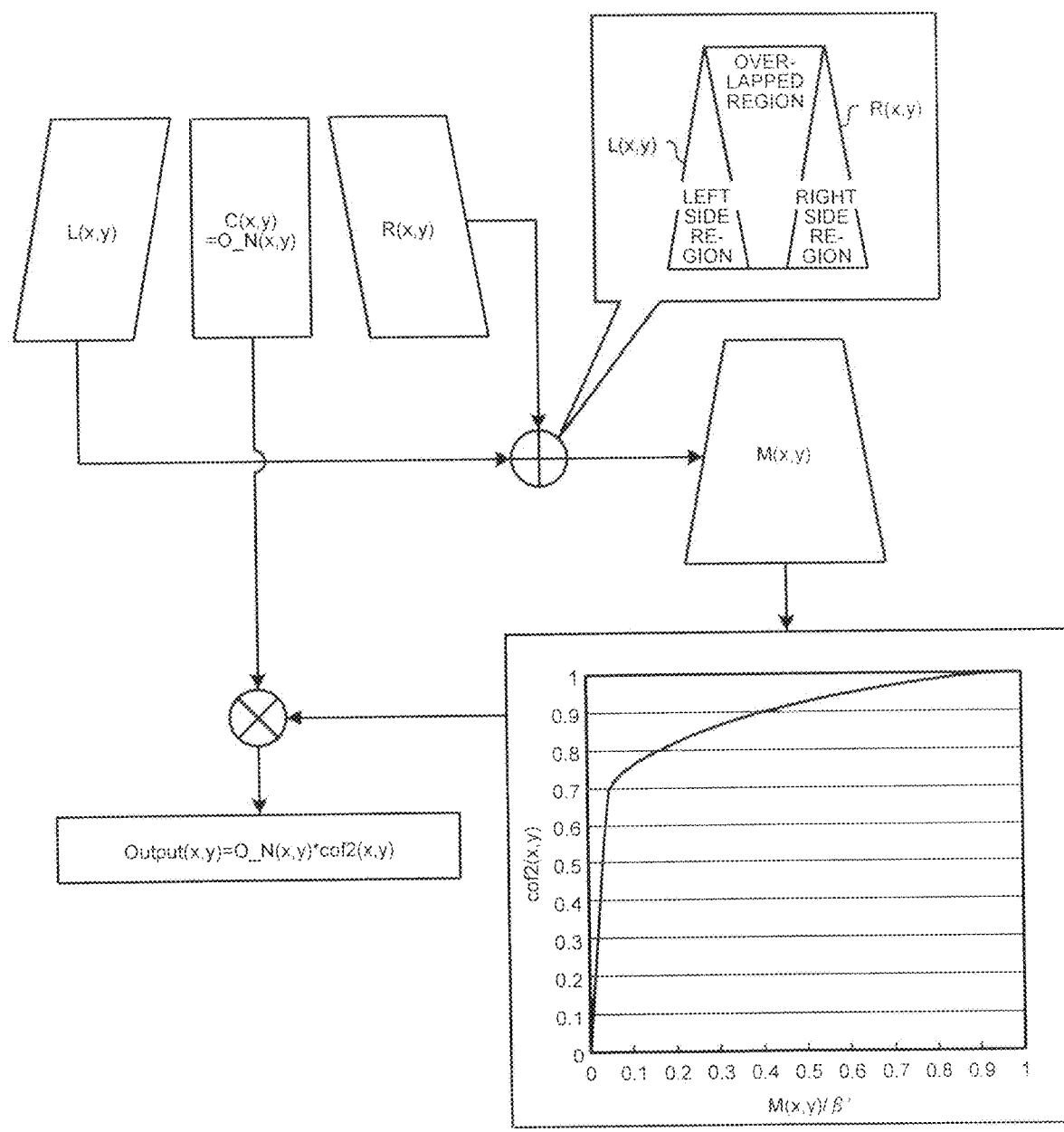
FIG. 20 is a diagram (1) for explaining a third embodiment.

The above predetermined direction is the direction of the deflection angle of "0 degrees". The direction of the deflection angle of "0 degrees" is a direction in which scanning to acquire "0_N(x, y)" explained in the first embodiment is performed. The acquiring unit 151 acquires these three pieces of the B-mode image data. "L(x, y)" and "R(x, y)" shown in FIG. 20 are left-deflected image data and right-deflected image data in which reverberation component is reduced by inclined transmission and reception. Moreover, "C(x, y)" shown in FIG. 20 is B-mode image data of the direction of the deflection angle of "0 degrees" associated with FIG. 2, and is front image data (center image data) having high lateral resolution and sensitivity, but has a possibility that the reverberation component is increased compared to the left-deflected image data and the right-deflected image data. "(x, y)" indicates a position of each pixel constituting image data.

In FIG. 20, image data "0_N(x, y)" that is finally acquired at the deflection angle of 0 degrees by the normal/inverse apodization of the first embodiment or the second embodiment corresponds to "C(x, y)". In this image data, a reverberation component is reduced by effectively reducing a weight of a signal at a position at which phases of the reverberation components are matched in the reception aperture. On the other hand, for image data that is deflected rightward and leftward, the reverberation component is reduced by inclined transmission/reception as shown in FIG. 4 so that the reverberation component goes out of the reception aperture. As described, a principle of reducing a reverberation component by the embodiment described previously and a principle of reducing a reverberation component by inclined transmission/reception are different, and acquiring further effect of reducing reverberation components by combining these two actions is characteristics of the third embodiment, and a fourth embodiment and a fifth embodiment described later. "0_N(x, y)" is "Norm(x, y)*cof1(x,y)" as indicated in Equation 2. The multiplying unit 153 according to the third embodiment performs processing of multiplying "Norm(x, y)" by the first coefficient distribution and the second coefficient distribution. When "cof1(x, y)" is acquired in the third embodiment, as an exponentiation value "α" described above, it is preferable that a value of about ⅛ to ⅙, which is half of about ¼ to ⅓, be set.

FIG. 20 shows a case in which the calculating unit 152 calculate the second coefficient distribution with "L(x, y)" and "R(x, y)" as subjects of processing, and the multiplying unit 153 handles "C(x, y)=0_N(x, y)" as a subject of multiplication of the second coefficient distribution. As the input data "L(x, y)" and "R(x, y)" to calculate the second coefficient distribution, it is effective if data in which occurrence of reverberation decreases at a black void portion such as a lumen and a cyst described above is selected. A condition under which "L(x, y)" and "R(x, y)" are acquired is selectable from among three cases described below. This is described in detail later.

First, the calculating unit 152 acquires mean image data "M(x, y)" of "L(x, y)" and "R(x, y)" as shown in FIG. 20. Specifically, the calculating unit 152 acquires "M(x, y)" by Equation 14 below.

$$M(x, y) = \frac{(L(x, y) + R(x, y))}{2} \quad \text{(overlapped region)} \atop = L(x, y) \quad \text{(left side region)} \atop = R(x, y) \quad \text{(right side region)} \quad (14)$$

As shown in FIG. 20, positioning "L(x, y)" and "R(x, y)", there are an overlapped region that is a region in which both are overlapped, a left side region other than the overlapped region in "L(x, y)", and a right side region other than the overlapped region in "R(x, y)". Equation 14 above indicates that a mean value of pixel values at the same position in "L(x, y)" and "R(x, y)" is allocated to the overlapped region, a pixel value of "L(x, y)" is allocated to the left side region, and a pixel value of "R(x, y)" is allocated to the right side region, thereby acquiring the mean image data "M(x, y)".

The calculating unit 152 calculates a coefficient distribution "cof(x, y)" from the mean image data "M(x, y)" as shown in FIG. 20. Specifically, the calculating unit 152 calculates "cof2(x, y)" by Equation 15 below.

$$\left.\begin{array}{l}cof2(x, y) = (M(x, y)/\beta')^{\alpha'}\\ \text{(where when } M(x, y) > \beta', cof2(x, y) = 1.0)\end{array}\right\} \quad (15)$$

In above Equation 15, an "α'-th power" of a value obtained by dividing M(x, y) by "β'" is defined as "cof2(x, y)". Furthermore, in above Equation 15, it is defined that "cof2(x, y)" is "1" when a value obtained by dividing "M(x, y)" by "β'" is larger than "1". "α', β'" are values that are set in advance for a similar purpose as "α, β" explained in the first embodiment. Specifically, "β'" signifies an upper level of an output signal, and is set to a level equal to or lower than the maximum value "max" in an image signal. It is preferable that "β'" be set to a level of about 70% to 80% of "max". Furthermore, it is preferable that "α'" be set to a value of about ⅛ to ⅙, which is half of about "¼ to ⅓" similarly to "α".

A graph shown in FIG. 20 is a graph in which output values "cof2(x, y)" that are calculated from input values "M(x, y)/β'" using Equation 15 where "α'=⅛" are plotted. An advantage of calculating the second coefficient distribution using a function including an arithmetic processing in which the calculating unit 152 exponentiates an input value as in Equation 15 is similar to the reason explained in the calculation processing of the first coefficient distribution "cof1(x, y)".

The multiplying unit 153 multiplies "C(x, y)=O_N(x, y)" by the second coefficient distribution "cof2(x, y)" as in Equation 20 and Equation 16, and outputs output image data "Output(x, y)=O_N(x, y)*cof2(x, y)". That is, the multiplying unit 153 outputs "Norm(x, y)*cof1(x, y)*cof2(x, y)" as "Output(x, y)".

$$\text{Output}(x,y)=O\_N(x,y)*cof2(x,y) \quad (16)$$

The control unit 18 controls to display the output image data "Output(x, y)" on the monitor 2 as B-mode image data subjected to correction processing. When coefficient control using "α', β'" is performed, similarly to a case of performing the coefficient control using "α, β" in the first embodiment, a signal in a low brightness region is hardly displayed. Therefore, also in the third embodiment, the control unit 18 may compensate, using a predetermined LUT, the display dynamic range and the gain at the time of displaying output image data so that image data on which the multiplication processing is not performed and the display dynamic range and the gain on appearance are equivalent.

Also in the third embodiment, as explained in the first embodiment, at least data that is used for calculation of the second coefficient distribution by the calculating unit 152 is preferable to be data for which a non-linear (tissue harmonic) component is extracted to prevent mixing of side lobe components. In such a case, also data to which the multiplying unit 153 multiplies by the second coefficient distribution is preferable to be data for which non-linear components are extracted in terms of a circuit configuration.

Next, a condition for generating "L(x, y)" and "R(x, y)" that are the input data to calculate the second coefficient distribution is explained referring to FIGS. 21A, 21B, 21C, and FIG. 22 to FIG. 24.

Figure 21A:
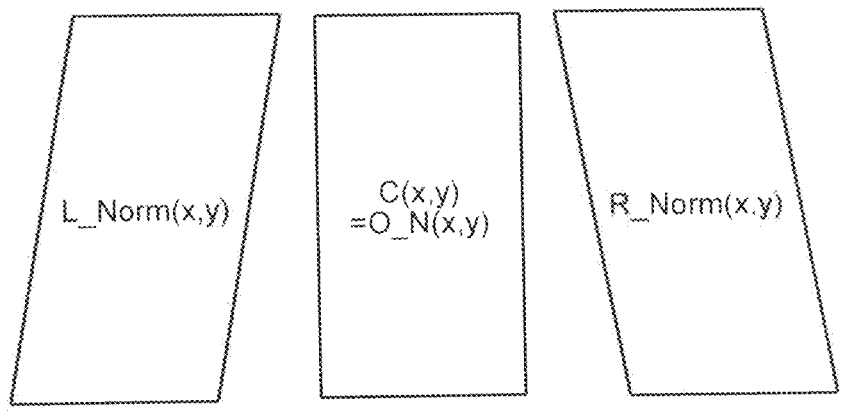
FIGS. 21A, 21B, and 21C are diagrams (2) for explaining the third embodiment.
Figure 21B:
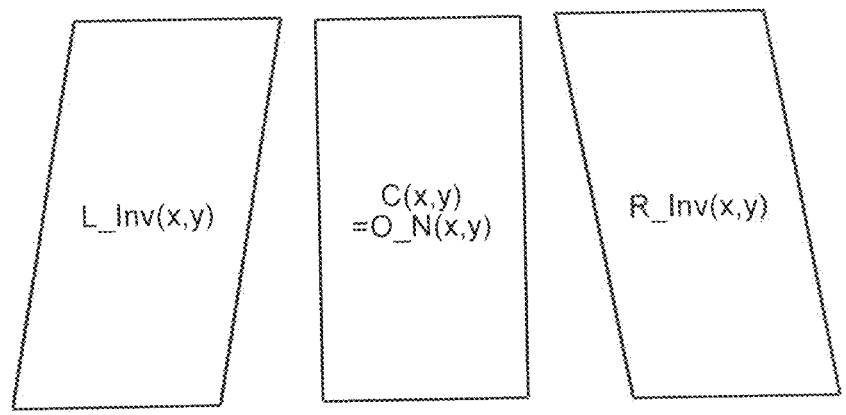
Figure 21C:
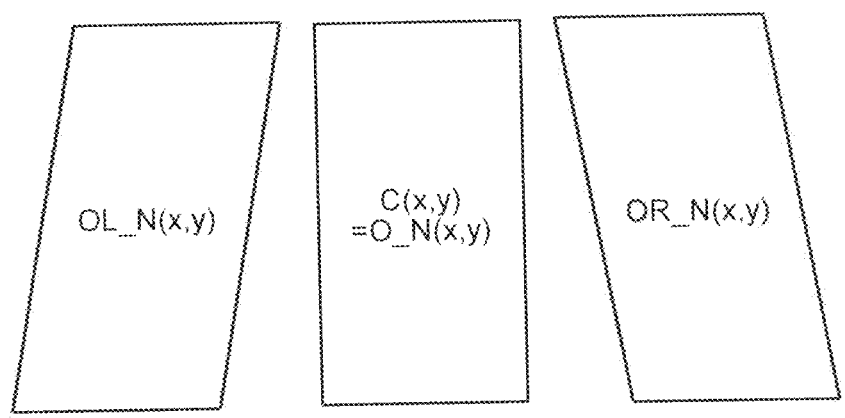

For "L(x, y)" and "R(x, y)" to acquire the second coefficient distribution, three cases shown in FIGS. 21A, 21B, and 21C are conceivable. In a first case, data used to calculate the second coefficient distribution by the calculating unit 152 is data that is generated based on the "normal aperture function in which a weight of a device in the center portion is larger than a weight of a device at the end portion of the reception aperture". For example, the acquiring unit 151 acquires B-mode image data "L_Norm(x, y)" and "R_Norm(x, y)" that are acquired by the normal apodization using the aperture function of the hamming window, as "L(x, y)" and "R(x, y)" as shown in FIG. 21A. The calculating unit 152 then calculates the second coefficient distribution from mean image data of "L_Norm(x, y)" and "R_Norm(x, y)".

Figure 22:
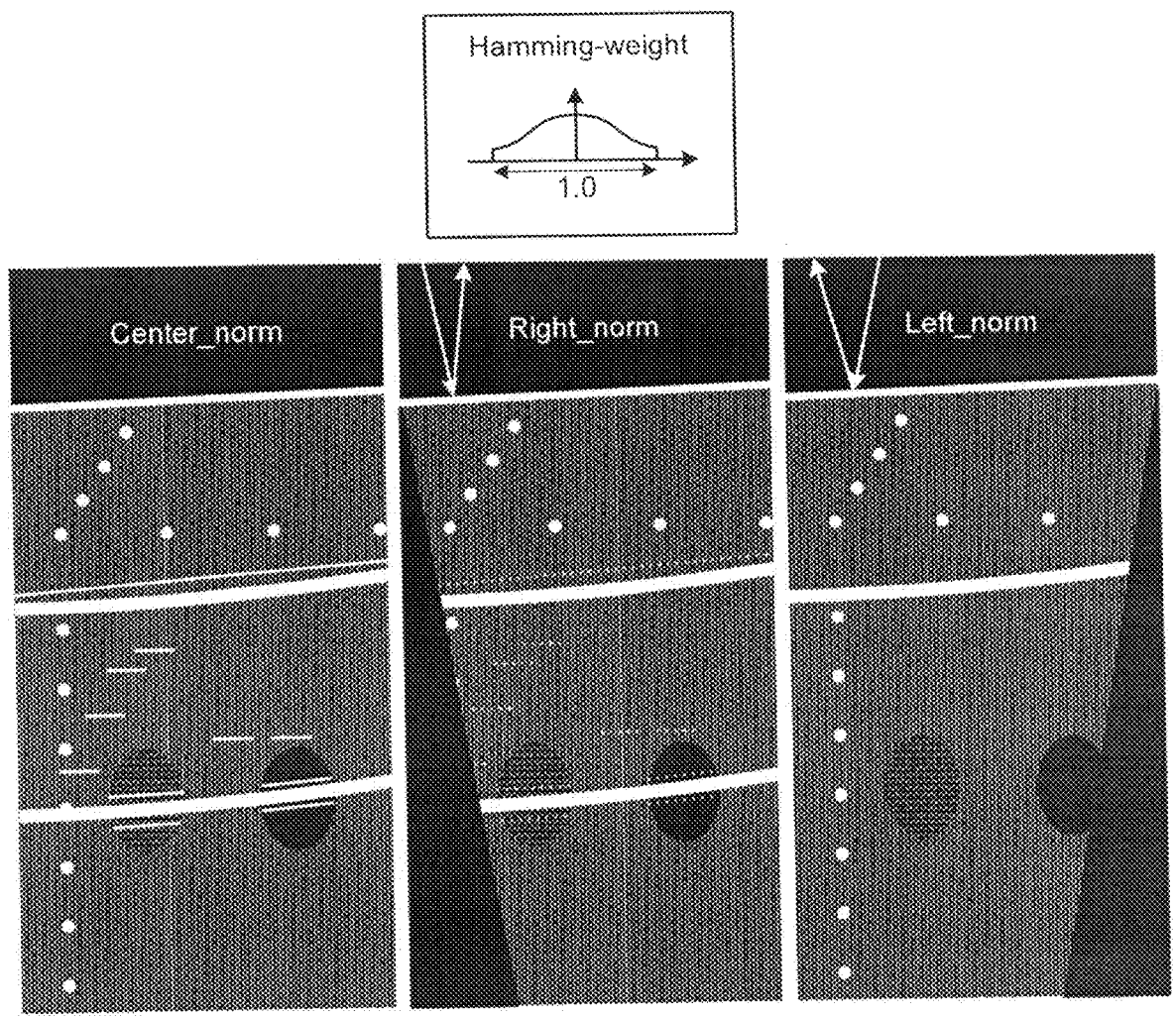
FIG. 22 is a diagram (3) for explaining the third embodiment.
Figure 23:
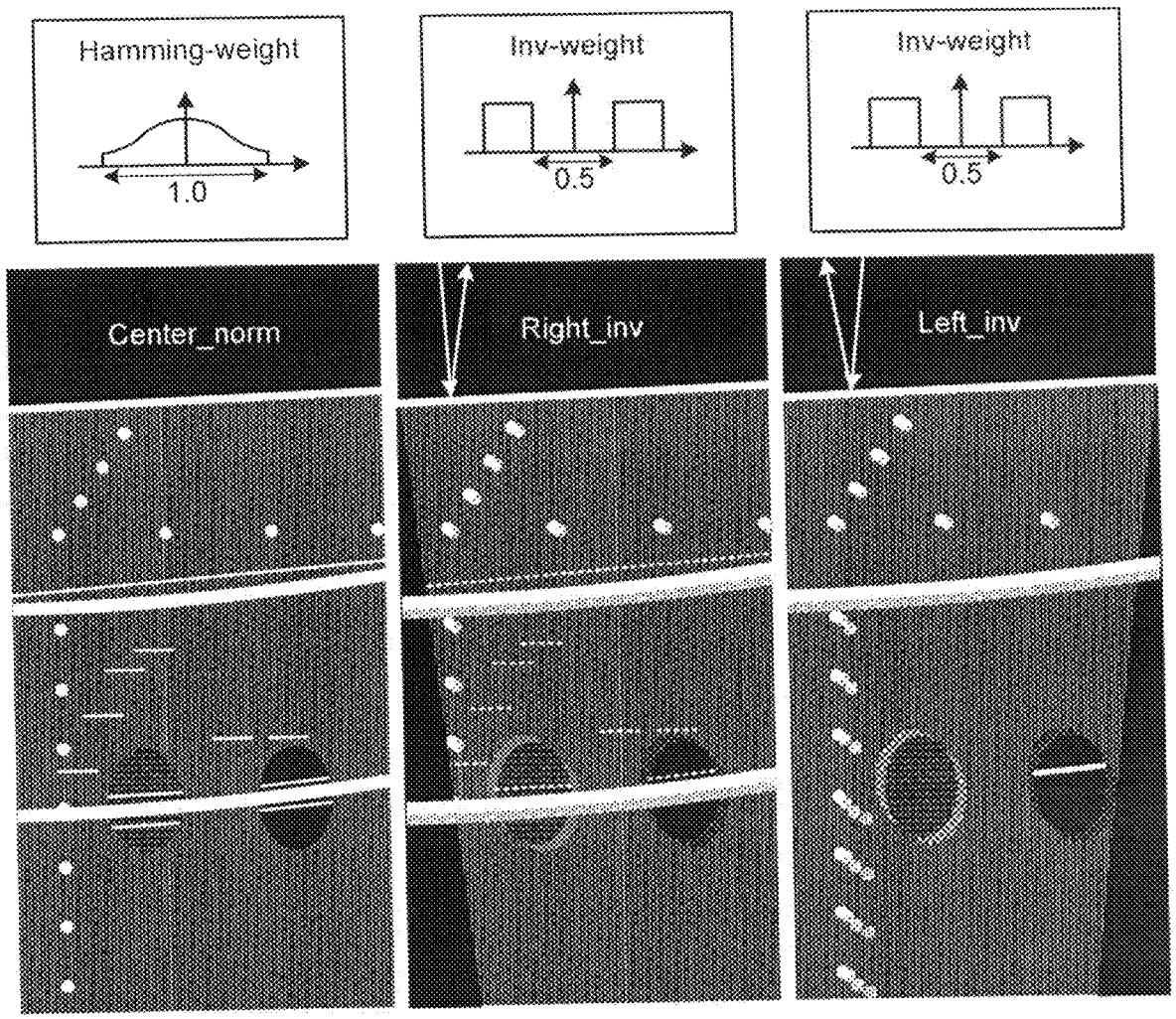
FIG. 23 is a diagram (4) for explaining the third embodiment.

A reason why data acquired by the normal apodization when deflected rightward and leftward can be used as input sources of the second coefficient distribution as the first case is explained using FIG. 22 and FIG. 23. FIG. 22 and FIG. 23 indicate a result of imaging a phantom covered with water on a surface thereof with deflection angles in three directions of a front direction and right and left directions to acquire a B-mode image of THI including a specular reverberation component. "Center_norm" shown in FIG. 22 and FIG. 23 is B-mode image data acquired by performing ultrasonic wave transmission/reception in the front direction (deflection angle: 0 degrees), and by performing the normal apodization applying the aperture function of the hamming window as the normal aperture function.

Furthermore, "Right_norm" shown in FIG. 22 is B-mode image data acquired by performing ultrasonic wave transmission/reception in the right direction, and by performing the normal apodization applying the aperture function of the hamming window as the normal aperture function. Moreover, "Left_norm" shown in FIG. 22 is B-mode image data acquired by performing ultrasonic wave transmission/reception in the left direction, and by performing the normal apodization applying the aperture function of the hamming window as the normal aperture function. Furthermore, "Right_inv" shown in FIG. 23 is B-mode image data acquired by performing ultrasonic wave transmission/reception in the right direction, and by performing the inverse apodization applying the aperture function in which the center portion is zero as the inverse aperture function. Moreover, "Left_inv" shown in FIG. 23 is B-mode image data acquired by performing ultrasonic wave transmission/reception in the left direction, and by performing the inverse apodization applying the aperture function in which the center portion is zero as the inverse aperture function. That is, "Right_inv" and "Left_inv" shown in FIG. 23 are image data that are acquired by the fixed apodization.

In one example shown in FIG. 22 and FIG. 23, a surface of the phantom is slightly inclined toward an upper right direction. Therefore, it is shown that the inclination at which reverberation echoes are displayed of a reflected wave of a single reverberation and a reflected wave of a double reverberation between the phantom surface and the probe surface increases as the depth increases with elongation of respective paths (propagation distance of echoes). When "Right_norm" and "Left_norm" are compared, the reverberation component is smaller in "Left_norm". Particularly, in "Left_norm", the double reverberation echo shown at a deep portion of the "Right_norm" is reduced to the extent that it is hardly observed. This is caused by a fact that a position at which phases of reverberation components are matched is shifted toward a left end direction of the aperture a weight of which is small in the normal aperture function with elongation of a path because the inclination of the phantom surface and the direction of the deflection angle are opposite to each other. Moreover, as for the double reverberation component, it is regarded that a reception position of the double reverberation echo falls outside the reception aperture, so that it is not received, and therefore, it is not viewed. To the contrary, in "Right_norm", it is regarded that because the inclination of the phantom surface and the direction of the deflection angle are identical, the reverberation component is received inside the reception aperture and the reverberation component becomes relatively large. However, a reverberation artifact of "Right_norm" is reduced lower than "Center_norm".

On the other hand, when "Right_inv" and "Left_inv" shown in FIG. 23 and "Left_norm" and "Right_norm" shown in FIG. 22 are compared, it is shown that an image in the inverse apodization has a larger reverberation echo than an image in the normal apodization both when deflected rightward and deflected leftward. This is because a region in which phases of reverberation components match is shifted from the aperture center portion at which the weight is zero due to rightward and leftward deflection, the component is received in a region of the end portion having a weight. Furthermore, as shown in FIG. 23, also in the inverse apodization, a reverberation component of "Right_inv" in which the inclination of the phantom surface and the deflection angle are in the same direction is larger than that of "Left_inv". As described, when deflected, and when the normal apodization by the normal aperture function in which the weight at the aperture end portion is smaller than the weight at the aperture center portion is applied, a reverberation component is smaller than that when the fixed inverse apodization is applied.

Therefore, in terms of simplification of processing, it is preferable that an input source to acquire the second coefficient distribution be acquired by the normal apodization.

The second case is explained. In the second case, data used to calculate the second coefficient distribution by the calculating unit 152 is data that is generated based on the inverse aperture function. Specifically, in the second case, data used to calculate the second coefficient distribution by the calculating unit 152 is data that is generated based on the shifted inverse aperture-function explained in the second embodiment. For example, the acquiring unit 151 acquires B-mode image data "L_Inv(x, y)" and "R_Inv(x, y)" that are acquired by the shifted inverse apodization using the shifted aperture function, as "L(x, y)" and "R(x, y)" as shown in FIG. 21B. The calculating unit 152 then calculates the second coefficient distribution from mean image data of "L_Inv(x, y)" and "R_Inv(x, y)".

As explained in the second embodiment, by performing the shifted inverse apodization based on a direction of ultrasonic wave transmission/reception, the multiplex reducing effect can be obtained even when deflected. Therefore, in the second case, by using data acquired in the shifted inverse apodization as the data to calculate the second coefficient distribution, the second coefficient distribution that enables to preferably reduce a reverberation component of the center image data can be acquired. The shifted inverse apodization used in the second case may be either of the first pattern or of the second pattern.

The third case is explained. In the third case, data used to calculate the second coefficient distribution by the calculating unit 152 is data that is acquired by multiplying the first coefficient distribution. For example, in the third case, the calculating unit 152 calculates the first coefficient distribution from "L_Inv(x, y)" that is acquired by the shifted inverse apodization, and the multiplying unit 153 multiplies "L_Norm(x, y)" by the first coefficient distribution, and the acquiring unit 151 acquires "OL_N(x, y)" that is output data of the multiplying unit 153 as shown in FIG. 21C. Moreover, for example, the calculating unit 152 calculates the first coefficient distribution from "R_Inv(x, y)" that is acquired by the shifted inverse apodization, and the multiplying unit 153 multiplies "R_Norm(x, y)" by the first coefficient distribution, and the acquiring unit 151 acquires "OR_N(x, y)" that is output data of the multiplying unit 153 as shown in FIG. 21C. Subsequently, the calculating unit 152 calculate the second coefficient distribution from mean image data of "OL_N(x, y)" and "OR_N(x, y)". The shifted inverse apodization used in the third case may be either of the first pattern or of the second pattern explained in the second embodiment. Furthermore, the normal apodization used in the second case may be performed using the shifted normal aperture-function explained in the second embodiment.

In the third case, by using output data obtained as a result of multiplication of the first coefficient distribution that is acquired by the shifted inverse apodization and the normal apodization as data used to calculate the second coefficient distribution, it is possible to acquire the second coefficient distribution that enables to reduce a reverberation component of the center image data.

Figure 24:
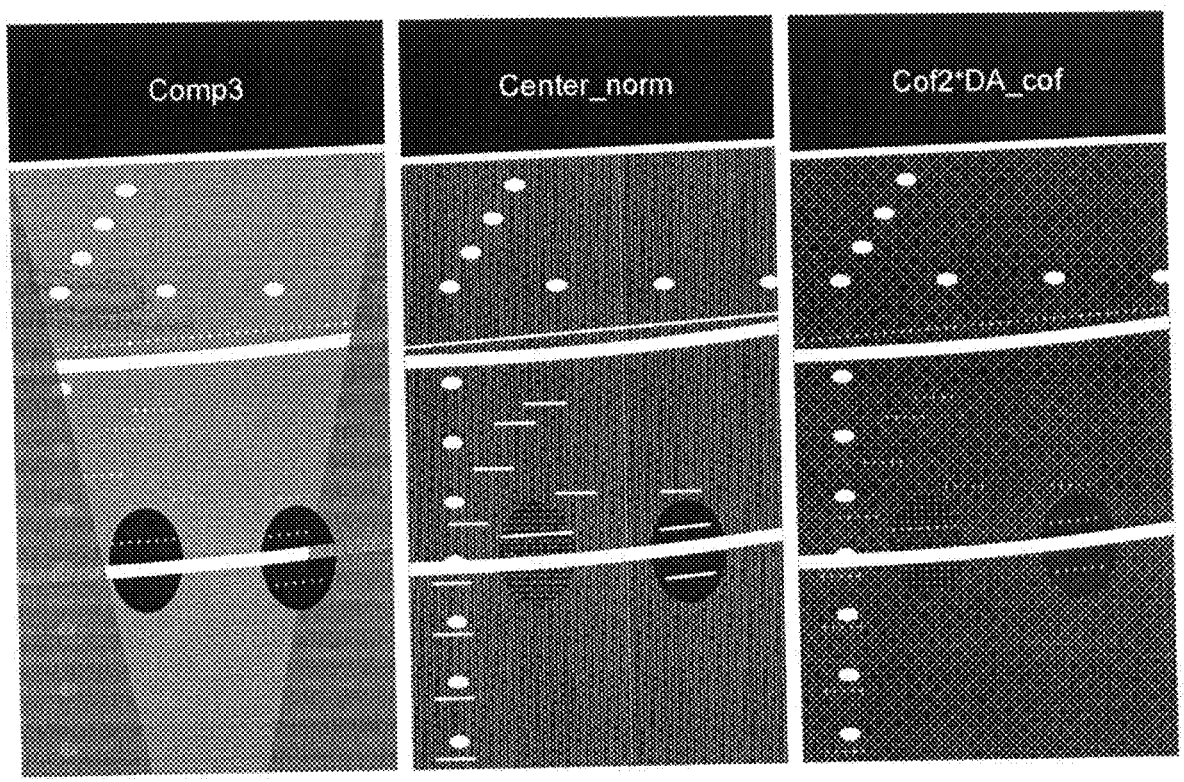
FIG. 24 is a diagram (5) for explaining the third embodiment.

FIG. 24 indicates a result when the first case described above is applied. FIG. 24 shows a result of imaging a phantom covered with water on a surface thereof in a state in which the phantom surface is slightly inclined toward an upper right direction to acquire a B-mode image of THI including a specular reverberation component. "Comp3" shown in FIG. 24 is an image obtained by compounding "Norm(x, y)", "L_Norm(x, y)", and "R_Norm(x, y)" in three directions, for example, by signal averaging. Furthermore, "Center_norm" shown in FIG. 24 is "Norm(x, y)". Moreover, "Cof2*DA_cof" shown in FIG. 24 is output image by the first case.

As shown in FIG. 24, in "Norm(x, y)" indicated by "Center_norm", the granularity of speckles is clear, and wires indicated by white ovals are precisely drawn, and the lateral resolution is high. On the other hand, in "Comp3" that is acquired by conventional compounding, although a reverberation component is lowest, the granularity of speckles is deteriorated, and the wires are drawn thick, and the lateral resolution is degraded. Furthermore, in "Cof2*DA_cof" that is acquired by processing of the present embodiment, a reverberation component is reduced compared to "Norm(x, y)", and the width of drawn wire is equivalent to "Norm(x, y)". Moreover, the granularity of speckles is also close to "Norm(x, y)" in "Cof2*DA_cof" compared to "Comp3".

In the above, a representative example in which a coefficient distribution is calculated using mean image data of left-deflected image data and right-deflected image data of either case out of the first case to the third case, applying three directions (±θ degrees, 0 degrees) as the deflection angles has been given. Note that "inclined deflected image data" to calculate the second coefficient distribution that enables to reduce reverberation independently of the first coefficient distribution may be deflected image data deflected in either one direction of right or left. For example, the calculating unit 152 may calculate the second coefficient distribution "cof2(x, y)" by substituting "L(x, y)" into Equation 2.

However, a structure to be a reverberation source inside a scanning region of the subject P can be inclined, for example, relative to the direction of arrangement of transducers. Accordingly, to obtain a robust reverberation reducing effect using the second coefficient distribution, it is preferable that the mean image data of the left-deflected image data and the right-deflected image data be used as described above. As shown in FIG. 20, for mean image data of a left side region other than a overlapped region, left-deflected image data is used, and for mean image data of a right side region other than the overlapped region, right-deflected image data is used, and even in such a case, by a synergistic effect of the first coefficient distribution and the second coefficient distribution, output image data in which reverberation is reduced and the lateral resolution and the sensitivity are maintained can be acquired.

Furthermore, in the third embodiment, the number of directions of the deflection angles may be increased to five or seven. In such a case, "(a): a method of increasing the number of addition direction of mean image data, "(b): a method of using image data obtained by performing compounding processing (for example, weighting processing) on multiple pieces of image data including front image data as the center image data", and "(c): a method of combining (a) and (b) can be performed.

Figure 25A:
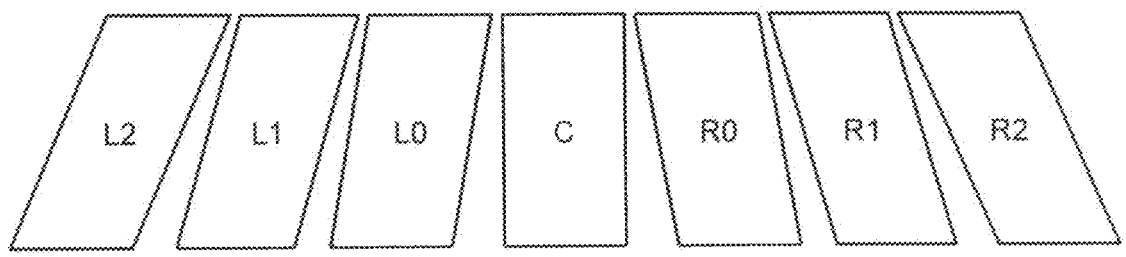
FIGS. 25A, 25B, 25C, and 25D are diagrams (6) for explaining the third embodiment.

One example in which the above method is applied when the number of direction is "seven" is explained using FIGS. 25A, 25B, 25C, and 25D. In FIG. 25A, image data in seven directions generated by frame sequence of deflection angles "$+\theta_2$ degrees, $+\theta_1$ degrees, $+\theta$ degrees, 0 degrees, $-\theta$ degrees, $-\theta_1$ degrees, $-\theta_2$ degrees ($\theta_2 > \theta_1 > 0$)" are indicated as "L2, L1, L0, C, R0, R1, R2".

Figure 25B:
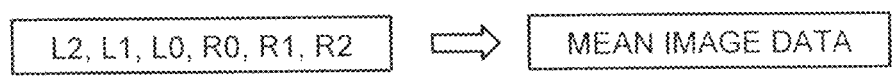

In such a case, for example, the calculating unit 152 or the image generating unit 14 generates mean image data from six pieces of image data of "L2, L1, L0, R0, R1, R2", to calculate the second coefficient distribution as shown in FIG. 25B. In such a case, the multiplying unit 153 multiplies "C" by the first coefficient distribution and the second coefficient distribution.

Figure 25C:
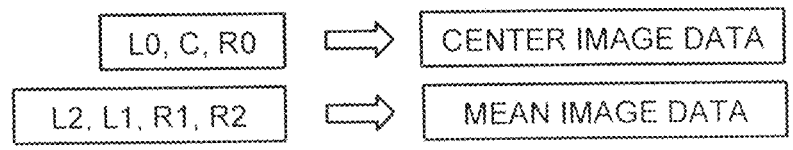

Alternatively, for example, the multiplying unit 153 or the image generating unit 14 performs weighting addition on "L0, C, R0" as shown in FIG. 25C, to generate center image data. Moreover, for example, the calculating unit 152 or the image generating unit 14 generates mean image data from "L2, L1, R1, R2" as shown in FIG. 25C, to calculate the second coefficient distribution.

Figure 25D:
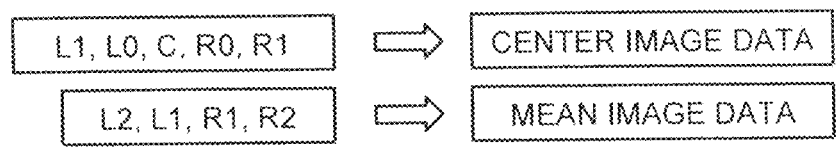

Alternatively, image data used for mean image data may be used also for the center image data. For example, the multiplying unit 153 or the image generating unit 14 performs weighting addition on "L1, L0, C, R0, R1" to generate the center image data as shown in FIG. 25D. Furthermore, for example the calculating unit 152 or the image generating unit 14 generates mean image data from "L2, L1, R1, R2", to calculate the second coefficient distribution as shown in FIG. 25D. Also when these application examples are performed, by a synergistic effect of the first coefficient distribution and the second coefficient distribution, output image data in which reverberation is reduced and the lateral resolution and the sensitivity are maintained can be acquired.

Note that the frame rate does not change from that at normal scanning of normal B-mode scanning even in the conventional method in which compounding processing is performed by frame sequence, or in the method according to the third embodiment in which multiplication processing using the first coefficient distribution and the second coefficient distribution is performed by frame sequence. However, in both of the methods, because the corresponding number of frames to the number of directions are used for processing, the responsivity in change of images to movement of the ultrasound probe 1, movement of the subject P caused by respiration, and the like is tend to be degraded as the number of directions increases. On the other hand, in both of the methods, the reverberation reducing effect becomes higher as the number of directions increases.

Accordingly, in the method according to the third embodiment, a tradeoff between the responsivity and the reverberation reducing effect occurs according to the set number of directions. Therefore, it is preferable, in the third embodiment, that candidate sets of the number of directions be prepared in advance so that setting of "the overall number of directions" and "the number of directions used for generation processing of mean image data and the number of directions used for generation processing of center image data" is configurable by an operator according to a use. In such a case, an operator selects a desirable setting from candidate sets displayed, for example, on GUI.

As described above, in the third embodiment, for example, the second coefficient distribution is acquired from deflected image data acquired by frame sequence, and data that is obtained by multiplying front image data without deflection acquired by frame sequence by the first coefficient distribution and the second coefficient distribution is output as B-mode image data. Thus, in the third embodiment, it is possible to acquire a higher quality image in which reverberation is further reduced than images acquired in the first embodiment and the second embodiment.

In the third embodiment, as a modification, data that is obtained by compounding "image data with multiple deflection angles acquired by multiplication processing with the first coefficient distribution" explained in the third case may be acquired as an output image. For example, in the third embodiment, as a modification, data obtained by compounding "OL_N(x, y)" and "OR_N(x, y)" used in the third case and "O_N(x, y)" that is acquired in the first embodiment and the second embodiment by signal averaging or weighting addition may be acquired as an output image. In a compound image in this modification, although the lateral resolution and the granularity of speckles are degraded by the compounding processing, a reverberation component is reduced by the multiplication processing with the first coefficient distribution.

Fourth Embodiment

In the fourth embodiment, a case in which the reverberation reducing effect is further enhanced by using a third coefficient distribution that is independently acquired of the first coefficient distribution "cof1(x, y)" explained in the first embodiment or the second embodiment is explained using FIG. 26A to FIG. 26D, and the like. FIG. 26A to FIG. 26D are diagrams for explaining the fourth embodiment.

The acquiring unit 151 according to the fourth embodiment further acquires a reception signal group that is constituted of reception signals with various deflection angles generated by ultrasonic scanning including a deflection angle of a predetermined direction (that is, the deflection angle of 0 degrees) in which deflection angles in ultrasonic wave transmission/reception are varied among rates and that is performed to acquire multiple reception signals explained in the first embodiment or the second embodiment. That is, in the fourth embodiment, ultrasonic scanning in which deflection angles are varied by the rate sequence explained using FIG. 3B is performed.

The calculating unit 152 according to the fourth embodiment further calculates a third coefficient (third coefficient distribution) using at least one reception signal with a deflection angle in a direction other than the predetermined direction from the reception signal group. Subsequently, the multiplying unit 153 according to the fourth embodiment multiplies a reception signal with the deflection angle of the predetermined direction, or a signal that is obtained by compounding reception signals of respective deflection angles of multiple directions including the predetermined direction by the first coefficient and the third coefficient (the first coefficient distribution and the third coefficient distribution). Processing explained below is applicable to various kinds of signals (an RF signal, an IQ signal, an amplitude signal, and an image signal) that are regarded as reception signals in the first embodiment.

In the rate sequence, to acquire a signal of a single reception scan line, ultrasonic wave transmission/reception with various deflection angles relative to a direction of this reception scan line as the center is performed more than once. For example, by control of the control unit 18, the transceiving unit 11 causes the ultrasound probe 1 to perform ultrasonic wave transmission/reception in three directions (deflection angles: 0 degrees, +θ degrees, −θ degrees) in a rate unit. Thus, three reception signals with different deflection angles are acquired. The predetermined direction described above is the direction of the deflection angle of "0 degrees". The direction of the deflection angle of "0 degrees" is a direction to acquire "0_N(x, y)" explained in the first embodiment. Subsequently, the acquiring unit 151 acquires these three reception signals.

Figure 26A:
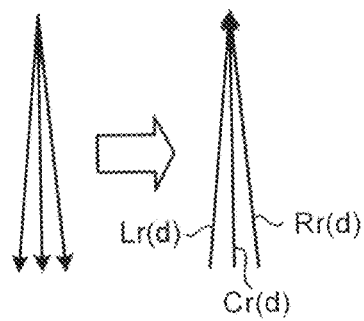
FIGS. 26A, 26B, 26C and 26D are diagrams for explaining a fourth embodiment.

"Lr(d)" and "Rr(d)" shown in FIG. 26A are a left-deflected reception signal and a right-deflected reception signal in which a reverberation component is reduced by inclined transmission and reception. Moreover, "Cr(d)" shown in FIG. 26A is a reception signal in the direction of the deflection angle of "0 degrees", and is a front signal (center signal) that enables to acquire an image with high lateral resolution and sensitivity but has a possibility that a reverberation component is included more than the left-deflected reception signal and the right-deflected reception signal. "(d)" indicates a position in a depth direction (direction of a reception scan line) in a reception signal.

In FIGS. 26A, 26B, 26C, and 26D, a reception signal that is finally acquired from a reception signal of the deflection angle of 0 degrees by the first coefficient distribution in the normal/inverse apodization is "Cr(d)". That is, "Cr(d)" is a reception signal that is obtained by dividing a reception signal with the deflection degree of "0 degrees" into two systems, and by multiplying a reception signal that is obtained from a system of the normal apodization by the first coefficient distribution that is calculated from a reception signal obtained in the system of the inverse apodization. When cof1(x, y) is acquired in the fourth embodiment, as an exponentiation value "α" described above, it is preferable that a value of about ⅛ to ⅙, which is half of about ¼ to ⅓, be set.

Figure 26B:
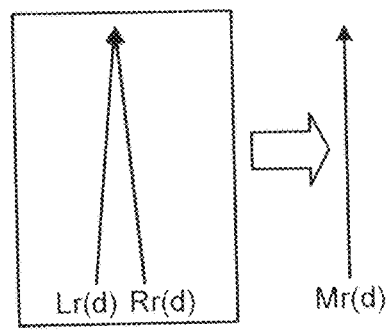
Figure 26C:
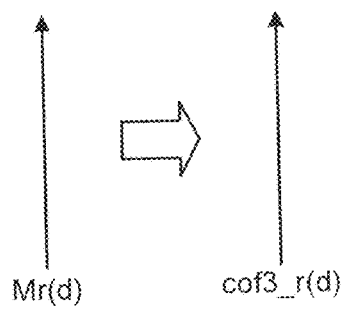
Figure 26D:
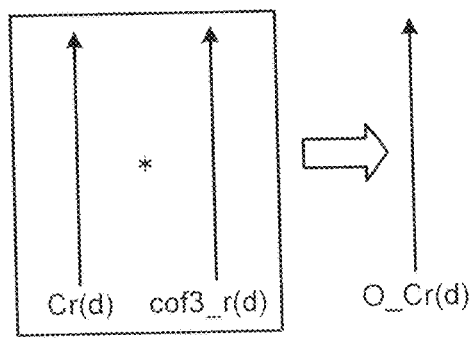

In FIGS. 26B, 26C, and 26D, a case in which the calculating unit 152 calculates a third coefficient distribution with "Lr(d)" and "Rr(d)" as subjects of processing, and the multiplying unit 153 multiplies "Cr(d)" by the third coefficient distribution is exemplified. The processing of multiplying "Cr(d)" by the third coefficient distribution is equivalent to the processing of multiplying a reception signal that is acquired in the system of the normal apodization at the deflection angle of "0 degrees" by the first coefficient distribution and the third coefficient distribution.

As for "Lr(d)" and "Rr(d)" that are input data to calculate the third coefficient distribution, it is effective to select data in which occurrence of multiplexing is small. The three cases explained in the third embodiment can be applied, when determining what kind of data is to be selected as "Lr(d)" and "Rr(d)". That is, in the first case according to the fourth embodiment, data that is generated based on the normal aperture function is used as the data ("Lr(d)" and "Rr(d)") used to calculated the third coefficient distribution by the calculating unit 152. Moreover, in the second case according to the fourth embodiment, data that is generated based on the shifted inverse aperture-function explained in the second embodiment is used as the data ("Lr(d)" and "Rr(d)") used to calculated the third coefficient distribution by the calculating unit 152. Furthermore, in the third case according to the fourth embodiment, data that is acquired by performing multiplication processing of the first coefficient distribution to which the normal apodization and the shifted inverse apodization are applied n is used as the data ("Lr(d)" and "Rr(d)") to used calculated the third coefficient distribution by the calculating unit 152.

Moreover, also in the fourth embodiment, it is preferable that at least data that is used for calculation of the third coefficient distribution by the calculating unit 152 is preferable to be data for which a non-linear component is extracted to prevent mixing of side lobe components. In such a case, also data to which the multiplying unit 153 multiplies by the third coefficient distribution is preferable to be data for which a non-linear component is extracted in terms of a circuit configuration.

When the acquiring unit 151 acquires the data described above, the calculating unit 152 acquires mean signal "Mr(d)" of "Lr(d)" and "Rr(d)" as shown in FIG. 26B. Specifically, the calculating unit 152 acquires "Mr(d)" by Equation 17 below.

$$Mr(d)=(Lr(d)+Rr(d))/2 \qquad (17)$$

The calculating unit 152 then calculates the third coefficient distribution/"cof3_r(d)" to be given to "Cr(d)" at the depth direction "d" from the mean signal (Mr(d)". Specifically, the calculating unit 152 calculates "cof3_r(d)" by Equation 18 below.

$$\left. \begin{array}{l} cof3\_r(d) = (Mr(d)/\beta 3)^{\alpha 3} \\ (\text{Where when } Mr(d) > \beta 3, cof3\_r(d) = 1.0) \end{array} \right\} \qquad (18)$$

In above Equation 18, it is defined that an "α3-th power" of a value that is obtained by dividing Mr(d) by "β3" is "cof3_r(d)". Moreover, in above Equation 18, it is defined that when a value obtained by dividing Mr(d) by "β3" is larger than "1", "cof3_r(d)" is "1". "α3, β3" are values set in advanced as explained in the first embodiment and the third embodiment. Specifically, "β3" signifies an upper level of an output reception signal, and is set to a level equal to or lower than the maximum value "max" of a reception signal. It is preferable that "β3" be set to a level of about 70% to 80% of "max". Furthermore, it is preferable that "α3" be set to a value of about ⅛ to ⅙ as indicated in the third embodiment. An advantage of calculating the third coefficient distribution using a function including an arithmetic processing in which the calculating unit 152 exponentiates an input value as in Equation 18 is similar to the reason explained in the calculation processing of the first coefficient distribution "cof1(x, y)".

Subsequently, the multiplying unit 153 multiplies "Cr(d)" by the third coefficient distribution "cof3_r(d)" as shown in FIG. 26D, and outputs an output reception signal "O_Cr(d)". Specifically, the multiplying unit 153 performs arithmetic processing of Equation 19 below.

$$O\_Cr(d)=Cr(d)*cof3\_r(d) \qquad (19)$$

The data processing unit 15 performs the above processing for all of reception scan lines, to output an output reception signal of one frame. By control of the control unit 18, the image generating unit 14 generates output image data from an output reception-signal group of one frame. The monitor 2 displays output image data by control of the control unit 18. The output image data is to be high quality image data in which reverberation is reduced and the lateral resolution and the sensitivity are maintained by a synergistic effect of the first coefficient distribution and the third coefficient distribution. Also in the fourth embodiment, the control unit 18 may compensate, using a predetermined LUT, the display dynamic range and the gain at the time of displaying output image data so that image data on which the multiplication processing is not performed and the display dynamic range and the gain on appearance are equivalent.

In the fourth embodiment also, as explained in the third embodiment, one inclined reception signal (for example, "Lr(d)") may be used to calculate the coefficient distribution. Furthermore, also in the fourth embodiment, as explained in the third embodiment, the number of directions of deflection angle may be increased to five or seven.

One example of processing performed when the number of direction is "seven" is explained. In the following, image data in seven directions generated by frame sequence of deflection angles "$+\theta_2$ degrees, $+\theta_1$ degrees, $+\theta$ degrees, 0 degrees, $-\theta$ degrees, $-\theta_1$ degrees, $-\theta_2$ degrees ($\theta_2 > \theta_1 > 0$)" are indicated as "Lr2, Lr1, Lr0, Cr, Rr0, Rr1, Rr2".

In such a case, for example, the calculating unit 152 generates mean signal from six reception signals of "Lr2, Lr1, Lr0, Rr0, Rr1, Rr2", to calculate the third coefficient distribution. In such a case, the multiplying unit 153 multiplies "Cr" by the third coefficient distribution.

Alternatively, for example, the multiplying unit 153 performs weighting addition on "Lr0, Cr, Rr0", to generate a center signal. Moreover, for example, the calculating unit 152 generates a mean signal from "Lr2, Lr1, Rr1, Rr2", to calculate the third coefficient distribution.

Alternatively, for example, the multiplying unit 153 performs weighting addition on "Lr1, Lr0, Cr, Rr0, Rr1", to generate a center signal. Furthermore, for example, the calculating unit 152 generates a mean signal from "Lr2, Lr1, Rr1, Rr2", to calculate the third coefficient distribution. Also when these application examples are performed, by a synergistic effect of the first coefficient distribution and the third coefficient distribution, it is possible to acquire an output reception signal enabling to generate output image data in which a reverberation component is reduced and the lateral resolution and the sensitivity are maintained.

When the above application examples are performed, in the fourth embodiment, similarly to the third embodiment, it is preferable that candidate sets of the number of directions be prepared in advance so that setting of "the overall number of directions" and "the number of directions used for generation processing of a mean signal and the number of directions used for generation processing of a center signal" is configurable by an operator according to a use.

As described above, in the fourth embodiment, by performing the multiplication processing using the first coefficient distribution and the third coefficient distribution, it is possible to acquire a higher quality image in which reverberation is further reduced than images acquired in the method in which the spatial compounding among rates explained in using FIG. 3B is performed, or in the first embodiment and the second embodiment.

In the fourth embodiment, similarly to the modification of the third embodiment, an output image may be acquired by data obtained by compounding "reception signals with multiple deflection angles acquired by multiplication processing with the first coefficient distribution" of the third case.

Fifth Embodiment

In the fifth embodiment, a case in which the reverberation reducing effect is further enhanced by using a fourth coefficient distribution that is independently acquired of the first coefficient distribution "cof1(x, y)" explained in the first embodiment or the second embodiment is explained using FIG. 27A to FIG. 27D, and the like. FIG. 27A to FIG. 27D are diagrams for explaining the fifth embodiment.

The acquiring unit 151 according to the fifth embodiment further acquires a simultaneous reception-signal group that is constituted of simultaneous reception signals with various deflection angles including a deflection angle of generated by ultrasonic scanning in which reflected waves of reception deflection angles are received by parallel simultaneous reception for transmission ultrasonic waves, and that is ultrasonic scanning in which a predetermined direction (that is, the deflection angle of 0 degrees) is included in the reception deflection angles performed to acquire multiple reception signals explained in the first embodiment or the second embodiment. That is, in the fifth embodiment, ultrasonic scanning in which deflection angles are varied in the parallel simultaneous reception explained using FIG. 3A is performed.

The calculating unit 152 according to the fifth embodiment further calculates a fourth coefficient (fourth coefficient distribution) using at least one simultaneous reception signal with a deflection angle in a direction other than the predetermined direction from the simultaneous reception signal group. Subsequently, the multiplying unit 153 according to the fifth embodiment multiplies a simultaneous reception signal with the deflection angle of the predetermined direction, or a signal that is obtained by compounding simultaneous reception signals of respective deflection angles of multiple directions including the predetermined direction by the first coefficient and the fourth coefficient (the first coefficient distribution and the fourth coefficient distribution). Processing explained below is applicable to various kinds of signals (an RF signal, an IQ signal, an amplitude signal, and an image signal) that are regarded as reception signals in the first embodiment.

In parallel simultaneous reception, when acquiring a signal of a single reception scan line, multiple reception signals (simultaneous reception signals) reception with various deflection angles relative to a direction of this reception scan line as the center can be acquired simultaneously. Therefore, in the fifth embodiment, by applying the processing explained in the fourth embodiment to these multiple simultaneous reception signals, a signal in the direction of a reception scan line to be a final output is acquired.

For example, by control of the transceiving unit 11 through the control unit 18, the ultrasound probe 1 transmits an ultrasonic beam in a direction of the deflection angle of "0 degrees", and receives reflected waves of three directions (deflection angles: 0 degrees, $+\theta$ degrees, $-\theta$ degrees) simultaneously. Thus, three simultaneous reception signals with different deflection angles are acquired. The predetermined direction described above is the direction of the deflection angle of "0 degrees", which is the direction of the reception scan line. The direction of the deflection angle of "0 degrees" is a direction to acquire "0_N(x, y)" explained in the first embodiment. Subsequently, the acquiring unit 151 acquires these three reception signals.

Figure 27A:
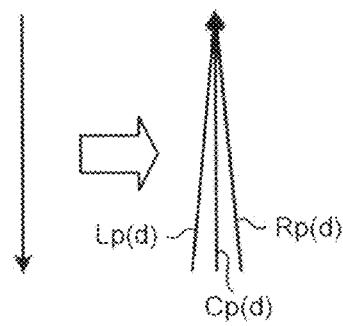
FIGS. 27A, 27B, 27C, and 27D are diagrams for explaining a fifth embodiment.

"Lp(d)" and "Rp(d)" shown in FIG. 27A are a left-deflected simultaneous-reception signal and a right-deflected simultaneous-reception signal in which a reverberation component is reduced by inclined transmission and reception. Moreover, "Cp(d)" shown in FIG. 27A is a simultaneous reception signal in the direction of the deflection angle of "0 degrees", and is a front signal (center signal) that enables to acquire an image with high lateral resolution and sensitivity but has a possibility that a reverberation component is included more than the left-deflected simultaneous-reception signal and the right-deflected simultaneous-reception signal. "(d)" indicates a position in a depth direction (direction of a reception scan line) in a simultaneous reception signal.

In FIGS. 27A to 27D, a reception signal that is finally acquired from a simultaneous reception signal of the deflection angle of 0 degrees by the first coefficient distribution in the normal/inverse apodization is "Cp(d)". That is, "Cp(d)" is a reception signal that is obtained by dividing a simultaneous reception signal with the deflection degree of "0 degrees" into two systems, and by multiplying a reception signal that is obtained from a system of the normal apodization by the first coefficient distribution that is calculated from a reception signal obtained in the system of the inverse apodization. When cof1(x, y) is acquired in the fifth embodiment, as an exponentiation value "α" described above, it is preferable that a value of about ⅛ to ⅙, which is half of about ¼ to ⅓, be set similarly to the third embodiment.

Figure 27B:
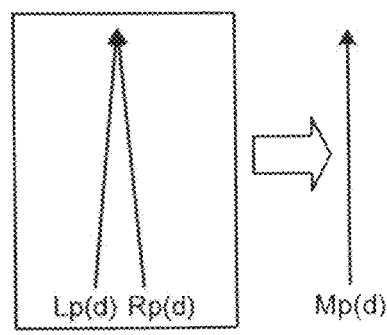
Figure 27C:
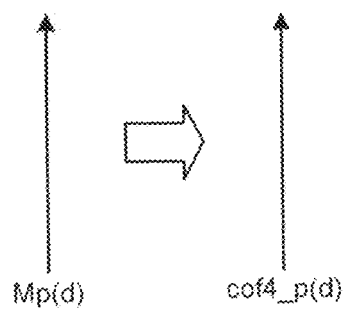
Figure 27D:
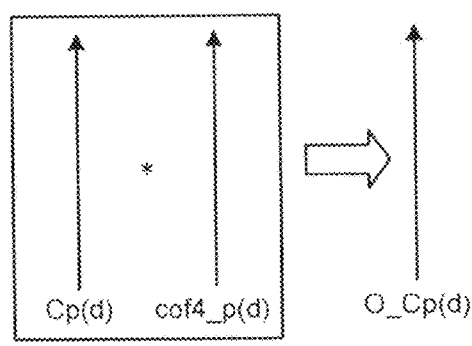

In FIGS. 27B to 27D, a case in which the calculating unit 152 calculates the fourth coefficient distribution with "Lp(d)" and "Rp(d)" as subjects of processing, and the multiplying unit 153 multiplies "Cp(d)" by the fourth coefficient distribution is exemplified. The processing of multiplying "Cp(d)" by the fourth coefficient distribution is equivalent to the processing of multiplying a reception signal that is acquired in the system of the normal apodization at the deflection angle of "0 degrees" by the first coefficient distribution and the third coefficient distribution.

As for "Lp(d)" and "Rp(d)" that are input data to calculate the fourth coefficient distribution, it is effective to select data in which occurrence of multiplexing is small. The three cases explained in the third embodiment can be applied when determining what kind of data is to be selected as "Lp(d)" and "Rp(d)". That is, in the first case according to the fifth embodiment, data that is generated based on the normal aperture function is used as the data ("Lp(d)" and "Rp(d)") used to calculate the fourth coefficient distribution by the calculating unit 152. Moreover, in the second case according to the fifth embodiment, data that is generated based on the shifted inverse aperture-function explained in the second embodiment is used as the data ("Lp(d)" and "Rp(d)") used to calculate the fourth coefficient distribution by the calculating unit 152. Furthermore, in the third case according to the fifth embodiment, data that is acquired by performing multiplication processing of the first coefficient distribution to which the normal apodization and the shifted inverse apodization are applied is used as the data ("Lp(d)" and "Rp(d)") used to calculate the third coefficient distribution by the calculating unit 152.

Moreover, also in the fifth embodiment, it is preferable that at least data that is used for calculation of the fourth coefficient distribution by the calculating unit 152 is preferable to be data for which a non-linear component is extracted to prevent mixing of side lobe components. In such a case, also data to which the multiplying unit 153 multiplies by the third coefficient distribution is preferable to be data for which a non-linear component is extracted in terms of a circuit configuration.

When the acquiring unit 151 acquires the data described above, the calculating unit 152 acquires mean signal "Mp(d)" of "Lp(d)" and "Rp(d)" as shown in FIG. 27B. Specifically, the calculating unit 152 acquires "Mp(d)" by Equation 20 below.

$$Mp(d)=(Lp(d)+Rp(d))/2 \quad (20)$$

The calculating unit 152 then calculates the fourth coefficient distribution "cof4_p(d)" to be given to "Cp(d)" at the depth direction "d" from the mean signal (Mp(d)". Specifically, the calculating unit 152 calculates "cof4_p(d)" by Equation 21 below.

$$\left.\begin{array}{l}cof4\_p(d) = (Mp(d)/\beta 4)^{\alpha 4} \\ (\text{Where when } Mp(d) > \beta 4, cof4\_p(d) = 1.0)\end{array}\right\} \quad (21)$$

In above Equation 21, it is defined that an "α4-th power" of a value that is obtained by dividing Mp(d) by "β4" is "cof4_p(d)". Moreover, in above Equation 21, it is defined that when a value obtained by dividing Mp(d) by "β4" is larger than "1", "cof4_p(d)" is "1". "α4, β4" are values set in advanced as explained in the first embodiment, the third embodiment, and the fourth embodiment. Specifically, "β4" signifies an upper level of an output reception signal, and is set to a level equal to or lower than the maximum value "max" of a reception signal. It is preferable that "β4" be set to a level of about 70% to 80% of "max". Furthermore, it is preferable that "α4" be set to a value of about ⅛ to ⅙ as indicated in the third embodiment. An advantage of calculating the fourth coefficient distribution using a function including an arithmetic processing in which the calculating unit 152 exponentiates an input value as in Equation 21 is similar to the reason explained in the calculation processing of the first coefficient distribution "cof1(x, y)".

Subsequently, the multiplying unit 153 multiplies "Cp(d)" by the fourth coefficient distribution as shown in FIG. 27D, and outputs an output reception signal "0 Cp(d)". Specifically, the multiplying unit 153 performs arithmetic processing of Equation 22 below.

$$O\_Cp(d)=Cp(d)*cof4\_p(d) \quad (22)$$

The data processing unit 15 performs the above processing for all of reception scan lines, to output an output reception signal of one frame. By control of the control unit 18, the image generating unit 14 generates output image data from an output reception-signal group of one frame. The monitor 2 displays output image data by control of the control unit 18. The output image data is to be a high quality image in which reverberation is reduced and the lateral resolution and the sensitivity are maintained by a synergistic effect of the first coefficient distribution and the fourth coefficient distribution. Also in the fifth embodiment, the control unit 18 may compensate, using a predetermined LUT, the display dynamic range and the gain at the time of displaying output image data so that image data on which the multiplication processing is not performed and the display dynamic range and the gain on appearance are equivalent.

In the fifth embodiment also, as explained in the third embodiment and the fourth embodiment, one inclined reception signal (for example, "Lp(d)") may be used to calculate the coefficient distribution. Furthermore, also in the fifth embodiment, as explained in the third embodiment and the fourth embodiment, the number of directions of deflection angles may be increased to five or seven.

One example of processing performed when the number of directions is "seven" is explained. In the following, simultaneous reception signals in seven directions of deflection angles "$+\theta_2$ degrees, $+\theta_1$ degrees, $+\theta$ degrees, 0 degrees, $-\theta$ degrees, $-\theta_1$ degrees, $-\theta_2$ degrees ($\theta_2 > \theta_1 > 0$)" are indicated as "Lp2, Lp1, Lp0, Cp, Rp0, Rp1, Rp2".

In such a case, for example, the calculating unit 152 generates a mean signal from six simultaneous reception signals of "Lp2, Lp1, Lp0, Rp0, Rp1, Rp2", to calculate the fourth coefficient distribution.

Alternatively, for example, the multiplying unit 153 performs weighting addition on "Lp0, Cp, Rp0", to generate a center signal. Moreover, for example, the calculating unit 152 generates a mean signal from "Lp2, Lp1, Rp1, Rp2", to calculate the fourth coefficient distribution.

Alternatively, for example, the multiplying unit 153 performs weighting addition on "Lp1, Lp0, Cp, Rp0, Rp1", to generate a center signal. Furthermore, for example, the calculating unit 152 generates a mean signal from "Lp2, Lp1, Rp1, Rp2", to calculate the fourth coefficient distribution. Also when these application examples are performed, by a synergistic effect of the first coefficient distribution and the fourth coefficient distribution, it is possible to acquire an output reception signal that enables to generate output image data in which reverberation is reduced and the lateral resolution and the sensitivity are maintained.

When the above application examples are performed, in the fifth embodiment, similarly to the third embodiment and the fourth embodiment, it is preferable that candidate sets of the number of directions be prepared in advance so that setting of "the overall number of directions" and "the number of directions used for generation processing of a mean signal and the number of directions used for generation processing of a center signal" is configurable by an operator according to a use.

As described above, in the fifth embodiment, by performing the multiplication processing using the first coefficient distribution and the fourth coefficient distribution, it is possible to acquire a higher quality image in which reverberation is further reduced than images acquired in the conventional method in which the spatial compounding is performed by parallel simultaneous reception, or in the first embodiment and the second embodiment.

In the fifth embodiment, similarly to the modifications of the third embodiment and the fourth embodiment, an output image may be acquired by data obtained by compounding "reception signals with multiple deflection angles acquired by multiplication processing with the first coefficient distribution" of the third case.

Sixth Embodiment

In a sixth embodiment, a case in which processing explained in the third embodiment to the fifth embodiment is combined to be performed is explained.

That is, in the scan mode of frame sequence explained in the third embodiment (hereinafter, first scan mode), a scan mode of rate sequence explained in the fourth embodiment (hereinafter, second scan mode), and a scan mode of parallel simultaneous reception explained in the fifth embodiment (hereinafter, third scan mode), each of deflection angles can be set independently. Therefore, the operation explained in the third embodiment to the fifth embodiment can be arbitrarily combined with the processing using the first coefficient distribution explained in the first and the second embodiments. This enables to achieve both the multiplex reducing effect and maintenance the lateral resolution and the sensitivity.

Moreover, when at least two out of the three kinds of scan modes are combined to be used, multiplication processing using a coefficient distribution acquired in each mode is performed at least in one of the scan modes, and a conventional method (compounding processing) may be performed in the rest of the scan mode. This also enables to achieve both the multiplex reducing effect and maintenance the lateral resolution and the sensitivity.

Therefore, for example, an ultrasonography apparatus according to the sixth embodiment is configured as below. The acquiring unit 151 according to the sixth embodiment has a function of acquiring the image data group explained in the third embodiment, the reception signal group explained in the fourth embodiment, and the simultaneous reception-signal group explained in the fifth embodiment, in addition to the data acquiring function explained in the first embodiment.

Furthermore, for example, the calculating unit 152 according to the sixth embodiment has a function of calculating the first coefficient distribution to the fourth coefficient distribution. Moreover, for example, the multiplying unit 153 according to the sixth embodiment has a multiplication function using the first coefficient distribution to the fourth coefficient distribution.

The control unit 18 according to the sixth embodiment controls to perform, when at least two out of the first scan mode, the second scan mode, and the third scan mode are used in combination, multiplication processing using a corresponding coefficient distribution and the first coefficient distribution on at least one data group out of multiple data groups that are acquired by the executed scan modes. Furthermore, the control unit 18 according to the sixth embodiment controls to perform, when a data group on which the multiplication processing is not performed is present, compounding processing on the data group. The control unit 18 according to the sixth embodiment causes the monitor 2 to display ultrasonic image data output by these control processing.

Processing performed in the sixth embodiment is explained below using FIG. 28 to FIG. 31. FIG. 28 to FIG. 31 are diagrams for explaining the sixth embodiment. Combination of scan modes and selection of processing in each scan mode are performed by various forms, such as a case in which an operator sets, and a case in which an operator selects from presets initially set. In the following, multiplication processing using a coefficient distribution other than the first coefficient distribution, and the first coefficient distribution is indicated as "M", and conventional compounding processing is indicated as "C".

Figure 28:
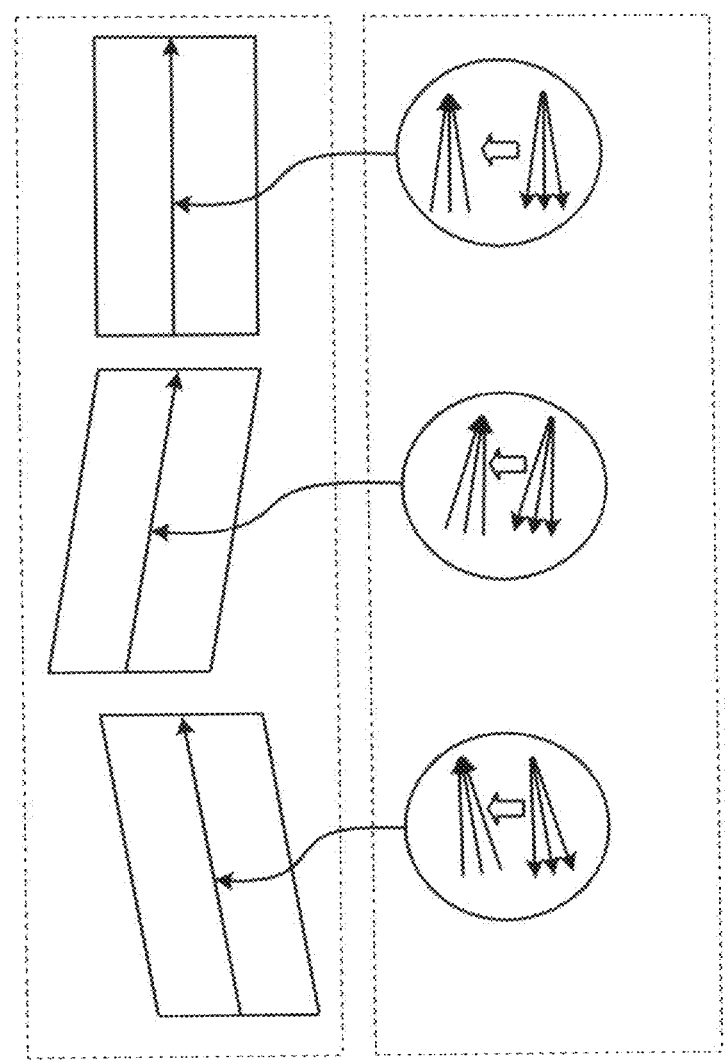
FIG. 28 is a diagram (1) for explaining a sixth embodiment.

First, a case in which the first scan mode and the second scan mode are used in combination is explained using FIG. 28. FIG. 28 shows a case in which three directions are set as deflection angles of entire image data in the first scan mode, and three transmission/reception directions are set when a reception signal of a single reception scan line in image data of respective directions is acquired in the second scan mode. When the first scan mode and the second scan mode are used in combination in the forms shown in FIG. 28, there are three pattern: a case in which the processing is performed with "the first scan mode: M, the second scan mode: M", a case in which the processing is performed with "the first scan mode: M, the second scan mode: C", and a case in which the processing is performed with "the first scan mode: C, the second scan mode: M".

Figure 29:
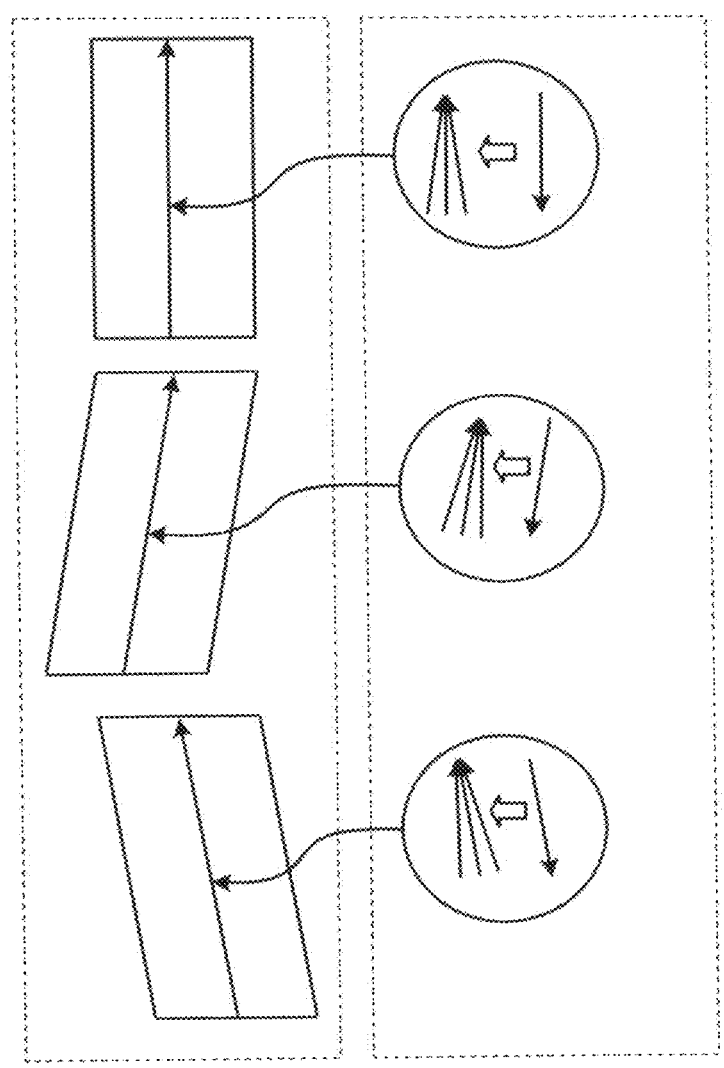
FIG. 29 is a diagram (2) for explaining the sixth embodiment.

Next, a case in which the first scan mode and the third scan mode are used in combination is explained using FIG. 29. FIG. 29 shows a case in which three directions are set as deflection angles of entire image data in the first scan mode, and three simultaneous reception directions are set when a reception signal of a single reception scan line in image data of respective directions is acquired in the third scan mode.

When the first scan mode and the third scan mode are used in combination in the forms shown in FIG. 29, there are three patterns: a case in which the processing is performed with "the first scan mode: M, the third scan mode: M", a case in which the processing is performed with "the first scan mode: M, the third scan mode: C", and a case in which the processing is performed with "the first scan mode: C, the third scan mode: M".

Figure 30:
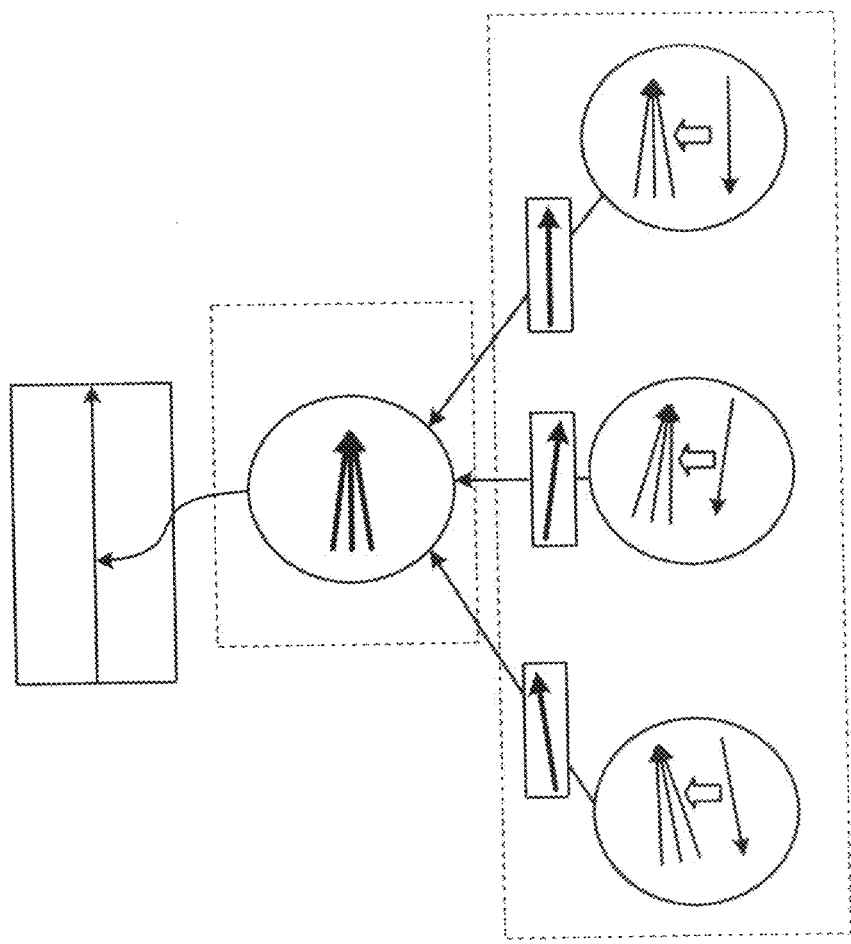
FIG. 30 is a diagram (3) for explaining the sixth embodiment.

Next, a case in which the second scan mode and the third scan mode are used in combination is explained using FIG. 30. FIG. 30 shows a case in which three transmission/reception directions are set when a reception signal of a single reception scan line in front image data of "0 degrees" in the second scan mode, and it is set that simultaneous reception signals deflected in three direction relative to each of these three transmission/reception direction as center are acquired in the third scan mode. When the second scan mode and the third scan mode are used in combination in the forms shown in FIG. 30, there are three patterns: a case in which the processing is performed with "the second scan mode: M, the third scan mode: M", a case in which the processing is performed with "the second scan mode: M, the third scan mode: C", and a case in which the processing is performed with "the second scan mode: C, the third scan mode: M".

Figure 31:
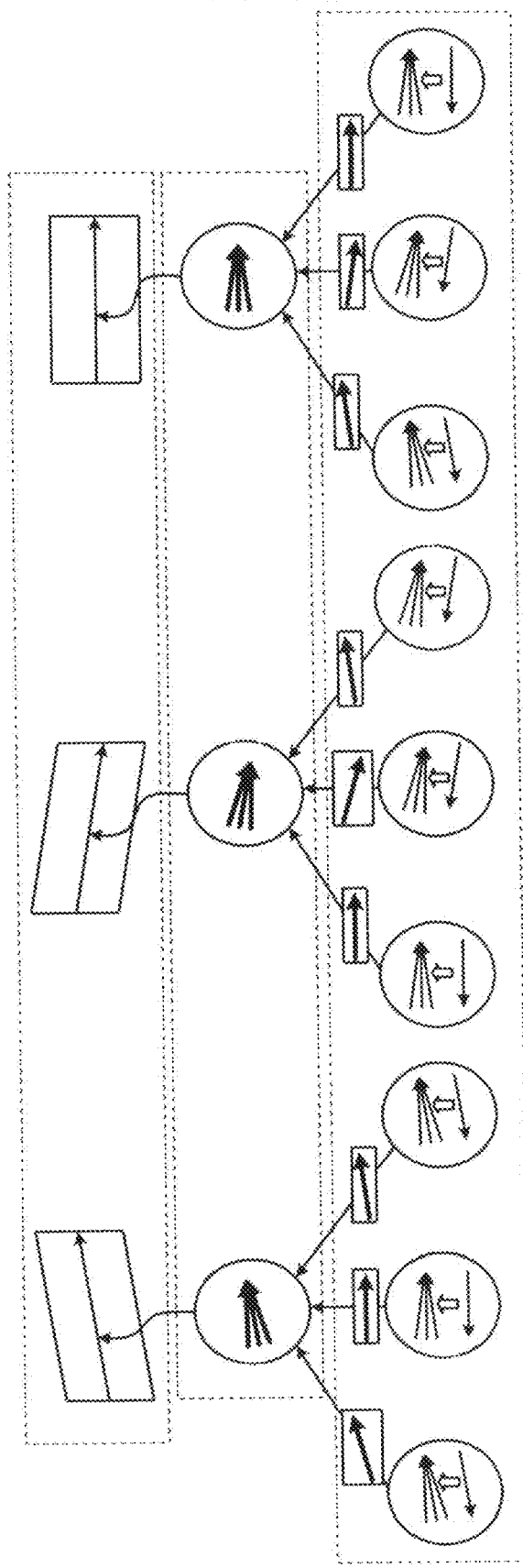
FIG. 31 is a diagram (4) for explaining the sixth embodiment.

Next, a case in which the first scan mode, the second scan mode, and the third scan mode are used in combination is explained using FIG. 31. FIG. 31 shows a case in which three directions are set as deflection angles of entire image data in the first scan mode, and three transmission/reception directions are set when a reception signal of a single reception scan line in image data of respective directions is acquired in the second scan mode. FIG. 31 further shows a case in which it is set that simultaneous reception signals deflected in three directions relative to each of the three transmission/reception direction of the second scan mode as center are acquired in the third scan mode.

When the first scan mode, the second scan mode, and the third scan mode are used in combination in the forms shown in FIG. 31, there are cases: a case in which the processing is performed with "the first scan mode: M, the second scan mode: M, the third scan mode: M", a case in which the processing is performed with "the first scan mode: M, the second scan mode: M, the third scan mode: C", a case in which the processing is performed with "the first scan mode: M, the second scan mode: C, the third scan mode: M", a case in which the processing is performed with "the first scan mode: C, the second scan mode: M, the third scan mode: M". Furthermore, when the first scan mode, the second scan mode, and the third scan mode are used in combination in the forms shown in FIG. 31, there are cases: a case in which the processing is performed with "the first scan mode: M, the second scan mode: C, the third scan mode: C", a case in which the processing is performed with "the first scan mode: C, the second scan mode: M, the third scan mode: C", and a case in which the processing is performed with "the first scan mode: C, the second scan mode: C, the third scan mode: M".

By performing either processing described above, it is possible to acquire a high quality image in which reverberation is reduced, and the lateral resolution and the sensitivity are maintained. The above is merely one example and, for example, when the first scan mode, the second scan mode, and the third scan mode are used in combination, seven directions may be set as deflection angles of entire image data in the first scan mode, and five transmission/reception directions may be set when a reception signal of a single reception scan line in image data of respective directions is acquired in the second scan mode, and it may be set that simultaneous reception signals deflected in further three directions relative to each of the five transmission/reception direction of the second scan mode as center are acquired in the third scan mode.

According to the sixth embodiment described above, on the precondition that the first coefficient distribution is used, the flexibility in image quality setting by combination of multiplication processing using various coefficient distributions other than the first coefficient distribution can be increased according to a demand for the image quality desired by an operator. Specifically, in the sixth embodiment, setting of the image quality that is determined by which factor is prioritized in the balance among the responsivity, the frame rate, the spatial resolution (lateral resolution), the sensitivity, and the reverberation component can be achieved by selecting from among setting candidate sets by an operator.

In the third embodiment to the sixth embodiment described above, a case in which a mean value of multiple directions is applied to an image signal having deflection or a reception signal having deflection at calculation of various coefficient distributions has been explained. However, in the third embodiment to the sixth embodiment described above, coefficient distributions can be calculated from a cross-correlation value or a difference among signals of multiple directions, and the like.

Moreover, the ultrasonic imaging method explained in the first embodiment to the sixth embodiment is applicable not only to when two-dimensional ultrasonic image data is imaged, but also to when volume data is imaged as a modification.

For example, when a mechanical 4D probe is used as the ultrasound probe 1, by compounding multiple tomograms acquired by mechanically swinging a transducer group, volume data is generated. In such a case, by designing a normal aperture function and an inverse aperture function for each tomogram, and by setting multiple directions with various deflection angles for each tomogram when the third embodiment to the sixth embodiment are combined to be used, high quality volume data in which reverberation is reduced and the lateral resolution and the sensitivity are maintained can be acquired.

Furthermore, for example, when a 2D array probe that performs three-dimensional scanning is performed in real time is used as the ultrasound probe 1, the ultrasonic imaging method explained in the first embodiment to the sixth embodiment is applicable. In such a case, by designing a two-dimensional normal aperture function and a two-dimensional inverse aperture function for normal apodization and inverse apodization, and by setting multiple directions in two dimension with various deflection angles also in depth directions in addition to horizontal directions on a surface on which 2D array transducers are arranged (transducer surface) when the third embodiment to the sixth embodiment are combined to be used, high quality volume data in which reverberation is reduced and the lateral resolution and the sensitivity are maintained can be acquired. In addition, two-dimensional image data that is generated from these volume data is also a high quality image in which reverberation is reduced and the lateral resolution and the sensitivity are maintained can be acquired.

Moreover, the ultrasonic imaging method explained in the first embodiment to the sixth embodiment and the modifications may be performed by a data processing apparatus that is arranged independently of the ultrasonography apparatus, and has functions of the data processing unit 15 and the control unit 18 described above.

Furthermore, among respective processing explained in the first embodiment to the sixth embodiment and the modifications, all or a part of processing that has been explained as one automatically performed may also be performed manually, or all or a part of processing that has been explained as one manually performed may also be performed automatically by a widely known method. In this case, the processing procedures, the control procedures, the specific names, and the information including various kinds of data and parameters indicated in the above document and the drawings can be changed arbitrarily unless otherwise specified.

Moreover, the illustrated respective components of the respective devices are functionally conceptual, and it is not necessarily required to be configured physically as illustrated. That is, specific forms of distribution and integration of the respective devices are not limited to ones illustrated, and all or a part thereof can be distributed or integrated to be configured functionally or physically in arbitrary units according to various kinds of loads and use conditions. Furthermore, as for the functions of processing performed in respective devices, all or a part thereof can be implemented by a central processing unit (CPU) and by a program that is analyzed and executed the CPU, or can be implemented as hardware by wired logic.

Moreover, the ultrasonic imaging method explained in the first embodiment to the sixth embodiment and the modifications can be implemented by executing an ultrasonic imaging program that is prepared in advance by a computer such as a personal computer and a workstation. This ultrasonic imaging method can be distributed through a network such as the Internet. Furthermore, this ultrasonic imaging method can be stored in a computer-readable recording medium such as a hard disk, a flexible disk (FD), a compact-disc read-only memory (CD-ROM), a magneto optical disk (MO), and a digital versatile disk (DVD), and can be executed by being read by a computer form the recording medium.

As explained above, according to the first embodiment to the sixth embodiment and the modifications, a high quality image in which reverberation is reduced and the lateral resolution and the sensitivity are maintained can be acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonography apparatus, comprising:
processing circuitry configured to
    acquire a first reception signal along a reception scan line, the first reception signal being generated by delaying a plurality of reflected wave signals occurring at a reception aperture that is structured with a plurality of devices included in an ultrasound probe, wherein the delaying is according to a position in the reception aperture, assigning a first kind of weights to the delayed plurality of reflected wave signals thereby generating first weighted reflected wave signals, and adding the first weighted reflected wave signals thereby generating the first reception signal;
    acquire a second reception signal along the reception scan line, the second reception signal having reverberation components that are reduced compared to that of the first reception signal, the second reception signal being generated by assigning a second kind of weights to the delayed plurality of reflected wave signals thereby generating second weighted reflected wave signals, and adding the second weights reflected wave signals thereby generating the second reception signal;
    calculate, based on the first reception signal any one of a first signal value and a first pixel value corresponding to each of a plurality of positions on the reception scan line;
    calculate, based on the second reception signal without using the first reception signal, any one of a second signal value and a second pixel value corresponding to each of the plurality of positions on the reception scan line;
    calculate a first coefficient corresponding to each of the plurality of positions on the reception scan line, based on said any one of the second signal value and the second pixel value;
    multiply said one of the first signal value and the first pixel value by the first coefficient to acquire output data; and
    generate ultrasonic image data based on the acquired output data.

2. An ultrasonography apparatus, comprising:
processing circuitry configured to
    acquire a first reception signal, the first reception signal being generated by delaying a plurality of reflected wave signals occurring at a reception aperture that is structured with a plurality of devices included in an ultrasound probe, wherein the delay is according to a position in the reception aperture, assigning a first kind of weights to the delayed plurality of reflected wave signals thereby generating first weighted reflected wave signals, and adding the first weighted reflected wave signals thereby generating the first reception signal;
    acquire a second reception signal along a reception scan line, the second reception signal having reverberation components that are reduced compared to that of the first reception signal, the second reception signal being generated by assigning a second kind of weights to the delayed plurality of reflected wave signals thereby generating second weighted reflected wave signals, and adding the second weighted reflected wave signals thereby generating the second reception signal;
    calculate a first coefficient using the second reception signal without using the first reception signal;
    multiply the first reception signal by the first coefficient to acquire output data; and
    generate ultrasonic image data based on the acquired output data.

3. The ultrasonography apparatus according to claim 2, wherein the first and second kinds of weights are defined by first and second aperture functions respectively.

4. The ultrasonography apparatus according to claim 3, wherein the second aperture function is an inverse aperture function in which a weight of a region including a reception position at which a reverberation component is received at the reception aperture is smaller than a weight of an outside of the region.

5. The ultrasonography apparatus according to claim 4, wherein the reception position at which the reverberation component is received is a central position of the reception aperture.

6. The ultrasonography apparatus according to claim 4, wherein the processing circuitry is further configured to:
calculate the reception position at which the reverberation component is received based on a direction of ultrasonic wave transmission/reception, and on a direction of a subject causing reverberation, and
create the inverse aperture function.

7. The ultrasonography apparatus according to claim 4, wherein the processing circuitry is further configured to:
calculate the reception position at which the reverberation component is received based on a direction of ultrasonic wave transmission/reception, on a direction of a subject causing reverberation, and on a depth of the subject, and
create the inverse aperture function.

8. The ultrasonography apparatus according to claim 6, wherein the processing circuitry is further configured to estimate the direction of the subject causing reverberation using the first reception signal, to set the inverse aperture function.

9. The ultrasonography apparatus according to claim 7, wherein the processing circuitry is further configured to estimate the direction of the subject causing reverberation using the first reception signal, to set the inverse aperture function.

10. The ultrasonography apparatus according to claim 2, wherein the second reception signal comprises a non-linear component extracted therefrom.

11. The ultrasonography apparatus according to claim 2, wherein the processing circuitry is further configured to calculate the first coefficient using a function including arithmetic processing of exponentiating an input value.

12. The ultrasonography apparatus according to claim 2, wherein the added first weighted reflected wave signals and the added second weighted reflected wave signals include phase information,
wherein the first reception signal is any one of a first phase added signal obtained by performing phasing addition on the added first weighted reflected wave signals, a first amplitude signal obtained by performing phase detection on the first phase added signal, and a first image signal obtained by performing logarithm compression on the first amplitude signal, and
wherein the second reception signal is any one of a second phase added signal obtained by performing phase addition on the added second weighted reflected wave signals, a second amplitude signal obtained by performing phase detection on the second phase added signal, and a second image signal obtained by performing logarithm compression on the second amplitude signal.

13. The ultrasonography apparatus according to claim 2, wherein the processing circuitry is further configured to:
acquire an image data group that is constituted of a plurality of pieces of ultrasonic image data with various deflection angles, wherein the plurality of pieces of ultrasonic image data are generated by ultrasonic scanning in which deflection angles in ultrasonic wave transmission/reception are varied among frames, the plurality of pieces of ultrasonic image data including a piece of ultrasonic image data with a deflection angle in a predetermined direction performed to acquire the first reception signal or the second reception signal and at least one piece of ultrasonic image data with a deflection angle in a direction other than the predetermined direction,
calculate a second coefficient using said at least one piece of ultrasonic image data with the deflection angle in the direction other than the predetermined direction, and
multiply any one of said piece of ultrasonic image data with the deflection angle in the predetermined direction, and compounded image data that is obtained by compounding the plurality of pieces of ultrasonic image data, by the first coefficient and the second coefficient.

14. The ultrasonography apparatus according to claim 2, wherein the processing circuitry is further configured to:
acquire a reception signal group that includes a plurality of reception signals with various deflection angles, wherein the plurality of reception signals are generated by ultrasonic scanning in which deflection angles in ultrasonic wave transmission/reception are varied as a function of time in the ultrasonic wave transmission/reception, the plurality of reception signals including a reception signal with a deflection angle in a predetermined direction performed to acquire the first reception signal or the second reception signal and at least one reception signal with a deflection angle in a direction other than the predetermined direction,
calculate a third coefficient using said at least one reception signal with the deflection angle in the direction other than the predetermined direction, and
multiply any one of said reception signal with the deflection angle in the predetermined direction, and a compounded signal that is obtained by compounding the plurality of reception signals, by the first coefficient and the third coefficient.

15. The ultrasonography apparatus according to claim 2, wherein the processing circuitry is further configured to:
acquire simultaneous reception-signal group that is constituted of a plurality of simultaneous reception signals with various deflections angles, wherein the plurality of simultaneous reception signals are generated by ultrasonic scanning in which reflections waves of a plurality of reception deflections angles are received by simultaneous reception for a transmission ultrasonic wave, the plurality of simultaneous reception signals including a simultaneous reception signal with a deflection angle in a predetermined direction and at least one simultaneous reception signal with a deflection angle in a direction other than a direction of the first reception signal and the second reception signal,
calculate a fourth coefficient using said at least one simultaneous reception signal with the deflection angle in the direction other than the direction of the first reception signal and the second reception signal, and
multiply any one of said simultaneous reception signal with the deflection angle in the predetermined direction, and a compounded signal that is obtained by compounding the plurality of simultaneous reception signals, by the first coefficient and the fourth coefficient.

16. The ultrasonography apparatus according to claim 13, wherein said at least one piece of ultrasonic image data is generated based on any one of:

an aperture function in which a weight at devices in a central portion of the reception aperture is larger than a weight at devices at an end portion of the reception aperture, an inverse aperture function in which a weight of a region including a reception position at which a reverberation component is received at the reception aperture is smaller than a weight of an outside of the region, and multiplying ultrasound image data with a deflection angle in a direction other than the predetermined direction by the first coefficient.

17. The ultrasonography apparatus according to claim 14, wherein said at least one reception signal is generated based on any one of:

an aperture function in which a weight at devices in a central portion of the reception aperture is larger than a weight at devices at an end portion of the reception aperture, an inverse aperture function in which a weight of a region including a reception position at which a reverberation component is received at the reception aperture is smaller than a weight of an outside of the region, and multiplying a reception signal with a deflection angle in a direction other than the predetermined direction by the first coefficient.

18. The ultrasonography apparatus according to claim 15, wherein said at least one simultaneous reception signal is generated based on any one of:

an aperture function in which a weight at devices in a central portion of the reception aperture is larger than a weight at devices at an end portion of the reception aperture, an inverse aperture function in which a weight of a region including a reception position at which a reverberation component is received at the reception aperture is smaller than a weight of an outside of the region, and multiplying a simultaneous reception signal with a deflection angle in a direction other than a direction of the first reception signal and the second reception signal by the first coefficient.

19. The ultrasonography apparatus according to claim 13, wherein said at least one piece of ultrasonic image data comprises a non-linear component extracted therefrom.

20. The ultrasonography apparatus according to claim 13, wherein the processing circuitry is further configured to calculate the second coefficient by using a function including arithmetic processing of exponentiating an input value.

21. An ultrasonic imaging method that is executed by a computer, the method comprising:

acquiring a first reception signal, the first reception signal being generated by delaying a plurality of reflected wave signals occurring at a reception aperture that is structured with a plurality of devices included in an ultrasound probe, wherein the delaying is according to a position in the reception aperture, assigning a first kind of weights to the delayed plurality of reflected wave signals thereby generating first weighted reflected wave signals, and adding the first weighted reflected wave signals thereby generating the first reception signal;

acquiring a second reception signal along a reception scan line, the second reception signal having reverberation components that are reduced compared to that of the first reception signal, the second reception signal being generated by assigning a second kind of weights to the delayed plurality of reflected wave signals thereby generating second weighted reflected wave signals, and adding the second weighted reflected wave signals thereby generating the second reception signal;

calculating a first coefficient using the second reception signal without using the first reception signal;

multiplying the first reception signal by the first coefficient to acquire output data; and generating ultrasonic image data based on the acquired output data.

\* \* \* \* \*